United States Patent
Nishimura et al.

(10) Patent No.: US 9,585,885 B2
(45) Date of Patent: Mar. 7, 2017

(54) SUBSTITUTED PYRIDO[2,3-G]QUINAZOLINES AS DOPAMINE $D_2$ RECEPTOR AGONISTS

(71) Applicant: KISSEI PHARMACEUTICAL CO., LTD., Matsumoto-shi, Nagano (JP)

(72) Inventors: Toshihiro Nishimura, Azumino (JP); Yasunori Ueno, Azumino (JP); Kiyoshi Kasai, Azumino (JP); Masako Yoshida, Azumino (JP)

(73) Assignee: KISSEI PHARMACEUTICAL CO., LTD., Matsumoto-shi (JP)

( * ) Notice: Subject to any disclaimer, the term of this patent is extended or adjusted under 35 U.S.C. 154(b) by 87 days.

(21) Appl. No.: 14/650,786

(22) PCT Filed: Dec. 6, 2013

(86) PCT No.: PCT/JP2013/082777
§ 371 (c)(1),
(2) Date: Jun. 9, 2015

(87) PCT Pub. No.: WO2014/092006
PCT Pub. Date: Jun. 19, 2014

(65) Prior Publication Data
US 2015/0315183 A1     Nov. 5, 2015

(30) Foreign Application Priority Data
Dec. 10, 2012   (JP) ................. 2012-269182

(51) Int. Cl.
| | | |
|---|---|---|
| *A61K 31/519* | (2006.01) | |
| *C07D 487/14* | (2006.01) | |
| *C07D 471/04* | (2006.01) | |
| *A61K 45/06* | (2006.01) | |
| *A61K 31/55* | (2006.01) | |
| *C12N 15/09* | (2006.01) | |
| *A61K 31/13* | (2006.01) | |
| *A61K 31/198* | (2006.01) | |
| *A61K 31/423* | (2006.01) | |

(52) U.S. Cl.
CPC ............ *A61K 31/519* (2013.01); *A61K 31/13* (2013.01); *A61K 31/198* (2013.01); *A61K 31/423* (2013.01); *A61K 31/55* (2013.01); *A61K 45/06* (2013.01); *C07D 471/04* (2013.01); *C12N 15/09* (2013.01)

(58) Field of Classification Search
CPC ........................... A61K 31/519; C07D 487/14
USPC .......................................... 514/267; 544/250
See application file for complete search history.

(56) References Cited

U.S. PATENT DOCUMENTS

| | | |
|---|---|---|
| 3,953,454 A | 4/1976 | Zikan et al. |
| 4,521,421 A | 6/1985 | Foreman |
| 4,826,986 A | 5/1989 | Huser et al. |
| 4,977,160 A | 12/1990 | Huser et al. |
| 5,134,143 A | 7/1992 | Huser et al. |
| 2014/0243311 A1 | 8/2014 | Nishimura et al. |

FOREIGN PATENT DOCUMENTS

| | | |
|---|---|---|
| JP | 48-26799 A | 4/1973 |
| JP | 60-72891 A | 4/1985 |
| JP | 62-298589 A | 12/1987 |
| WO | 2012/124649 A1 | 9/2012 |

OTHER PUBLICATIONS

International Search Report for PCT/JP2013/082777 dated Mar. 11, 2014 [PCT/ISA/210].

*Primary Examiner* — Douglas M Willis
(74) *Attorney, Agent, or Firm* — Sughrue Mion, PLLC

(57) ABSTRACT

[Problem] To provide a novel compound that exhibits an agonistic effect on dopamine $D_2$ receptors.
[Solution] The present invention provides a compound represented by the general formula (I):

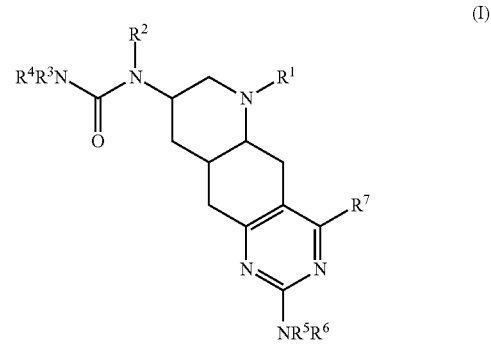

in which $R^1$ is $C_{1-6}$ alkyl or the like; $R^2$ is hydrogen or the like; $R^3$ and $R^4$ are each hydrogen, $C_{1-6}$ alkyl, $R^{10}R^{11}N$—$C_{1-6}$ alkyl, aralkyl, or the like; $R^5$ and $R^6$ are hydrogen or the like; and $R^7$ is hydrogen or the like, or a pharmaceutically acceptable salt thereof, a pharmaceutical compositions containing same and uses for said compound/salt and composition. The compounds of the present invention exhibit potent dopamine $D_2$ receptor simulating activities and thus are useful as a treating or preventing agent for Parkinson's disease and the like.

11 Claims, No Drawings

SUBSTITUTED PYRIDO[2,3-G]QUINAZOLINES AS DOPAMINE $D_2$ RECEPTOR AGONISTS

CROSS REFERENCE TO RELATED APPLICATIONS

This application is a National Stage of International Application No. PCT/JP2013/082777, filed on Dec. 6, 2013, which claims priority from Japanese Patent Application No. 2012-269182, filed on Dec. 10, 2012, the contents of all of which are incorporated herein by reference in their entirety.

TECHNICAL FIELD

The present invention relates to novel octahydropyridoquinazoline derivatives, which exhibit dopamine $D_2$ receptor agonistic activities, pharmaceutical compositions containing the same, and their uses.

BACKGROUND ART

Parkinson's disease is a progressive neurodegenerating disease which usually affects elderly patients, and the number of parkinsonian patients is growing with progressive aging of society. Parkinson's disease pathogenesis is characterized by impairment in coordinated motor function such as rest tremor, rigidity, akinesia, postural instability and the like. It is thought that Parkinson's disease results from deficiency of dopamine in the striatum, which is caused by degeneration of dopamine neuron in the substantia nigra. For that reasons, L-dopa or dopamine $D_2$ receptor agonists are used for the treatment of Parkinson's disease.

L-dopa is a precursor of dopamine, and is metabolized to dopamine which exerts its efficacy in the brain. Since L-dopa has a very short serum half-life, L-dopa is administered usually in combination with a peripheral aromatic L-amino acid decarboxylase inhibitor and/or a catechol-O-methyltransferase inhibitor, which are the metabolizing enzyme inhibitors of L-dopa.

Dopamine $D_2$ receptor agonists exert an anti-Parkinson's effect by directly stimulating dopamine $D_2$ receptors of the striatum. And, it is known that the dopamine $D_2$ receptor agonists are useful for treating restless legs syndrome, hyperprolactinemia or the like (for example, see Non-patent literature 1 or 2).

Various ergot or non-ergot dopamine $D_2$ receptor agonists are known as dopamine $D_2$ receptor agonist (for example, see Patent literatures 1 to 3 about ergot dopamine $D_2$ receptor agonist, and see Patent literatures 4 to 6 about non-ergot dopamine $D_2$ receptor agonist).

The non-ergot dopamine $D_2$ receptor agonists have the disadvantage of a duration of action is shorter than the ergot dopamine $D_2$ receptor agonists, since the serum half-life of them is shorter than the ergot dopamine $D_2$ receptor agonists (for example, see Non-patent literature 3). And more, the non-ergot dopamine $D_2$ receptor agonists have problems of side effects such as sudden onset of sleep, somnolence or the like.

The ergot dopamine $D_2$ agonists show the long-term effectiveness compared to the non-ergot dopamine $D_2$ receptor agonists. However, recently it has been reported that the risk of onset of cardiac valvular disease increases when taken long-term and high dose of pergolide which is a typical ergot dopamine $D_2$ receptor agonist. So, the periodic monitoring of echocardiography and the like are required during administering the ergot dopamine $D_2$ receptor agonists. Since it is reported that cardiac valvular disease is caused by the growth stimulation of the cardiac valvular cells by the stimulation activity of $5\text{-HT}_{2B}$ receptor as pathogenesis of cardiac valvular disease, the relevance of cardiac valvular diseases and the stimulation activity of $5\text{-HT}_{2B}$ receptor is strongly suggested (for example, see Non-patent literature 4).

Accordingly, it has been expected for novel dopamine $D_2$ receptor agonists exhibiting potent and lasting dopamine $D_2$ receptor agonistic activities with less $5\text{-HT}_{2B}$ receptor stimulating activities.

As octahydropyridoquinazoline derivatives, the following compounds are known (see Patent literature 7).

[Chem. 1]

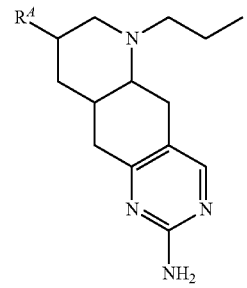

in which $R^A$ is $CH_2OH$, $CH_2OCH_3$ or $CH_2SCH_3$.

However, anything is neither described nor suggested about the compounds substituted with an ureido group as $R^A$ in the Patent reference 7. And more, dopamine D2 receptor stimulation activity of the compounds of Patent literature 7 are not insufficient as shown in the following test example.

CITATION LIST

Patent Literature

Patent literature 1: U.S. Pat. No. 4,166,182.
Patent literature 2: U.S. Pat. No. 3,752,814.
Patent literature 3: U.S. Pat. No. 4,526,892.
Patent literature 4: U.S. Pat. No. 4,452,808.
Patent literature 5: U.S. Pat. No. 3,804,849.
Patent literature 6: U.S. Pat. No. 4,886,812.
Patent literature 7: Publication of Unexamined Application of European Patent Specification No. 250179.

Non-Patent Literature

Non-patent literature 1: Happe, S. et al, CNS Drugs, 2004, vol. 18(1), pp. 27-36
Non-patent literature 2: Crosignani, P. G. et al, Eur. J. Obstetrics & Gynecology and Reproductive Biology, 2006, vol. 125, pp. 152-164
Non-patent literature 3: Prikhojan, A. et al, J. Neural Transm., 2000, vol. 107, pp. 1159-1164
Non-patent literature 4: Setola, V. et al, Mol. Pharmacol., 2003, vol. 63, pp. 1223-1229

SUMMARY OF THE INVENTION

Problem to be Solved by the Invention

An object of the present invention is to provide a novel compound having potent dopamine $D_2$ receptor stimulating activities, and more preferably a compound alleviated 5-$HT_{2B}$ receptor stimulating activities.

Means for Solving the Problem

The inventors of the present invention diligently worked to achieve the foregoing object and found surprisingly that compounds represented by the general formula (I) show highly potent dopamine $D_2$ receptor simulating activities as compared to 5-$HT_{2B}$ receptor simulating activities. Based on these findings, the present invention has been accomplished.

That is, the present invention relates to:

a compound represented by the general formula (I):

[Chem. 2]

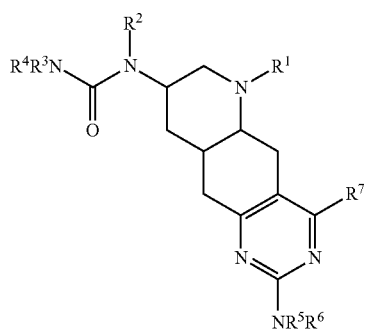

(I)

or a pharmaceutically acceptable salt thereof,
wherein
$R^1$ is any one of the following a) to c):
a) a $C_{1-6}$ alkyl group,
b) a halo-$C_{1-6}$ alkyl group, or
c) a $C_{2-6}$ alkenyl group;
$R^2$ is a hydrogen atom or a $C_{1-6}$ alkyl group;
$R^3$ and $R^4$ are each independently any one of the following a) to g):
a) a hydrogen atom,
b) a $C_{1-6}$ alkyl group,
c) a cycloalkyl group,
d) an aralkyl group, wherein the ring of the aralkyl group is unsubstituted or substituted with 1 to 5 substituents selected from the group consisting of a halogen atom, a $C_{1-6}$ alkyl group, a halo-$C_{1-6}$ alkyl group, a $C_{1-6}$ alkoxy group, and a hydroxy-$C_{1-6}$ alkyl group,
e) a heteroaryl-$C_{1-6}$ alkyl group, wherein the ring of the heteroaryl-$C_{1-6}$ alkyl group is unsubstituted or substituted with 1 to 3 substituents independently selected from the group consisting of a $C_{1-6}$ alkyl group, a halo-$C_{1-6}$ alkyl group, and a $C_{1-6}$ alkoxy group,
f) a $C_{1-6}$ alkoxy-$C_{1-6}$ alkyl group, or
g) a $R^{10}R^{11}N$—$C_{1-6}$ alkyl group,
or $R^3$ and $R^4$, together with the nitrogen atom to which they are bonded, form
a) a cyclic amino group unsubstituted or substituted with 1 or 2 $C_{1-6}$ alkyl groups or phenyl groups, or
b) a benzo-fused cyclic amino group;
$R^5$ and $R^6$ are each independently any one of a hydrogen atom or a $C_{1-7}$ acyl group;
$R^7$ is any one of the following a) to e):
a) a hydrogen atom,
b) a halogen atom,
c) a $C_{1-6}$ alkyl group,
d) an amino group, or e) a hydroxy group;
$R^{10}$ and $R^{11}$ are each independently any one of the following a) to f):
a) a hydrogen atom,
b) a $C_{1-6}$ alkyl group,
c) a cycloalkyl group,
d) a $C_{1-6}$ alkoxy-$C_{1-6}$ alkyl group,
e) a phenyl group, or
f) a aralkyl group,
or $R^{10}$ and $R^{11}$, together with the nitrogen atom to which they are bonded, form a) a cyclic amino group unsubstituted or substituted with 1 or 2 halogen atoms, $C_{1-6}$ alkyl groups or phenyl groups, or b) a benzo-fused cyclic amino group.

In another aspect, the present invention relates to a pharmaceutical composition which comprises, as an active ingredient, a compound represented by the general formula (I) or a pharmaceutically acceptable salt thereof.

In still another aspect, the present invention relates to a therapeutic or prophylactic agent for Parkinson's disease, restless legs syndrome or hyperprolactinemia which comprises a compound represented by the general formula (I) or a pharmaceutically acceptable salt thereof.

In still another aspect, the present invention relates to a dopamine $D_2$ receptor agonist comprising a compound represented by the general formula (I) or a pharmaceutically acceptable salt thereof.

In still another aspect, the present invention relates to a pharmaceutical agent which comprises a combination of (1) a compound represented by the general formula (I) or a pharmaceutically acceptable salt thereof and (2) at least one anti-Parkinson drug selected from L-dopa, dopamine $D_2$ receptor agonists, anticholinergic agents, adenosine $A_{2A}$ receptor antagonists, NMDA receptor antagonists, monoamine oxidase B inhibitors, COMT inhibitors, aromatic L-amino acid decarboxylase inhibitors, droxidopa, melevodopa, threodops, zonisamide and amantadine hydrochloride.

Effects of the Invention

The compounds of the present invention exhibit potent dopamine $D_2$ receptor simulating activities. Moreover, compounds of the present invention have a desirable safety profile since compounds of the present invention have extremely slight 5-$HT_{2B}$ receptor stimulating activities. Accordingly, compounds of the present invention are useful as a treating or preventing agent for Parkinson's disease, restless legs syndrome or hyperprolactinemia.

EMBODIMENTS FOR CARRYING OUT THE INVENTION

In a compound represented by the general formula (I), the following terms have the following meanings unless otherwise specified.

The term "halogen atom" refers to a fluorine atom, a chlorine atom, a bromine atom or an iodine atom.

The term "$C_{1-6}$ alkyl group" refers to a straight chained or a branched alkyl group having 1 to 6 carbon atoms such as a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a 1-methylbutyl group, a 2-methylbutyl group, a 1,2-dimethylpropyl group, a hexyl group, an isohexyl group and the like.

The term "halo-$C_{1-6}$ alkyl group" refers to an alkyl group having 1 to 6 carbon atoms substituted with the same or different 1 to 3 halogen atoms such as a fluoromethyl group, a 2-fluoroethyl group, a difluoromethyl group, a trifluoromethyl group, a 2,2,2-trifluoroethyl group, a 3,3,3-trifluoropropyl group, a 4,4,4-trifluorobutyl group and the like.

The term "hydroxyl-$C_{1-6}$ alkyl group" refers to an alkyl group having 1 to 6 carbon atoms substituted with a hydroxy group such as a hydroxymethyl group, a 1-hydroxyethyl group, a 1-hydroxy-1,1-dimethylmethyl group, a 2-hydroxyethyl group, a 2-hydroxy-2-methylpropyl group, a 3-hydroxypropyl group and the like.

The term "$C_{1-6}$ alkoxy group" refers to a straight chained or branched alkoxy group having 1 to 6 carbon atoms such as a methoxy group, an ethoxy group, a propoxy group, an isopropoxy group, a butoxy group, an isobutoxy group, a sec-butoxy group, a tert-butoxy group, a pentyloxy group, a hexyloxy group and the like.

The term "$C_{1-7}$ acyl group" refers to a formyl group or a group represented by a ($C_{1-6}$ alkyl)-C(O)— such as a formyl group, an acetyl group, a propionyl group, a butyryl group, an isobutyryl group, a pivaloyl group, a valeryl group, an isovaleryl group and the like.

The term "cycloalkyl group" refers to a 3- to 7-membered saturated cyclic hydrocarbon such as a cyclopropyl group, a cyclobutyl group, a cyclopentyl group, a cyclohexyl group and a cycloheptyl group.

The term "aryl group" refers to a $C_{6-10}$ aromatic hydrocarbon group such as a phenyl group, a 1-naphtyl group and a 2-naphtyl group, preferably a phenyl group.

The term "heteroaryl group" refers to a 5- or 6-membered monocyclic aromatic heterocycle having 1 to 5 carbon atoms and 1 to 4 heteroatoms selected independently from the group consisting of O, N and S atoms, or a 8- to 10-membered bicyclic aromatic heterocycle having 1 to 9 carbon atoms and 1 to 4 heteroatoms selected independently from the group consisting of an oxygen atom, nitrogen atom and sulfur atom with the proviso that these rings do not include adjacent oxygen and/or sulfur atoms.

Examples of monocyclic aromatic heteroaryl groups include pyrrolyl, furyl, thienyl, imidazolyl, pyrazolyl, oxazolyl, isoxazolyl, 1,2,4-oxadiazolyl, 1,3,4-oxadiazolyl, tetrazolyl, thiazolyl, isothiazolyl, 1,2,3-thiadiazolyl, triazolyl, pyridyl, pyrazinyl, pyrimidyl, pyridazinyl and the like, preferably thienyl, imidazolyl, thiazolyl or pyridyl.

Examples of bicyclic aromatic heteroaryl groups include indazolyl, benzofuranyl, benzothienyl, benzothiazolyl, quinolyl, isoquinolyl, phthalazinyl, benzimidazolyl, benzoxazolyl and the like. These heterocycles include all position isomers such as 2-pyridyl, 3-pyridyl or 4-pyridyl.

The term "aralkyl group" refers to an aryl-$C_{1-6}$ alkyl group such as a benzyl group, a phenethyl group, a 1-phenylethyl group, a 3-phenylpropyl group, a 4-phenylbutyl group, a naphthylmethyl group and the like.

The term "heteroaryl-$C_{1-6}$ alkyl group" refers to a 2-pyridylmethyl group, a 3-pyridylmethyl group, a 4-pyridylmethyl group, a 2-pyridylethyl group, a 3-pyridylethyl group, a 4-pyridylethyl group, a 2-thienylmethyl group, an imidazol-1-ylmethyl group, an 2-imidazol-3-ylmethyl group, an 2-imidazol-1-ylethyl group, an 3-imidazol-1-ylpropyl group, a 2-thiazolylmethyl group and the like.

The term "$C_{2-6}$ alkenyl group" refers to a straight chained or branched unsaturated hydrocarbon group having 2 to 6 carbon atoms such as $CH_2$=$CHCH_2$—, $CH_2$=$CHCH_2CH_2$—, $CH_3CH$=$CHCH_2$— and the like.

The term "$C_{1-6}$ alkoxy-$C_{1-6}$ alkyl group" includes a 2-methoxyethyl group, a 3-methoxypropyl group, an 2-ethoxyethyl group, an 3-ethoxypropyl group and the like.

The term "cyclic amino group" refers to a 5- to 7-membered saturated cyclic amine which may contain —NH—, —O— or —S— in the ring. Examples of cyclic amino groups include a 1-pyrrolidyl group, a piperidinyl group, a piperazinyl group, a morpholinyl group, a thiomorpholinyl group, a [1,4]diazepan-1-yl group and the like.

The term "benzo-fused cyclic amino group" refers to a cyclic amino group fused with a benzene ring such as a tetrahydroisoquinolyl group and the like.

The numbering of the ring atoms of the compound represented by the general formula (I) is given as follows:

[Chem. 3]

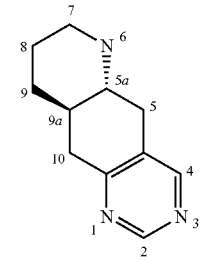

The numbering of the ring atoms of the reference example represented in the following Tables 1 to 8 by the general formula (I) is given as follows.

[Chem. 4]

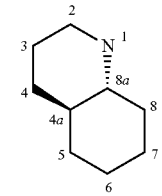

In a chemical name in the present description, the mark "*" mean the relative configuration of the asymmetric carbon atom. For example, 3-[(5aR*,8S*,9aR*)-2-amino-6-propyl-5,5a,6,7,8,9,9a,10-octahydropyrido[2,3-g]quinazolin-8-yl]-1,1-diethylurea (Compound 1-7) means that the asymmetric carbons at 5a, 8 and 9a positions are relative configurations.

In the case where a compound represented by the general formula (I) of the present invention contains one or more asymmetric carbon atoms, all stereoisomers in the R- or S-configuration at each of asymmetric carbons and their mixtures are included in the scope of the present invention. In such cases, racemic compounds, racemic mixtures, racemic solid solutions, individual enantiomers and mixtures of diastereomers are included in the scope of the present invention. In the case where a compound represented by the general formula (I) has the geometrical isomers, all geometrical isomers are included in the scope of the present invention. In the case where a compound represented by the general formula (I) has the atropisomers, all atropisomers are included in the scope of the present invention. Moreover, a compound represented by the general formula (I) or a pharmaceutically acceptable salt thereof also includes a solvate with a pharmaceutically acceptable solvent such as water, ethanol and the like.

Compounds represented by the general formula (I) of the present invention may exist in the form of salts. Examples of such salts include acid addition salts formed with mineral acids such as hydrochloric acid, hydrobromic acid, hydroiodic acid, sulfuric acid, nitric acid, phosphoric acid and the like; acid addition salts formed with organic acids such as formic acid, acetic acid, trifluoroacetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid and the like; salts formed with inorganic bases such as a lithium salt, a sodium salt, a potassium salt, a calcium salt, a magnesium salt and the like; salts formed with organic bases such as triethylamine, piperidine, morpholine, lysine and the like.

In an embodiment of a compound represented by the general formula (I) of the present invention,
$R^1$ is preferably a $C_{1-6}$ alkyl group;
$R^2$ is preferably a hydrogen atom;
$R^3$ is preferably any one of the following a) to c):
a) a hydrogen atom,
b) a $C_{1-6}$ alkyl group, or
c) an aralkyl group, wherein the ring of the aralkyl group is unsubstituted or substituted with 1 to 5 substituents selected from the group consisting of a halogen atom, a $C_{1-6}$ alkyl group, a halo-$C_{1-6}$ alkyl group, a $C_{1-6}$ alkoxy group and a hydroxy-$C_{1-6}$ alkyl group;
more preferably $R^3$ is any one of the following a) to b):
a) a $C_{1-6}$ alkyl group, or
c) an aralkyl group, wherein the ring of the aralkyl group is unsubstituted or substituted with 1 to 5 substituents selected from the group consisting of a halogen atom, a $C_{1-6}$ alkyl group, a halo-$C_{1-6}$ alkyl group, a $C_{1-6}$ alkoxy group and a hydroxy-$C_{1-6}$ alkyl group,
$R^4$ is preferably any one of the following a) to f):
a) a $C_{1-6}$ alkyl group,
b) a cycloalkyl group,
c) an aralkyl group, wherein the ring of the aralkyl group is unsubstituted or substituted with 1 to 5 substituents selected from the group consisting of a halogen atom, a $C_{1-6}$ alkyl group, a halo-$C_{1-6}$ alkyl group, a $C_{1-6}$ alkoxy group and a hydroxy-$C_{1-6}$ alkyl group,
d) a heteroaryl-$C_{1-6}$ alkyl group, wherein the ring of the heteroaryl-$C_{1-6}$ alkyl group is unsubstituted or substituted with 1 to 3 substituents independently selected from the group consisting of a $C_{1-6}$ alkyl group, a halo-$C_{1-6}$ alkyl group, and a $C_{1-6}$ alkoxy group,
e) a $C_{1-6}$ alkoxy-$C_{1-6}$ alkyl group, or
f) a $R^{10}R^{11}N$—$C_{1-6}$ alkyl group;
more preferably $R^4$ is a $R^{10}R^{11}N$—$C_{1-6}$ alkyl group, or $R^3$ and $R^4$, together with the nitrogen atom to which they are bonded, form
a) a cyclic amino group unsubstituted or substituted with 1 or 2 $C_{1-6}$ alkyl groups or phenyl groups, or
b) a benzo-fused cyclic amino group;
or more preferably $R^3$ and $R^4$, together with the nitrogen atom to which they are bonded, form a cyclic amino group, wherein the cyclic amino group is unsubstituted or substituted with 1 or 2 $C_{1-6}$ alkyl groups or phenyl groups;
$R^5$ and $R^6$ are preferably a hydrogen atom; or
$R^7$ is preferably a hydrogen atom.

In an embodiment of a compound represented by the general formula (I),
a compound represented by the general formula (I) is preferably a general formula (II),

[Chem. 5]

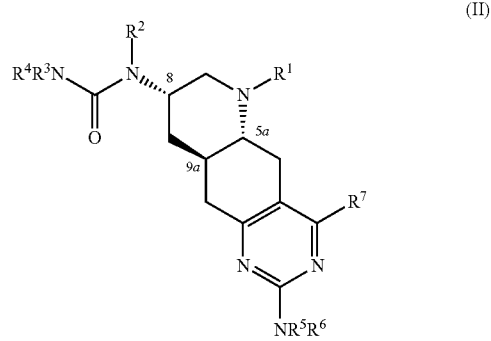

(II)

wherein the configuration at 5a, 8 and 9a positions of the ring of 5,5a,6,7,8,9,9a,10-octahydropyrido[2,3-g]quinazoline is represented by a relative configuration;
more preferably a compound represented by the general formula (I) is a general formula (II),

[Chem. 6]

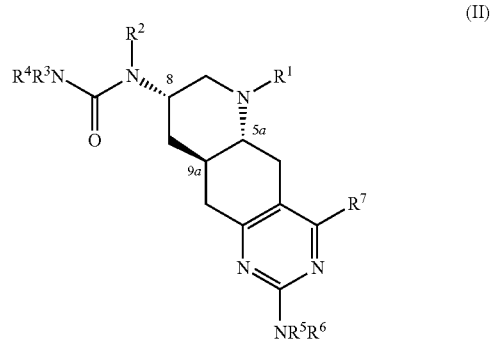

(II)

wherein the configuration at 5a, 8 and 9a positions of the ring of 5,5a,6,7,8,9,9a,10-octahydropyrido[2,3-g]quinazoline is represented by an absolute configuration.

In a preferable embodiment of the present invention,
$R^5$, $R^6$ and $R^7$ are a hydrogen atom.

In a more preferable embodiment of the present invention,
$R^1$ is a $C_{1-6}$ alkyl group; and
$R^5$, $R^6$ and $R^7$ are a hydrogen atom.

In an even more preferable embodiment of the present invention,
$R^1$ is a $C_{1-6}$ alkyl group;
$R^2$ is a hydrogen atom; and
$R^5$, $R^6$ and $R^7$ are a hydrogen atom.

In an even more preferable embodiment of the present invention,
$R^1$ is a $C_{1-6}$ alkyl group;
$R^2$ is a hydrogen atom;
$R^3$ is any one of the following a) to c):
a) a hydrogen atom,
b) a $C_{1-6}$ alkyl group, or
c) an aralkyl group, wherein the ring of the aralkyl group is unsubstituted or substituted with 1 to 5 substituents selected from the group consisting of a halogen atom, a $C_{1-6}$ alkyl group, a halo-$C_{1-6}$ alkyl group, a $C_{1-6}$ alkoxy group and a hydroxy-$C_{1-6}$ alkyl group;

$R^4$ is any one of the following a) to f):
a) a $C_{1-6}$ alkyl group,
b) a cycloalkyl group,
c) an aralkyl group, wherein the ring of the aralkyl group is unsubstituted or substituted with 1 to 5 substituents selected from the group consisting of a halogen atom, a $C_{1-6}$ alkyl group, a halo-$C_{1-6}$ alkyl group, a $C_{1-6}$ alkoxy group and a hydroxy-$C_{1-6}$ alkyl group,
d) a heteroaryl-$C_{1-6}$ alkyl group, wherein the ring of the heteroaryl-$C_{1-6}$ alkyl group is unsubstituted or substituted with 1 to 3 substituents independently selected from the group consisting of a $C_{1-6}$ alkyl group, a halo-$C_{1-6}$ alkyl group, and a $C_{1-6}$ alkoxy group,
e) a $C_{1-6}$ alkoxy-$C_{1-6}$ alkyl group, or
f) a $R^{10}R^{11}N$—$C_{1-6}$ alkyl group,
or $R^3$ and $R^4$, together with the nitrogen atom to which they are bonded, form
a) a cyclic amino group unsubstituted or substituted with 1 or 2 $C_{1-6}$ alkyl groups or phenyl groups, or
b) a benzo-fused cyclic amino group; and
$R^5$, $R^6$ and $R^7$ are a hydrogen atom.

In an even more preferable embodiment of the present invention,
$R^1$ is a $C_{1-6}$ alkyl group;
$R^2$ is a hydrogen atom;
$R^3$ is any one of the following a) to b):
a) a $C_{1-6}$ alkyl group, or
b) an aralkyl group, wherein the ring of the aralkyl group is unsubstituted or substituted with 1 to 5 substituents selected from the group consisting of a halogen atom, a $C_{1-6}$ alkyl group, a halo-$C_{1-6}$ alkyl group, a $C_{1-6}$ alkoxy group and a hydroxy-$C_{1-6}$ alkyl group;

$R^4$ is a $R^{10}R^{11}N$—$C_{1-6}$ alkyl group, or
or $R^3$ and $R^4$, together with the nitrogen atom to which they are bonded, form a cyclic amino group, wherein the cyclic amino group is unsubstituted or substituted with 1 or 2 $C_{1-6}$ alkyl groups or phenyl groups; and
$R^5$, $R^6$ and $R^7$ are a hydrogen atom.

Specific examples of preferred embodiments of the present invention are compounds selected form the group consisting of:
3-[(5aR,8S,9aR)-2-amino-6-propyl-5,5a,6,7,8,9,9a,10-octahydropyrido[2,3-g]quinazolin-8-yl]-1-[2-(dimethylamino)ethyl]-1-ethylurea (Compound 1-1);
3-[(5aR,8S,9aR)-2-amino-6-propyl-5,5a,6,7,8,9,9a,10-octahydropyrido[2,3-g]quinazolin-8-yl]-1-[2-(dimethylamino)ethyl]-1-propylurea (Compound 1-2);
3-[(5aR,8S,9aR)-2-amino-6-propyl-5,5a,6,7,8,9,9a,10-octahydropyrido[2,3-g]quinazolin-8-yl]-1-[2-(dimethylamino)ethyl]-1-(2-methylpropyl)urea (Compound 1-3);
3-[(5aR,8S,9aR)-2-amino-6-propyl-5,5a,6,7,8,9,9a,10-octahydropyrido[2,3-g]quinazolin-8-yl]-1-[2-(diethylamino)ethyl]-1-methylurea (Compound 1-4);
3-[(5aR*,8S*,9aR*)-2-amino-6-propyl-5,5a,6,7,8,9,9a,10-octahydropyrido[2,3-g]quinazolin-8-yl]-1-[2-(dimethylamino)ethyl]-1-(2-phenylethyl)urea (Compound 1-23); and
3-[(5aR*,8S*,9aR*)-2-amino-6-propyl-5,5a,6,7,8,9,9a,10-octahydropyrido[2,3-g]quinazolin-8-yl]-1-ethyl-1-[2-(piperidin-1-yl)ethyl]urea (Compound 1-25).

Compounds represented by the general formula (I) of the present invention can be prepared by methods as illustrated in schemes 1 to 3.

[Chem.7]

Scheme 1

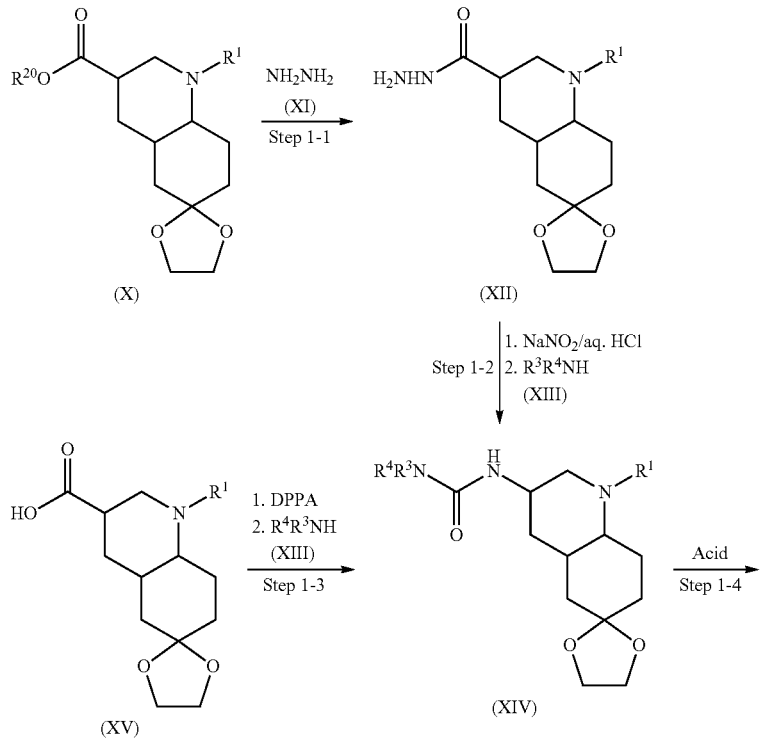

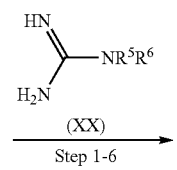

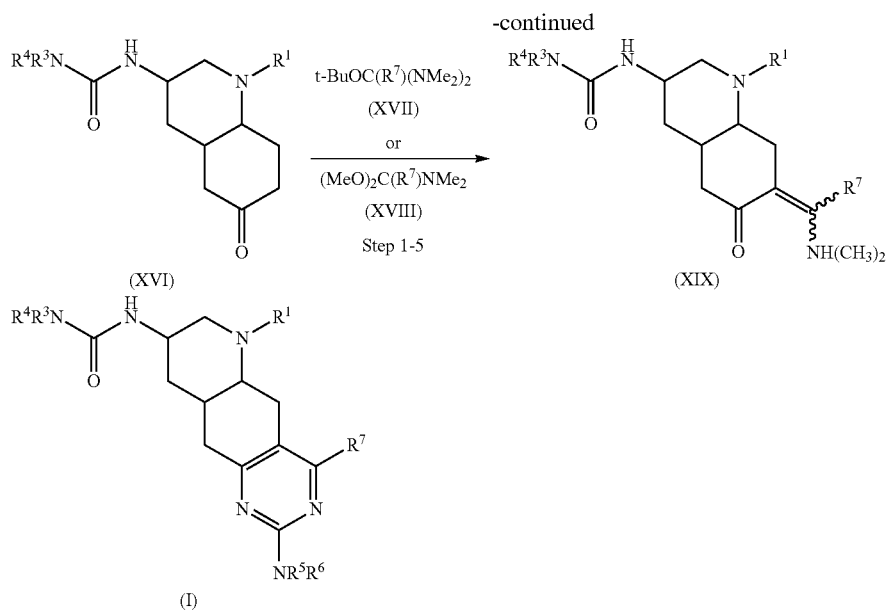

In the formula, $R^1$, $R^2$, $R^3$, $R^4$, $R^5$ and $R^6$ have the same meanings as defined above; and $R^7$ is a hydrogen atom or a $C_{1-6}$ alkyl group, $R^{20}$ is a $C_{1-6}$ alkyl group.

Step 1-1

A carboxylic acid hydrazide derivative (XII) can be prepared by condensing an ester derivative (X) with Hydrazine (XI) in a suitable solvent. As the solvent used in the reaction, for example, 1-propanol, 2-butanol and the like can be illustrated. The reaction temperature is usually at 0° C. to 110° C., the reaction time is usually 1 hour to 48 hours, varying based on the starting materials employed, the solvent, the reaction temperature and the like.

Step 1-2

A carboxylic acid azide derivative can be prepared by allowing a carboxylic acid hydrazide derivative (XII) to react with sodium nitrite in the presence of an acid in a suitable solvent. As the solvent used in the reaction, for example, water and the like can be illustrated. As the acid, for example, hydrochloric acid and the like can be illustrated. The reaction temperature is usually at −20° C. to 40° C., the reaction time is usually 10 minuets to 4 hours, varying based on the starting materials employed, the solvent, the reaction temperature and the like.

An urea derivative (XIV) can be prepared by converting an a carboxylic acid azide derivative to isocyanate derivative according to conventional methods, followed by reacting with Amine (XIII) or the salt thereof in an inert solvent in the presence or absence of a base. As the inert solvent used in the reaction, for example, toluene, tetrahydrofuran, methylene chloride, a mixed solvent thereof and the like can be illustrated. As the base, for example, triethylamine, N,N-diisopropylethylamine and the like can be illustrated. The reaction temperature is usually at −10° C. to reflux temperature, the reaction time is usually 30 minutes to 24 hours, varying based on the starting materials employed, the solvent, the reaction temperature and the like.

Step 1-3

Alternatively, an urea derivative (XIV) can be prepared by the following method. An isocyanate derivative can be prepared by allowing a carboxylic acid derivative (XV) to react with diphenylphosphoryl azide (DPPA) in an inert solvent in the presence of a base. As the inert solvent used in the reaction, for example, toluene and the like can be illustrated. As the base, for example, triethylamine, N,N-diisopropylethylamine and the like can be illustrated. The reaction temperature is usually at room temperature to reflux temperature, the reaction time is usually 10 minutes to 4 hours, varying based on the starting materials employed, the solvent, the reaction temperature and the like.

An urea derivative (XIV) can be prepared by allowing an isocyanate derivative to react with Amine (XIII) or salt thereof in an inert solvent in the presence or absence of a base. As the inert solvent used in the reaction, for example, toluene, tetrahydrofuran, methylene chloride, a mixed solvent thereof and the like can be illustrated. As the base, for example, triethylamine, N,N-diisopropylethylamine and the like can be illustrated. The reaction temperature is usually at −10° C. to reflux temperature, the reaction time is usually 30 minutes to 24 hours, varying based on the starting materials employed, the solvent, the reaction temperature and the like.

Step 1-4

A 6-oxodecahydroquinoline derivative (XVI) can be prepared by acid hydrolysis of a ketal derivative (XIV) in a suitable solvent. As the solvent used in the reaction, for example, tetrahydrofuran, dimethoxyethane, 1,4-dioxane, methylene chloride, 1,2-dichloroethane, chloroform, water, a mixed solvent thereof and the like can be illustrated. As the acid, for example, sulfuric acid, hydrochloric acid, phosphoric acid, acetic acid, methanesulfonic acid, benzenesulfonic acid and the like can be illustrated. The reaction temperature is usually at −50° C. to 100° C., the reaction time is usually 10 minuets to 24 hours, varying based on the starting materials employed, the solvent, the reaction temperature and the like.

Step 1-5

A 7-[(dimethylamino)methylidene]-6-oxodecahydroquinoline derivative (XIX) can be prepared by allowing a 6-oxodecahydroquinoline derivative (XVI) to react with Compound (XVII) or Compound (XVIII) in an inert solvent. As the inert solvent used in the reaction, for example, toluene, N,N-dimethylformamide and the like can be illustrated. The reaction temperature is usually at 0° C. to 120°

C., the reaction time is usually 30 minuets to 24 hours, varying based on the starting materials employed, the solvent, the reaction temperature and the like.

Step 1-6

An octahydropyridoquinazoline derivative (I) can be prepared by allowing a 7-[(dimethylamino)methylidene]-6-oxodecahydroquinoline derivative (XIX) to react with a guanidine derivative (XX) in an inert solvent. As the inert solvent used in the reaction, for example, ethanol and the like can be illustrated. The reaction temperature is usually at 0° C. to 180° C., the reaction time is usually 1 hour to 24 hours, varying based on the starting materials employed, the solvent, the reaction temperature and the like.

acid by using a reducing reagent such as sodium cyanoborohydride, sodium borohydride, sodium triacetoxyborohydride or the like. As the solvent used in the reaction, for example, tetrahydrofuran, methanol, ethanol, ethyl acetate, 1,4-dioxane, a mixed solvent thereof and the like can be illustrated. As the acid, for example, sulfuric acid, hydrochloric acid, acetic acid and the like can be illustrated. The reaction temperature is usually at −50° C. to 50° C., the reaction time is usually 10 minuets to 12 hours, varying based on the starting materials employed, the solvent, the reaction temperature and the like.

[Chem.8]

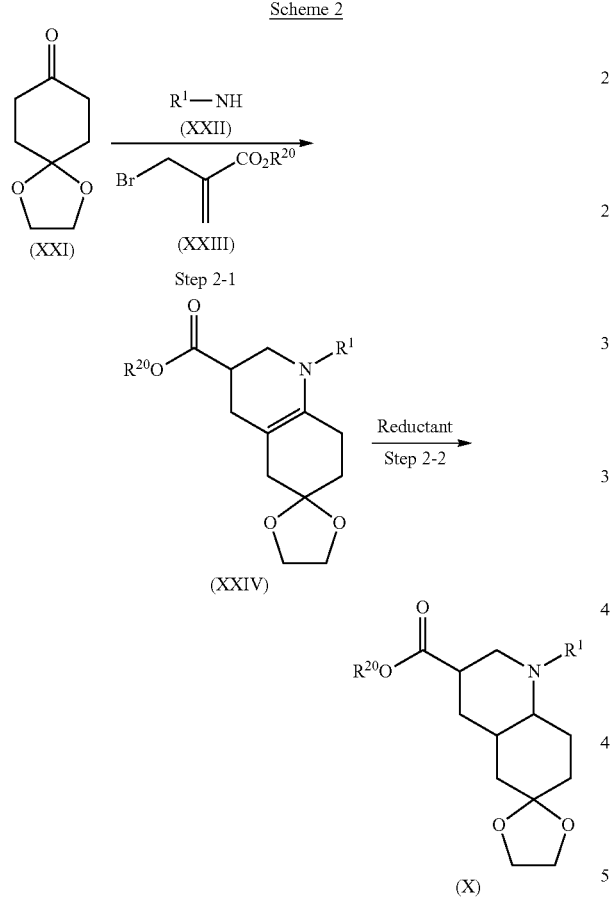

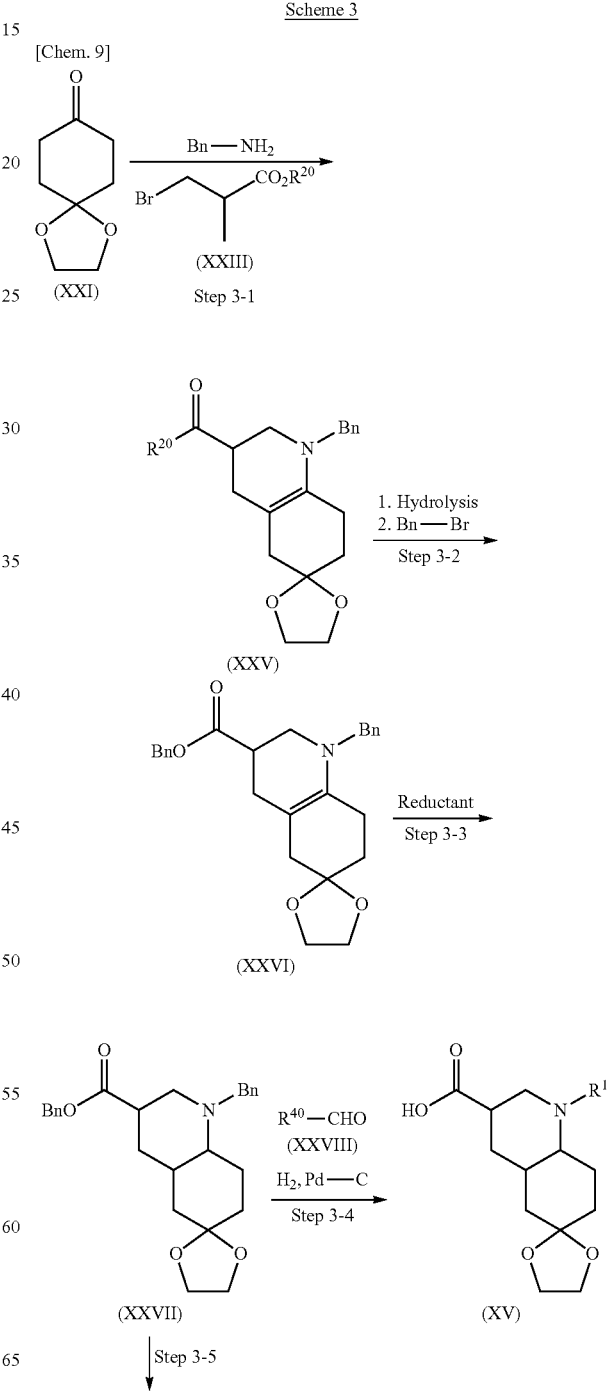

In the formula, $R^1$ and $R^{20}$ have the same meanings as defined above.

Step 2-1

Compound (XXIV) can be prepared by conducting coupling reaction of a 1,4-cyclohexanedione monoethylene ketal (XXI), Amine (XXII) and a (2-bromomethyl)acrylic acid ester (XXIII) in an inert solvent. As the inert solvent used in the reaction, for example, toluene, benzene and the like can be illustrated. The reaction temperature is usually at −50° C. to reflux temperature, the reaction time is usually 1 hour to 24 hours, varying based on the starting materials employed, the solvent, the reaction temperature and the like.

Step 2-2

Compound (X) can be prepared by reduction of Compound (XXIV) in a suitable solvent in the presence of an -continued

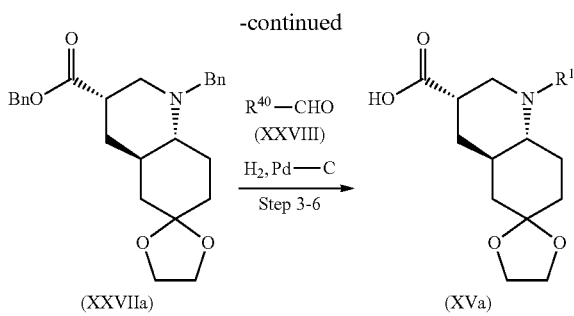

(XXVIIa)  (XVa)

In the formula, $R^1$ and $R^{20}$ have the same meanings as defined above; and Bn is a benzyl group, $R^{40}$ is a $C_{1-6}$ alkyl group.

Step 3-1

Compound (XXV) can be prepared by conducting coupling reaction of a 1,4-cyclohexanedione monoethylene ketal (XXI), a benzyl amine and a 2-(bromomethyl)acrylic acid ester (XXIII) by the same method of step 2-1.

Step 3-2

A carboxylic acid derivative can be prepared by alkaline hydrolysis of Compound (XXV) in a suitable solvent. As the solvent used in the reaction, for example, methanol, ethanol, water, tetrahydrofuran, a mixed solvent thereof and the like can be illustrated. As the base, for example, sodium hydroxide, potassium hydroxide, lithium hydroxide and the like can be illustrated. The reaction temperature is usually at 0° C. to reflux temperature, the reaction time is usually 10 minutes to 24 hours, varying based on the starting materials employed, the solvent, the reaction temperature and the like.

Compound (XXVI) can be prepared by esterification of a carboxylic acid derivative with a benzyl bromide in an inert solvent in the presence of a base. As the inert solvent used in the reaction, for example, acetonitrile, N,N-dimethylformamide, tetrahydrofuran, methylene chloride, a mixed solvent thereof and the like can be illustrated. As the base, for example, potassium carbonate, cesium carbonate and the like can be illustrated. The reaction temperature is usually at −20° C. to 100° C., the reaction time is usually 1 hour to 24 hours, varying based on the starting materials employed, the solvent, the reaction temperature and the like.

Step 3-3

Compound (XXVII) can be prepared by reduction of Compound (XXVI) by the same method of step 2-2.

Step 3-4

A carboxylic acid derivative (XV) can be prepared by allowing Compound (XXVII) to react with Aldehyde (XXVIII) in a suitable solvent under hydrogen atmosphere in the presence of a metal catalyst. As the solvent used in the reaction, for example, methanol, ethanol, N,N-dimethylformamide, tetrahydrofuran, ethyl acetate and the like can be illustrated. As the metal catalyst, for example, palladium-carbon, platinum dioxide and the like can be illustrated. The reaction temperature is usually at room temperature to 80° C., the reaction time is usually 30 minutes to 24 hours, varying based on the starting materials employed, the solvent, the reaction temperature and the like.

Step 3-5

An optical active compound (XXVIIa) can be prepared by allowing Compound (XXVII) to separate by mean of optical resolution by crystallization such as preferential crystallization, diastereomeric salt formation, inclusion complexation, preference enrichment and the like, enzymatic optical resolution or direct optical resolution using a chiral column chromatography.

As the chiral column used in the direct optical resolution by the chiral column chromatography, for example, CHIRALPAK (registered mark) AY-H column, AD-H column, IA column, CHIRALCEL (registered mark) OJ-H column (Daicel Corporation) and the like can be illustrated. As the eluting solvent, hexane, acetonitrile, methanol, ethanol, 2-propanol, diethylamine, a mixed solvent thereof and the like can be illustrated. The eluting flow rate is 0.5 mL/min to 10 mL/min. The eluting temperature is usually at 10° C. to 60° C., and the detection wavelength is 200 nm to 270 nm.

Step 3-6

Compound (XVa) can be prepared by allowing an optical active compound (XXVIIa) to react with Aldehyde (XXVIII) by the same method of Step 3-4.

The forementioned schemes are exemplary for preparing compounds of the present invention and synthetic intermediates thereof. Those ordinarily skilled in the art will appreciate that various changes or modifications of the forementioned schemes may be made without departing from the scope of the invention.

Compounds represented by the general formula (I) of the present invention and intermediates for preparing the compounds of the present invention can be isolated or purified, if required, according to conventional isolation or purification techniques well known to those in the art of the relevant field, such as solvent extraction, crystallization, recrystallization, chromatography, preparative high performance liquid chromatography or the like.

Compounds of the present invention prepared in the above-mentioned schemes exhibit excellent dopamine $D_2$ receptor stimulating activities, and are accordingly useful as a treating or prophylactic agent for the various diseases dopamine $D_2$ receptor mediated. For example, the compounds of the present invention are useful as a treating or prophylactic agent such as Parkinson's disease, restless legs syndrome, hyperprolactinemia or the like, especially useful as a treating or preventing agent of Parkinson's disease.

Compounds of the present invention can be used, if required, in combination with other anti-Parkinson drugs. As the other anti-Parkinson drugs, for example, L-dopa; dopamine D2 receptor agonists such as cabergoline, bromocriptine mesylate, terguride, talipexole hydrochloride, ropinirole hydrochloride, pergolide mesylate, pramipexole hydrochloride, rotigotine, apomorphine and the like; anticholinergic agents such as profenamine, trihexyphenidyl hydrochloride, mazaticol hydrochloride, piperiden, piroheptine hydrochloride, methixene hydrochloride and the like; adenosine $A_{2A}$ receptor antagonists such as istradefylline and the like; NMDA receptor antagonists such as budipine and the like; monoamine oxidase B inhibitors such as selegiline hydrochloride, rasagiline mesylate, safinamide mesylate and the like; COMT inhibitors such as entacapone and the like; aromatic L-amino acid decarboxylase inhibitors such as carbidopa, benserazide and the like; droxidopa, melevodopa, threodops; zonisamide; amantadine hydrochloride and the like can be illustrated.

Pharmaceutical compositions comprising a compound represented by the general formula (I) of the present invention or a pharmaceutically acceptable salt thereof as an active ingredient can be administered in various dosage forms depending on their usages. As such dosage forms, for example, powders, granules, fine granules, dry syrups, tablets, capsules, injections, liquids, ointments, suppositories, poultices and the like can be illustrated, which are administered orally or parenterally.

Pharmaceutical compositions comprising a compound represented by the general formula (I) of the present invention or a pharmaceutically acceptable salt thereof can be prepared by using a compound represented by the general formula (I) of the present invention or a pharmaceutically acceptable salt thereof and at least one of a pharmaceutical additive. These pharmaceutical compositions can be formulated by admixing, diluting or dissolving with appropriate pharmaceutical additives such as excipients, disintegrants, binders, lubricants, diluents, buffers, tonicity agents, preservatives, wetting agents, emulsifying agents, dispersing agents, stabilizing agents, solubilizing agents and the like, according to a conventional formulation procedure depending upon their dosage forms.

The dosage of a compound represented by the general formula (I) or a pharmaceutically acceptable salt thereof is appropriately determined depending on the age, sex, body weight, degree of symptom and treatment of each patient and the like, which is approximately within the range of from about 0.1 mg to about 300 mg per day per adult human, preferably about 0.5 mg to about 30 mg, in the case of oral administration, and approximately within the range of from about 0.01 mg to about 50 mg per day per adult human, preferably about 0.05 mg to about 10 mg, in the case of parenteral administration, the daily dose can be divided into one to several times per day and administered.

A pharmaceutical combination comprising a compound represented by the general formula (I) of the present invention or a pharmaceutically acceptable salt thereof and other anti-Parkinson drugs can be administered as a single pharmaceutical composition comprising together with these active ingredients, or as separately formulated pharmaceutical compositions each of which comprises a single active ingredient. When separately formulated pharmaceutical compositions are used, these compositions can be administered separately or concurrently. Alternatively, where separately formulated pharmaceutical compositions are used, these compositions can be mixed together with an appropriate diluent at the point of use, and administered simultaneously.

A pharmaceutical combination comprising a compound represented by the general formula (I) of the present invention or a pharmaceutically acceptable salt thereof, and any other anti-Perkinson drugs is preferably used for the treating or preventing agent of Parkinson's disease, restless legs syndrome, hyperprolactinemia or the like, especially used for the treating or preventing agent of Parkinson's disease.

In a pharmaceutical combination comprising a compound represented by the general formula (I) or a pharmaceutically acceptable salt thereof and other anti-Parkinson drugs, the compounding ratio of medicament can be appropriately determined depending on the age, sex or body weight of the individual patient, the severity of the disease, administration time, dosage form, administration method, combination of medicaments and the like.

The present invention is further illustrated in more detail by way of the following Reference Examples, Examples and Test Examples. However, the present invention is not limited thereto.

EXAMPLES

Reference Example 1-1

Ethyl 1'-propyl-2',3',4',5',7',8'-hexahydro-1'H-spiro [1,3-dioxolane-2, 6'-quinoline]-3'-carboxylate To a mixture of ethyl 2-(bromomethyl)acrylate (20.77 g) and toluene (320 mL) was added dropwise a mixture of a 1-propylamine (22 mL) and toluene (80 mL) while stirring under ice bath cooling, and stirred for 14 minutes. To the mixture was added a mixture of 1,4-cyclohexandione monoethylene ketal (14.00 g) and toluene (100 mL) under the same conditions, and the mixture was refluxed with the Dean-Stark apparatus for 4.5 hours. After cooling to room temperature, the mixture was filtrated insoluble materials, and the filtrate was concentrated under reduced pressure. The residue was purified by aminopropyl silica gel column chromatography (eluent: 0%-30% ethyl acetate/hexane, gradient elution) to give the title compound (26.17 g). The structure was illustrated in Table 1.

$^1$H-NMR (CDCl$_3$) δ ppm: 0.86 (3H, t, J=7.4 Hz), 1.26 (3H, t, J=7.1 Hz), 1.35-1.60 (2H, m), 1.70-1.90 (2H, m), 1.90-2.05 (1H, m), 2.10-2.40 (5H, m), 2.65-2.90 (3H, m), 2.90-3.05 (1H, m), 3.15-3.25 (1H, m), 3.90-4.05 (4H, m), 4.14 (2H, q, J=7.1 Hz)

Reference example 1-2 was prepared in a manner similar to those as described in reference example 1-1 using a benzylamine instead of a 1-propylamine. The structure was illustrated in Table 1.

$^1$H-NMR (CDCl$_3$) δ ppm: 1.15-1.35 (4H, m), 1.80-1.90 (2H, m), 1.95-2.10 (1H, m), 2.15-2.50 (5H, m), 2.65-2.80 (1H, m), 2.90-3.00 (1H, m), 3.05-3.20 (1H, m), 3.90-4.20 (7H, m), 7.20-7.40 (5H, m)

Reference Example 2-1

Benzyl 1'-benzyl-2',3',4',5',7',8'-hexahydro-1'H-spiro [1,3-dioxolane-2, 6'-quinoline]-3'-carboxylate To a mixture of ethyl 1'-benzyl-2',3',4',5',7',8'-hexahydro-1'H-spiro[1,3-dioxolane-2,6'-quinoline]-3'-carboxylate (reference example 1-2) (34.82 g) and ethanol (487 mL) was added a 5 mol/L aqueous solution of sodium hydroxide (27.0 mL) while stirring at room temperature, and the mixture was stirred for 1 hour at 80° C. After cooling in ice bath, it was neutralized by the addition of 6 mol/L hydrochloric acid (22.5 mL). The mixture was concentrated under reduced pressure to give 1'-benzyl-2',3',4',5',7',8'-hexahydro-1'H-spiro[1,3-dioxolane-2,6'-quinoline]-3'-carboxylic acid.

To a mixture of 1'-benzyl-2',3',4',5',7',8'-hexahydro-1'H-spiro[1,3-dioxolane-2,6'-quinoline]-3'-carboxylic acid and N,N-dimethylformamide (244 mL) was added potassium carbonate (21.54 g), followed by benzylbromide (13.90 mL), and the mixture was stirred at room temperature for 14 hours. To the reaction mixture was added dimethylamine (12.09 mL), and stirred at room temperature for 1 hour. Water was added to the reaction mixture, and extracted with ethyl acetate. After the separated organic layer was dried over anhydrous sodium sulfate, it was concentrated under reduced pressure. The residue was purified by aminopropyl silica gel column chromatography (eluent: 0%-35% ethyl acetate/hexane, gradient elution) to give the title compound (30.28 g). The structure was illustrated in Table 1.

$^1$H-NMR (CDCl$_3$) δ ppm: 1.75-1.90 (2H, m), 2.00-2.15 (1H, m), 2.15-2.55 (5H, m), 2.70-2.85 (1H, m), 2.95-3.05 (1H, m), 3.10-3.20 (1H, m), 3.90-4.05 (5H, m), 4.10 (1H, d, J=15.7 Hz), 5.08 (2H, dd, J=22.5, 12.5 Hz), 7.20-7.40 (10H, m)

TABLE 1

| Reference example | Structure |
|---|---|
| 1-1 | 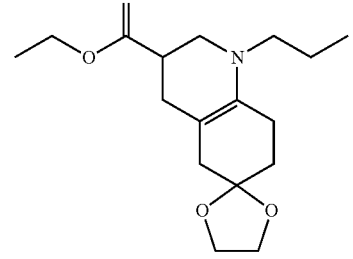 |
| 1-2 | 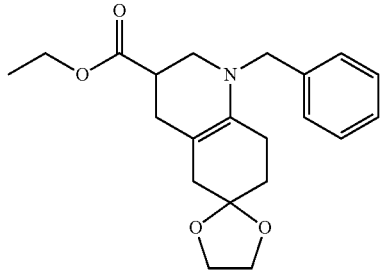 [SMILES: CCOC(=O)C1CC2=C(CCC3(C2)OCCO3)N(Cc2ccccc2)C1] |
| 2-1 | 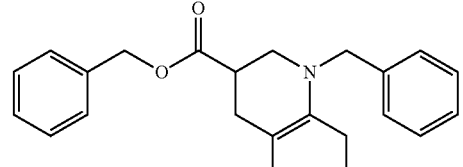 |

Reference Example 3-1

Ethyl(3'S*,4'aR*,8'aR*)-1'-propyloctahydro-1'H-spiro[1,3-dioxolane-2, 6'-quinoline]-3'-carboxylate To a mixture of ethyl 1'-propyl-2',3',4',5',7',8'-hexahydro-1'H-spiro[1,3-dioxolane-2,6'-quinoline]-3'-carboxylate (reference example 1-1) (11.87 g), tetrahydrofuran (135 mL) and methanol (45 mL) was added a 4 mol/L hydrogen chloride-dioxane solution (10.1 mL), followed by sodium cyanoborohydride (7.24 g) while stirring under ice bath cooling, and the mixture was stirred for 1.5 hours. A saturated aqueous solution of sodium bicarbonate was added to the reaction mixture, and extracted with ethyl acetate. After the separated organic layer was dried over anhydrous sodium sulfate, it was concentrated under reduced pressure. The residue was purified by aminopropyl silica gel column chromatography (eluent: 5%-40% ethyl acetate/hexane, gradient elution) to give the crude product. The crude product was purified by silica gel column chromatography (eluent: 0%-10% methanol/ethyl acetate, gradient elution) to give the title compound (2.34 g). The structure was illustrated in Table 2.
$^1$H-NMR (CDCl$_3$) δ ppm: 0.83 (3H, t, J=7.4 Hz), 1.05-1.20 (1H, m), 1.20-1.30 (4H, m), 1.30-1.60 (4H, m), 1.60-1.90 (4H, m), 1.95-2.15 (2H, m), 2.15-2.35 (2H, m), 2.50-2.70 (2H, m), 3.35-3.45 (1H, m), 3.85-4.00 (4H, m), 4.05-4.25 (2H, m)

Reference examples 3-2 to 3-3 were prepared in a manner similar to those as described in reference example 3-1 using the corresponding enamines instead of ethyl 1'-propyl-2',3',4',5',7',8'-hexahydro-1'H-spiro[1,3-dioxolane-2,6'-quinoline]-3'-carboxylate. These were illustrated in Table 2.

TABLE 2

| Reference example | Structure |
|---|---|
| 3-1 | 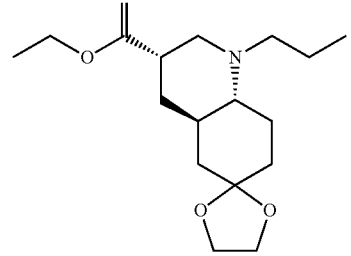 |
| 3-2 | 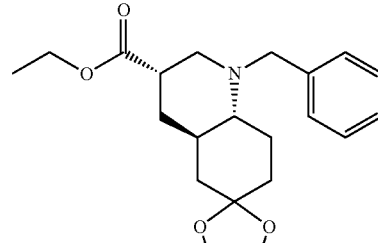 |
| 3-3 | 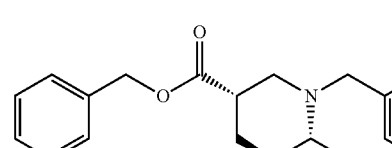 |

The structures of the reference example 3-1 to 3-3 in Table 2 indicate relative configuration.

The physical data of reference examples 3-2 to 3-3 were shown below.

Reference Example 3-2

$^1$H-NMR (CDCl$_3$) δ ppm: 1.10-1.25 (4H, m), 1.30 (1H, t, J=12.9 Hz), 1.35-1.65 (2H, m), 1.65-1.75 (1H, m), 1.75-1.85 (2H, m), 1.90-2.20 (4H, m), 2.45-2.55 (1H, m), 3.04 (1H, d, J=13.8 Hz), 3.25-3.35 (1H, m), 3.85-4.20 (7H, m), 7.15-7.40 (5H, m)

Reference Example 3-3

$^1$H-NMR (CDCl$_3$) δ ppm: 1.10-1.25 (1H, m), 1.31 (1H, t, J=12.8 Hz), 1.35-1.65 (2H, m), 1.65-1.75 (1H, m), 1.75-1.90 (2H, m), 1.95-2.25 (4H, m), 2.55-2.65 (1H, m), 3.10 (1H, d, J=13.9 Hz), 3.30-3.40 (1H, m), 3.85-4.00 (4H, m), 4.09 (1H, d, J=13.9 Hz), 4.95 (1H, d, J=12.6 Hz), 5.21 (1H, d, H=12.6 Hz), 7.10-7.35 (10H, m)

Reference Example 4-1

Benzyl(3'S,4'aR,8'aR)-1'-benzyloctahydro-1'H-spiro[1,3-dioxolane-2,6'-quinoline]-3'-carboxylate Benzyl(3'S*,4'aR*,8'aR*)-1'-benzyloctahydro-1'H-spiro[1,3-dioxolane-2,6'-quinoline]-3'-carboxylate (reference example 3-3) (36.0 g) was repeated chromatography using a CHIRALCEL (registered mark) OJ-H (Daicel corporation) column (250 mm×100 mm I.D.) with the following condition:
Solvent system; methanol:acetonitrile:diethylamine=90:10:0.05 (V/V/V)
Detection wavelength; 215 nm
Flow rate; 1.0 mL/min
Column oven temperature; 40° C.

The eluted component of the first peak was collected, and concentrated to give the title compound (17.3 g).
$^1$H-NMR (CDCl$_3$) δ ppm: 1.10-1.25 (1H, m), 1.31 (1H, t, J=12.8 Hz), 1.40-1.65 (2H, m), 1.65-1.75 (1H, m), 1.75-1.90 (2H, m), 1.95-2.25 (4H, m), 2.55-2.65 (1H, m), 3.10 (1H, d, J=13.9 Hz), 3.30-3.40 (1H, m), 3.85-4.00 (4H, m), 4.09 (1H, d, J=13.9 Hz), 4.95 (1H, d, J=12.6 Hz), 5.22 (1H, d, H=12.6 Hz), 7.10-7.35 (10H, m) $[α]_D^{25}$=−53.393° (c=1.01, CHCl$_3$)

Reference Example 5-1

(3'S,4'aR,8'aR)-1'-Propyloctahydro-1'H-spiro[1,3-dioxolane-2,6'-quinoline]-3'-carboxylic acid To a mixture of benzyl(3'S,4'aR,8'aR)-1'-benzyloctahydro-1'H-spiro[1,3-dioxolane-2,6'-quinoline]-3'-carboxylate (reference example 4-1) (3.20 g), tetrahydrofuran (38 mL) and methanol (38 mL) was added propionaldehyde (1.65 mL), followed by 10% palladium-carbon (0.64 g), the mixture was stirred at room temperature for 3 hours under a hydrogen atmosphere. The mixture was passed through a layer of Celite (registered mark), the filtrate was concentrated under reduced pressure. To the residue was added toluene, and concentrated under reduced pressure to give the title compound (2.36 g). The structure was illustrated in Table 3.
$^1$H-NMR (CDCl$_3$) δ ppm: 0.92 (3H, t, J=7.3 Hz), 1.20-1.45 (2H, m), 1.45-1.75 (5H, m), 1.80-1.90 (1H, m), 1.90-2.15 (4H, m), 2.50-2.70 (2H, m), 2.70-2.85 (2H, m), 3.15-3.25 (1H, m), 3.85-4.00 (4H, m)

Reference Example 5-2

(3'S*,4'aR*,8'aR*)-1'-Propyloctahydro-1'H-spiro[1,3-dioxolane-2,6'-quinoline]-3'-carboxylic acid To a mixture of benzyl(3'S*,4'aR*,8'aR*)-1'-benzyloctahydro-1'H-spiro[1,3-dioxolane-2,6'-quinoline]-3'-carboxylate (reference example 3-3) (6.26 g), and ethanol (297 mL) was added propionaldehyde (10.72 mL), followed by 10% palladium-carbon (1.23 g), the mixture was stirred at room temperature for 7 hours under a hydrogen atmosphere. This suspension was passed through a layer of Celite (registered mark), the filtrate was concentrated under reduced pressure. The residue was triturated with diethyl ether to give the title compound (3.75 g). The structure was illustrated in Table 3.
$^1$H-NMR (CDCl$_3$) δ ppm: 0.93 (3H, t, J=7.4 Hz), 1.25-1.45 (2H, m), 1.45-1.75 (5H, m), 1.80-1.90 (1H, m), 1.90-2.15 (4H, m), 2.50-2.70 (2H, m), 2.70-2.85 (2H, m), 3.15-3.25 (1H, m), 3.85-4.00 (4H, m)

TABLE 3

| Reference example | Structure |
|---|---|
| 5-1 | Chiral structure shown |
| 5-2 | Structure shown |

The structure of the reference example 5-1 in Table 3 indicates absolute configuration, and the structure of the reference example 5-2 indicates relative configuration.

Reference Example 6-1

(3'S*,4'aR*,8'aR*)-1'-Propyloctahydro-1'H-spiro[1,3-dioxolane-2,6'-quinoline]-3'-carbohydrazide A mixture of ethyl(3'S*,4'aR*,8'aR*)-1'-propyloctahydro-1'H-spiro[1,3-dioxolane-2,6'-quinoline]-3'-carboxylate (reference example 3-1) (1.29 g) and hydrazine anhydride (2.8 mL) was stirred at 100° C. for 24 hours. The reaction mixture was concentrated under reduced pressure. The residue was purified by aminopropyl silica gel column chromatography (eluent: 0%-10% methanol/ethyl acetate, gradient elution) to give the title compound (1.08 g). The structure was illustrated in Table 4.
$^1$H-NMR (CDCl$_3$) δ ppm: 0.88 (3H, t, J=7.4 Hz), 1.22-1.37 (2H, m), 1.38-1.76 (6H, m), 1.77-1.93 (3H, m), 2.01-2.12 (1H, m), 2.28-2.42 (2H, m), 2.55-2.62 (1H, m), 2.63-2.76 (1H, m), 3.04-3.13 (1H, m), 3.79-4.01 (6H, m), 9.51-9.64 (1H, m)

Reference Example 6-2 was prepared in a manner similar to those as described in reference example 6-1 using the corresponding ethyl(3'S*,4'aR*,8'aR*)-1'-benzyloctahydro-1'H-spiro[1,3-dioxolane-2,6'-quinoline]-3'-carboxylate (reference example 3-2) instead of ethyl(3'S*,4'aR*,8'aR*)-1'-propyloctahydro-1'H-spiro[1,3-dioxolane-2,6'-quinoline]-3'-carboxylate. The structure was illustrated in Table 4.
$^1$H-NMR (CDCl$_3$) δ ppm: 1.25-1.40 (2H, m), 1.50-1.70 (3H, m), 1.70-1.95 (4H, m), 2.05-2.20 (1H, m), 2.20-2.40 (1H, m), 2.45-2.55 (1H, m), 2.90-3.05 (2H, m), 3.65-3.85 (2H, m), 3.85-4.00 (4H, m), 4.20-4.30 (1H, m), 7.20-7.40 (5H, m), 9.10-9.25 (1H, m)

TABLE 4

| Reference example | Structure |
|---|---|
| 6-1 | (structure: H₂N-NH-C(=O)- attached to propyl-substituted octahydrospiro[1,3-dioxolane-2,6'-quinoline]) |
| 6-2 | (structure: H₂N-NH-C(=O)- attached to benzyl-substituted octahydrospiro[1,3-dioxolane-2,6'-quinoline]) |

The structures of the reference example 6-1 to 6-2 in Table 6 indicate relative configuration.

Reference Example 7-13

[(3'S*,4'aR*,8'aR*)-1'-Propyloctahydro-1'H-spiro[1,3-dioxolane-2,6'-quinolin]-3'-yl]-1,1-diethylurea To a mixture of (3'S*,4'aR*,8'aR*)-1'-propyloctahydro-1'H-spiro[1,3-dioxolane-2,6'-quinoline]-3'-carbohydrazide (reference example 6-1) (573 mg) and 0.2 mol/L of hydrochloric acid (24 mL) was added a mixture of a sodium nitrite (140 mg) and water (2 mL) while stirring under ice bath cooling, and the mixture was stirred for 1 hour. A saturated aqueous solution of sodium bicarbonate was added to the reaction mixture, and extracted with ethyl acetate. After the separated organic layer was dried over anhydrous sodium sulfate, toluene was added, and ethyl acetate was removed under reduced pressure to give a toluene solution of (3'S*,4'aR*,8'aR*)-1'-propyloctahydro-1H'-spiro[1,3-dioxolane-2,6-'quinoline]-3'-carbonyl azide.

The toluene solution of (3'S*,4'aR*,8'aR*)-1'-propyloctahydro-1H'-spiro[1,3-dioxolane-2,6-'quinoline]-3'-carbonyl azide was refluxed for 1 hour. To the reaction mixture was added diethylamine (0.598 mL), and stirred at 50° C. for 40 minuets. After cooling to room temperature, water and ethyl acetate were added, and extracted with ethyl acetate. After the separated organic layer was dried over anhydrous sodium sulfate, it was concentrated under reduced pressure. The residue was purified by silica gel column chromatography (eluent: 0%-15% methanol/ethyl acetate, gradient elution) to give the title compound (412 mg).

¹H-NMR (CDCl₃) δ ppm: 0.85 (3H, t, J=7.3 Hz), 1.08-1.23 (1H, m), 1.14 (6H, t, J=7.2 Hz), 1.27-1.87 (10H, m), 2.00-2.12 (1H, m), 2.19-2.31 (1H, m), 2.33-2.40 (1H, m), 2.58-2.70 (1H, m), 2.75-2.85 (1H, m), 3.26 (4H, q, J=7.2 Hz), 3.89-3.97 (4H, m), 3.98-4.05 (1H, m), 5.39 (1H, d, J=8.0 Hz)

Reference examples 7-2 to 7-27 were prepared in a manner similar to those as described in reference example 7-1 using the corresponding carbohydrazides and amines instead of (3'S*,4'aR*,8'aR*)-1'-propyloctahydro-1'H-spiro[1,3-dioxolane-2,6'-quinoline]-3'-carbohydrazide and diethylamine. These were illustrated in Table 5.

TABLE 5

| Reference example | Structure |
|---|---|
| 7-1 | (N,N-diethylurea derivative of propyl-substituted octahydrospiro[1,3-dioxolane-2,6'-quinoline]) |
| 7-2 | (N-benzyl-N-methylurea derivative of propyl-substituted octahydrospiro[1,3-dioxolane-2,6'-quinoline]) |
| 7-3 | (N,N-dimethylurea derivative of propyl-substituted octahydrospiro[1,3-dioxolane-2,6'-quinoline]) |
| 7-4 | (N-butyl-N-methylurea derivative of propyl-substituted octahydrospiro[1,3-dioxolane-2,6'-quinoline]) |

TABLE 5-continued

| Reference example | Structure |
|---|---|
| 7-5 | 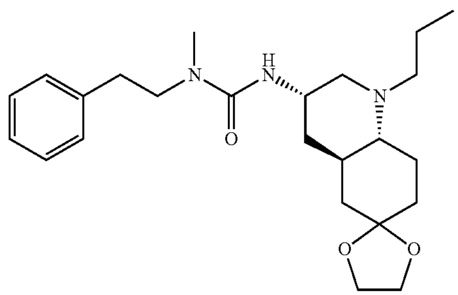 [SMILES: CCCN1C[C@@H](NC(=O)N(C)CCc2ccccc2)C[C@@H]2CC3(CC[C@H]21)OCCO3] |
| 7-6 | 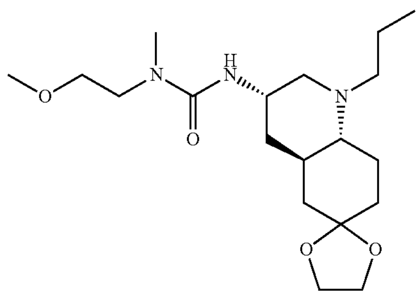 [SMILES: CCCN1C[C@@H](NC(=O)N(C)CCOC)C[C@@H]2CC3(CC[C@H]21)OCCO3] |
| 7-7 | 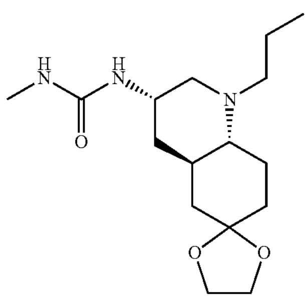 [SMILES: CCCN1C[C@@H](NC(=O)NC)C[C@@H]2CC3(CC[C@H]21)OCCO3] |
| 7-8 | 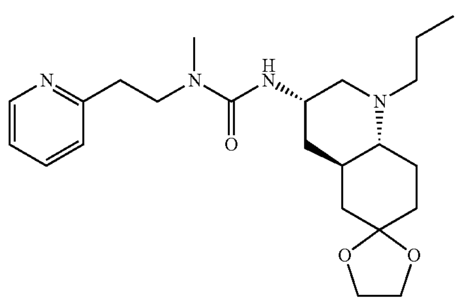 [SMILES: CCCN1C[C@@H](NC(=O)N(C)CCc2ccccn2)C[C@@H]2CC3(CC[C@H]21)OCCO3] |
| 7-9 | 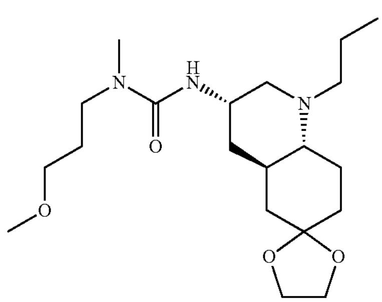 [SMILES: CCCN1C[C@@H](NC(=O)N(C)CCCOC)C[C@@H]2CC3(CC[C@H]21)OCCO3] |
| 7-10 | |
| 7-11 | |
| 7-12 | |
| 7-13 | |
| 7-14 | |

TABLE 5-continued

| Reference example | Structure |
|---|---|
| 7-15 | 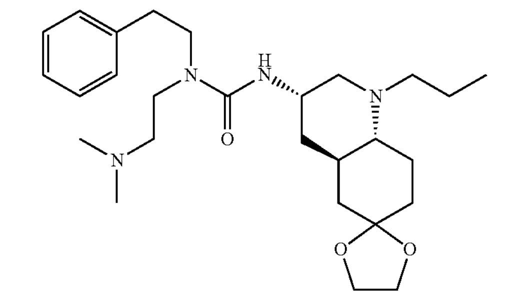 [SMILES: CCCN1C[C@@H](NC(=O)N(CCc2ccccc2)CCN(C)C)C[C@@H]2CC3(CC[C@H]21)OCCO3] |
| 7-16 | 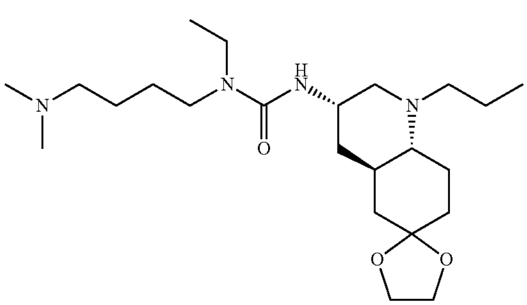 [SMILES: CCCN1C[C@@H](NC(=O)N(CC)CCCCN(C)C)C[C@@H]2CC3(CC[C@H]21)OCCO3] |
| 7-17 | 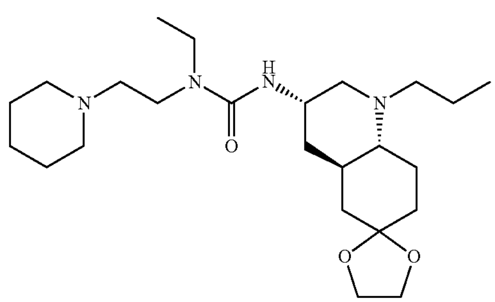 [SMILES: CCCN1C[C@@H](NC(=O)N(CC)CCN2CCCCC2)C[C@@H]2CC3(CC[C@H]21)OCCO3] |
| 7-18 | 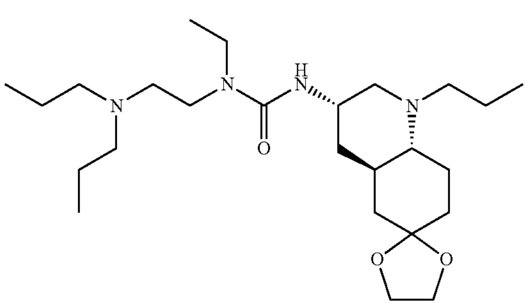 [SMILES: CCCN(CCC)CCN(CC)C(=O)N[C@H]1C[C@@H]2CC3(CC[C@H]2N(CCC)C1)OCCO3] |
| 7-19 | 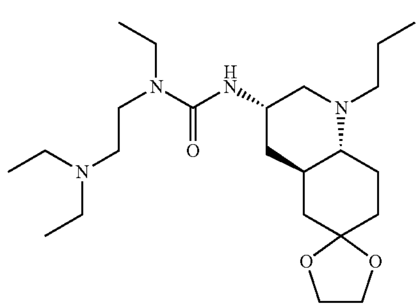 [SMILES: CCCN1C[C@@H](NC(=O)N(CC)CCN(CC)CC)C[C@@H]2CC3(CC[C@H]21)OCCO3] |
| 7-20 | |
| 7-21 | |
| 7-22 | |
| 7-23 | |
| 7-24 | |

TABLE 5-continued

| Reference example | Structure |
|---|---|
| 7-25 | 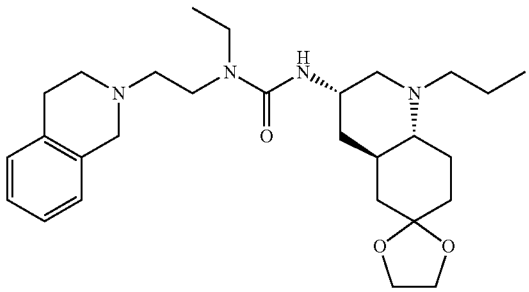 [SMILES: CCCN1C[C@@H](NC(=O)N(CC)CCN2CCc3ccccc3C2)C[C@@H]2CC3(CC[C@H]21)OCCO3] |
| 7-26 | 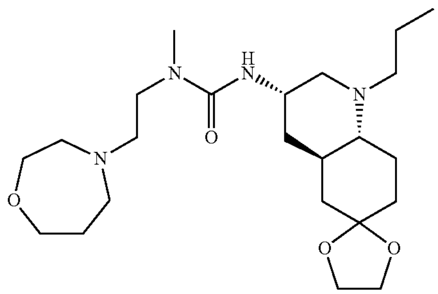 [SMILES: CCCN1C[C@@H](NC(=O)N(C)CCN2CCCOCC2)C[C@@H]2CC3(CC[C@H]21)OCCO3] |
| 7-27 | 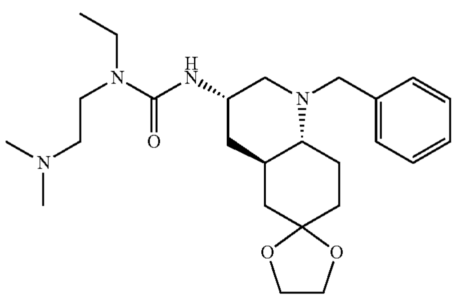 [SMILES: CCN(CCN(C)C)C(=O)N[C@H]1C[C@@H]2CC3(CC[C@H]2N(Cc2ccccc2)C1)OCCO3] |

The structures of the reference example 7-1 to 7-27 in Table 5 indicate relative configuration.

The physical data of reference examples 7-2 to 7-27 were shown below.

Reference Example 7-2

¹H-NMR (CDCl₃) δ ppm: 0.79 (3H, t, J=7.5 Hz), 1.11-1.23 (1H, m), 1.23-1.42 (4H, m), 1.48-1.67 (3H, m), 1.70-1.85 (3H, m), 1.94-2.05 (1H, m), 2.17-2.29 (1H, m), 2.30-2.41 (1H, m), 2.49-2.62 (1H, m), 2.71-2.81 (1H, m), 2.89 (3H, s), 3.90-3.98 (4H, m), 3.99-4.06 (1H, m), 4.34-4.63 (2H, m), 5.47 (1H, d, J=8.0 Hz), 7.21-7.29 (3H, m), 7.30-7.37 (2H, m)

Reference Example 7-3

¹H-NMR (CDCl₃) δ ppm: 0.84 (3H, t, J=7.4 Hz), 1.12-1.23 (1H, m), 1.27-1.47 (4H, m), 1.51-1.86 (6H, m), 2.00-2.10 (1H, m), 2.23-2.33 (1H, m), 2.34-2.41 (1H, m), 2.57-2.69 (1H, m), 2.75-2.83 (1H, m), 2.90 (6H, s), 3.89-4.03 (5H, m), 5.41 (1H, d, J=8.0 Hz)

Reference Example 7-4

¹H-NMR (CDCl₃) δ ppm: 0.85 (3H, t, J=7.3 Hz), 0.94 (3H, t, J=7.3 Hz), 1.11-1.23 (1H, m), 1.26-1.46 (6H, m), 1.46-1.73 (5H, m), 1.74-1.85 (3H, m), 2.00-2.10 (1H, m), 2.20-2.32 (1H, m), 2.32-2.41 (1H, m), 2.57-2.69 (1H, m), 2.74-2.83 (1H, m), 2.87 (3H, s), 3.11-3.33 (2H, m), 3.88-4.04 (5H, m), 5.39 (1H, d, J=8.0 Hz)

Reference Example 7-5

¹H-NMR (CDCl₃) δ ppm: 0.84 (3H, t, J=7.3 Hz), 1.13-1.23 (1H, m), 1.28-1.48 (4H, m), 1.51-1.87 (6H, m), 2.00-2.10 (1H, m), 2.25-2.35 (1H, m), 2.35-2.43 (1H, m), 2.57-2.69 (1H, m), 2.73-2.89 (3H, m), 2.83 (3H, s), 3.37-3.55 (2H, m), 3.90-4.04 (5H, m), 5.40 (1H, d, J=8.3 Hz), 7.17-7.36 (5H, m)

Reference Example 7-6

¹H-NMR (CDCl₃) δ ppm: 0.85 (3H, t, J=7.5 Hz), 1.10-1.23 (1H, m), 1.24-1.47 (4H, m), 1.51-1.85 (6H, m), 2.00-2.10 (1H, m), 2.23-2.33 (1H, m), 2.33-2.40 (1H, m), 2.57-2.68 (1H, m), 2.76-2.83 (1H, m), 2.93 (3H, s), 3.26-3.37 (1H, m), 3.38 (3H, s), 3.45-3.55 (3H, m), 3.87-4.00 (5H, m), 5.85 (1H, d, J=8.3 Hz)

Reference Example 7-7

¹H-NMR (CDCl₃) δ ppm: 0.83 (3H, t, J=7.3 Hz), 1.10-1.45 (5H, m), 1.50-1.85 (6H, m), 2.00-2.10 (1H, m), 2.30-2.45 (2H, m), 2.50-2.65 (1H, m), 2.70-2.85 (4H, m), 3.90-4.05 (5H, m), 4.15-4.30 (1H, m), 5.27 (1H, d, J=8.3 Hz)

Reference Example 7-8

MS (ESI, m/z): 417 (M+H)+

Reference Example 7-9

¹H-NMR (CDCl₃) δ ppm: 0.84 (3H, t, J=7.3 Hz), 1.12-1.23 (1H, m), 1.27-1.46 (4H, m), 1.50-1.62 (2H, m), 1.62-1.85 (6H, m), 1.99-2.10 (1H, m), 2.24-2.34 (1H, m), 2.34-2.42 (1H, m), 2.56-2.68 (1H, m), 2.75-2.84 (1H, m), 2.88 (3H, s), 3.23-3.45 (4H, m), 3.34 (3H, s), 3.89-4.04 (5H, m), 5.49 (1H, d, J=7.8 Hz)

Reference Example 7-10

MS (ESI, m/z): 352 (M+H)+

Reference Example 7-11

¹H-NMR (CDCl₃) δ ppm: 0.83 (3H, t, J=7.3 Hz), 1.05 (6H, t, J=7.2 Hz), 1.13-1.47 (5H, m), 1.50-1.88 (6H, m), 1.98-2.09 (1H, m), 2.31-2.45 (2H, m), 2.49-2.64 (7H, m), 2.74-2.83 (1H, m), 2.90 (3H, s), 3.13-3.43 (2H, m), 3.86-4.02 (5H, m), 6.11-6.31 (1H, m)

Reference Example 7-12

¹H-NMR (CDCl₃) δ ppm: 0.85 (3H, t, J=7.5 Hz), 1.15-1.25 (1H, m), 1.30-1.47 (4H, m), 1.51-1.73 (3H, m), 1.73-1.86 (3H, m), 1.95-2.10 (3H, m), 2.25-2.35 (1H, m), 2.36-2.43 (1H, m), 2.57-2.70 (1H, m), 2.75-2.85 (1H, m), 2.84

(3H, s), 3.23-3.46 (2H, m), 3.90-4.04 (7H, m), 5.44 (1H, d, J=8.0 Hz), 6.96-7.00 (1H, m), 7.03-7.09 (1H, m), 7.51 (1H, s)

Reference Example 7-13

MS (ESI, m/z): 397 (M+H)+

Reference Examples 7-14

MS (ESI, m/z): 459 (M+H)+

Reference Example 7-15

$^1$H-NMR (CDCl$_3$) δ ppm: 0.83 (3H, t, J=7.4 Hz), 1.15-1.50 (5H, m), 1.50-1.65 (2H, m), 1.65-1.90 (4H, m), 2.00-2.10 (1H, m), 2.25 (6H, s), 2.30-2.50 (4H, m), 2.50-2.65 (1H, m), 2.75-2.95 (3H, m), 3.10-3.25 (1H, m), 3.25-3.60 (3H, m), 3.85-4.05 (5H, m), 6.78 (1H, br), 7.15-7.35 (5H, m)

Reference Example 7-16

$^1$H-NMR (CDCl$_3$) δ ppm: 0.85 (3H, t, J=7.3 Hz), 1.10-1.25 (4H, m), 1.25-1.85 (14H, m), 2.00-2.10 (1H, m), 2.15-2.40 (10H, m), 2.55-2.70 (1H, m), 2.75-2.85 (1H, m), 3.15-3.30 (4H, m), 3.85-4.05 (5H, m), 5.41 (1H, d, J=8.1 Hz)

Reference Example 7-17

MS (ESI, m/z): 437 (M+H)+

Reference Example 7-18

MS (ESI, m/z): 453 (M+H)+

Reference Example 7-19

$^1$H-NMR (CDCl$_3$) δ ppm: 0.83 (3H, t, J=7.3 Hz), 1.05 (6H, t, J=7.2 Hz), 1.10-1.90 (14H, m), 1.95-2.10 (1H, m), 2.30-2.45 (2H, m), 2.45-2.70 (7H, m), 2.75-2.85 (1H, m), 3.10-3.45 (4H, m), 3.85-4.05 (5H, m), 6.25-6.50 (1H, m)

Reference Example 7-20

$^1$H-NMR (CDCl$_3$) δ ppm: 0.84 (3H, t, J=7.3 Hz), 1.10-1.85 (15H, m), 2.00-2.10 (1H, m), 2.25-2.70 (15H, m), 2.75-2.85 (1H, m), 3.20-3.45 (4H, m), 3.85-4.05 (5H, m), 5.52 (1H, d, J=8.3 Hz)

Reference Example 7-21

$^1$H-NMR (CDCl$_3$) δ ppm: 0.84 (3H, t, J=7.2 Hz), 1.02 (6H, t, J=7.2 Hz), 1.10-1.22 (1H, m), 1.14 (3H, t, J=7.2 Hz), 1.23-1.50 (4H, m), 1.50-1.90 (8H, m), 2.00-2.10 (1H, m), 2.20-2.33 (1H, m), 2.33-2.48 (3H, m), 2.48-2.71 (5H, m), 2.76-2.86 (1H, m), 3.10-3.40 (4H, m), 3.85-3.96 (4H, m), 3.96-4.05 (1H, m), 5.44 (1H, d, J=8.0 Hz)

Reference Example 7-22

$^1$H-NMR (CDCl$_3$) δ ppm: 0.84 (3H, t, J=7.2 Hz), 1.14 (3H, t, J=7.2 Hz), 1.17-1.50 (6H, m), 1.50-1.62 (2H, m), 1.63-1.90 (7H, m), 1.95-2.10 (1H, m), 2.20-2.35 (1H, m), 2.35-2.45 (1H, m), 2.50-2.70 (7H, m), 2.75-2.85 (1H, m), 3.15-3.45 (4H, m), 3.85-3.97 (4H, m), 3.97-4.05 (1H, m), 5.73 (1H, d, J=8.0 Hz)

Reference Example 7-23

$^1$H-NMR (CDCl$_3$) δ ppm: 0.83 (3H, t, J=7.3 Hz), 1.10 (3H, t, J=7.2 Hz), 1.15-1.25 (1H, m), 1.25-1.50 (4H, m), 1.50-1.65 (2H, m), 1.65-1.85 (4H, m), 2.00-2.10 (1H, m), 2.20-2.45 (2H, m), 2.55-2.70 (1H, m), 2.75-2.85 (1H, m), 3.00-3.10 (2H, m), 3.15-3.30 (2H, m), 3.50-3.70 (2H, m), 3.85-4.05 (5H, m), 5.53 (1H, d, J=8.0 Hz), 7.10-7.15 (1H, m), 7.20-7.25 (1H, m), 7.55-7.65 (1H, m), 8.50-8.60 (1H, m)

Reference Example 7-24

$^1$H-NMR (CDCl$_3$) δ ppm: 0.84 (3H, t, J=7.2 Hz), 1.13 (3H, t, J=7.2 Hz), 1.16-1.48 (5H, m), 1.50-1.90 (14H, m), 1.95-2.10 (1H, m), 2.20-2.45 (2H, m), 2.50-2.85 (8H, m), 3.15-3.40 (4H, m), 3.85-3.95 (4H, m), 3.95-4.05 (1H, m), 5.853 (1H, d, J=8.0 Hz)

Reference Example 7-25

$^1$H-NMR (CDCl$_3$) δ ppm: 0.82 (3H, t, J=7.2 Hz), 1.10-1.45 (5H, m), 1.16 (3H, t, J=6.8 Hz), 1.45-1.85 (6H, m), 1.90-2.10 (1H, m), 2.20-2.34 (1H, m), 2.34-2.42 (1H, m), 2.50-2.62 (1H, m), 2.64-2.94 (7H, m), 3.19-3.55 (4H, m), 3.70-3.75 (2H, m), 3.85-4.05 (5H, m), 5.765 (1H, d, J=8.0 Hz), 6.95-7.20 (4H, m)

Reference Example 7-26

$^1$H-NMR (CDCl$_3$) δ ppm: 0.84 (3H, t, J=7.5 Hz), 1.10-1.50 (5H, m), 1.50-1.95 (8H, m), 2.00-2.10 (1H, m), 2.25-2.45 (2H, m), 2.55-2.75 (3H, m), 2.75-2.85 (5H, m), 2.90 (3H, s), 3.25-3.45 (2H, m), 3.70-3.85 (4H, m), 3.85-4.05 (5H, m), 5.69 (1H, d, J=8.3 Hz)

Reference Example 7-27

$^1$H-NMR (CDCl$_3$) δ ppm: 1.10 (3H, t, J=7.2 Hz), 1.15-1.40 (2H, m), 1.40-1.95 (7H, m), 2.10-2.50 (10H, m), 2.70-2.80 (1H, m), 3.05-3.40 (5H, m), 3.85-4.05 (5H, m), 4.05-4.20 (1H, m), 6.05-6.30 (1H, m), 7.15-7.35 (5H, m)

Reference Example 8-1

3-[(3'S,4'aR,8'aR)-1'-Propyloctahydro-1'H-spiro[1,3-dioxolane-2,6'-quinolin]-3'-yl]-1-[2-(dimethylamino)ethyl]-1-ethylurea To a mixture of (3'S,4'aR,8'aR)-1'-propyloctahydro-1'H-spiro[1,3-dioxolane-2,6'-quinoline]-3'-carboxylic acid (reference example 5-1) (202 mg) and toluene (3.6 mL) was added N,N-diisopropylethylamine (0.194 mL), followed by diphenylphosphoryl azide (0.245 mL) while stirring at room temperature, and the mixture was refluxed for 1 hour. After cooling to room temperature, to the reaction mixture was added [2-(dimethylamino)ethyl](ethyl)amine (0.191 mL), and stirred for 3 hours. A saturated aqueous solution of sodium bicarbonate was added to the reaction mixture, and extracted with methylene chloride. After the separated organic layer was dried over anhydrous sodium sulfate, it was concentrated under reduced pressure. The residue was purified by aminopropyl silica gel column chromatography (eluent: 25%-85% ethyl acetate/hexane, gradient elution) to give the title compound (157 mg).

$^1$H-NMR (CDCl$_3$) δ ppm: 0.83 (3H, t, J=7.4 Hz), 1.05-1.50 (8H, m), 1.50-1.85 (6H, m), 1.95-2.10 (1H, m), 2.20-2.50 (11H, m), 2.75-2.85 (1H, m), 3.15-3.40 (4H, m), 3.85-4.05 (5H, m), 6.55-6.75 (1H, m)

Reference Example 8-7

3-[(3'S*,4'aR*,8'aR*)-1'-Propyloctahydro-1'H-spiro[1,3-dioxolane-2,6'-quinolin]-3'-yl]-1-[2-(dimethyl-amino)ethyl]-1-(2-methylpropyl)urea To a mixture of (3'S*,4'aR*,8'aR*)-1'-propyloctahydro-1'H-spiro[1,3-dioxolane-2,6'-quinoline]-3'-carboxylic acid (reference example 5-2) (500 mg) and toluene (8.8 mL) was added N,N-diisopropylethylamine (0.480 mL), followed by diphenylphosphoryl azide (0.609 mL) while stirring at room temperature, and the mixture was refluxed for 1 hour. After cooling to room temperature, to the reaction mixture was added dimethyl({2-[2-(methylpropyl)amino]ethyl})amine (458 mg), and stirred for 5 hours at the same temperature. A saturated aqueous solution of sodium bicarbonate was added to the reaction mixture, and extracted with methylene chloride. After the separated organic layer was dried over anhydrous sodium sulfate, it was concentrated under reduced pressure. The residue was purified by aminopropyl silica gel column chromatography (eluent: 25%-70% ethyl acetate/hexane, gradient elution) to give the title compound (404 mg).

$^1$H-NMR (CDCl$_3$) δ ppm: 0.84 (3H, t, J=7.4 Hz), 0.85-0.95 (6H, m), 1.10-1.25 (1H, m), 1.25-1.50 (4H, m), 1.50-1.85 (6H, m), 1.85-2.10 (2H, m), 2.20-2.65 (11H, m), 2.75-2.85 (1H, m), 2.90-3.05 (1H, m), 3.05-3.20 (1H, m), 3.20-3.30 (1H, m), 3.30-3.40 (1H, m), 3.85-4.05 (5H, m), 6.53 (1H, br)

Reference examples 8-2 to 8-6 and reference examples 8-8 to 8-22 were prepared in a manner similar to those as described in reference example 8-1 or 8-7 using the corresponding amines instead of [2-(dimethylamino)ethyl](ethyl)amine. These were illustrated in Table 6.

TABLE 6

| Reference example | Structure |
|---|---|
| 8-1 | Chiral |
| 8-2 | Chiral |
| 8-3 | Chiral 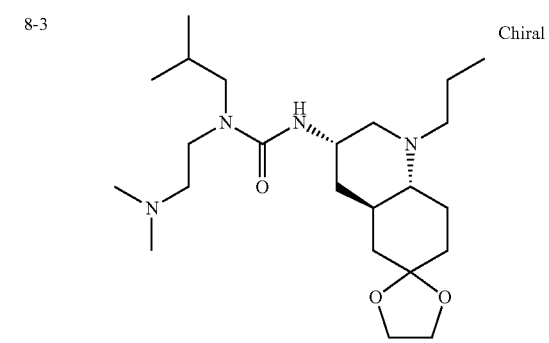 |
| 8-4 | Chiral 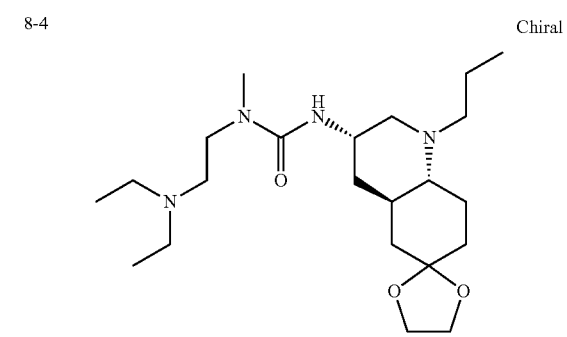 |
| 8-5 | Chiral 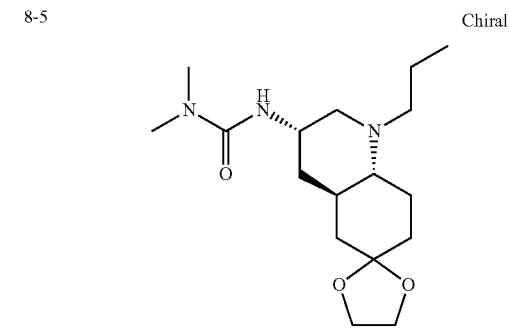 |
| 8-6 | Chiral 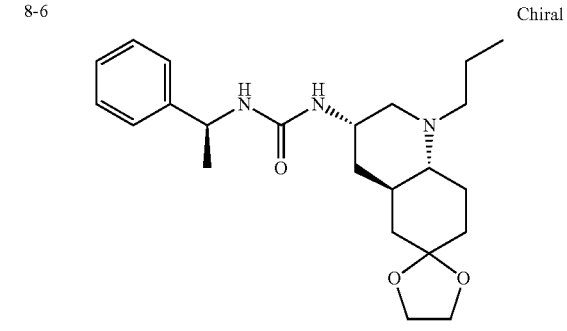 |

TABLE 6-continued
| Reference example | Structure |
|---|---|
| 8-7 | 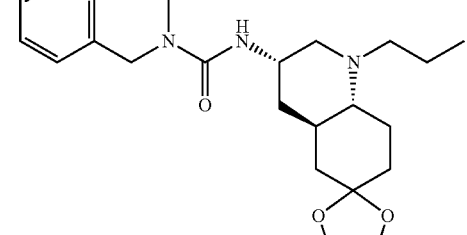 |
| 8-8 | 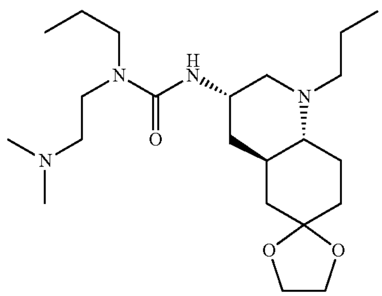 [SMILES: CCCN(CCN(C)C)C(=O)N[C@H]1C[C@@H]2CC3(CC[C@H]2N(CCC)C1)OCCO3] |
| 8-9 | 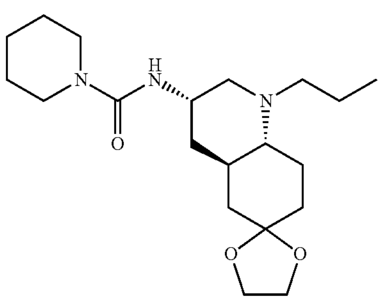 [SMILES: CCCN1C[C@@H](NC(=O)N2CCCCC2)C[C@@H]2CC3(CC[C@H]21)OCCO3] |
| 8-10 | 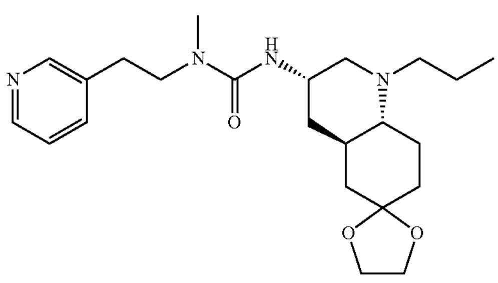 [SMILES: CCCN1C[C@@H](NC(=O)N(C)CCc2cccnc2)C[C@@H]2CC3(CC[C@H]21)OCCO3] |
| 8-11 | 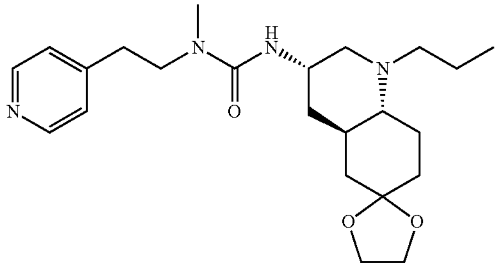 [SMILES: CCCN1C[C@@H](NC(=O)N(C)CCc2ccncc2)C[C@@H]2CC3(CC[C@H]21)OCCO3] |
| 8-12 | 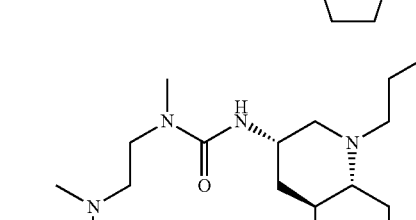 |
| 8-13 | |
| 8-14 | |
| 8-15 | |
| 8-16 | |

TABLE 6-continued

| Reference example | Structure |
|---|---|
| 8-17 | 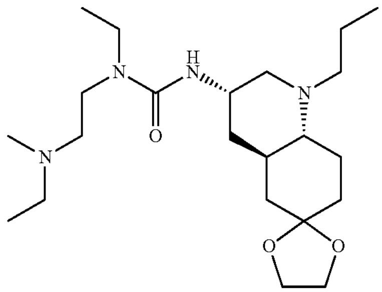 [SMILES: CCCN1C[C@@H](NC(=O)N(CC)CCN(C)CC)C[C@@H]2CC3(CC[C@H]21)OCCO3] |
| 8-18 | 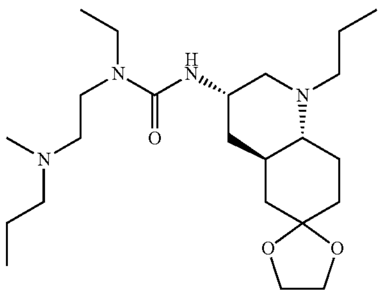 [SMILES: CCCN(C)CCN(CC)C(=O)N[C@H]1C[C@@H]2CC3(CC[C@H]2N(CCC)C1)OCCO3] |
| 8-19 | 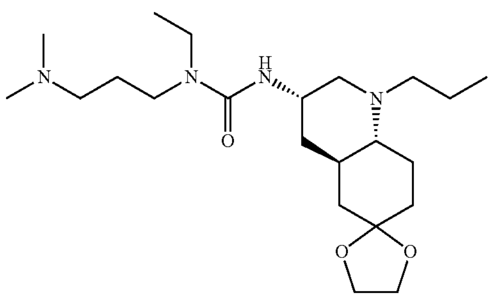 [SMILES: CCCN1C[C@@H](NC(=O)N(CC)CCCN(C)C)C[C@@H]2CC3(CC[C@H]21)OCCO3] |
| 8-20 | 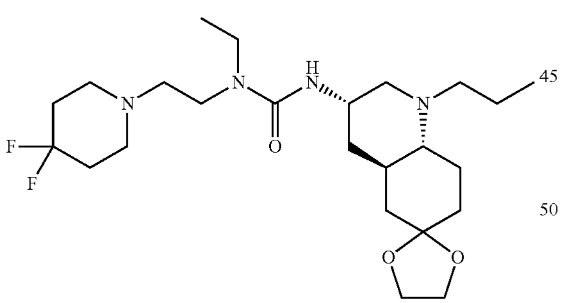 |
| 8-21 | 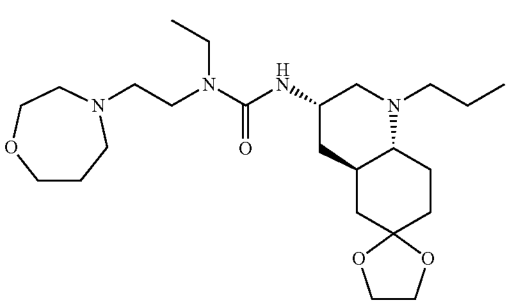 [SMILES: CCCN1C[C@@H](NC(=O)N(CC)CCN2CCCOCC2)C[C@@H]2CC3(CC[C@H]21)OCCO3] |
| 8-22 | |

The structures of the reference example 8-1 to 8-6 in Table 6 indicate absolute configuration, and the structures of the reference example 8-7 to 8-22 in Table 6 indicate relative configuration.

The physical data of reference examples 8-2 to 8-6 and reference examples 8-8 to 8-22 were shown below.

Reference Example 8-2

$^1$H-NMR (CDCl$_3$) δ ppm: 0.83 (3H, t, J=7.4 Hz), 0.89 (3H, t, J=7.4 Hz), 1.10-1.25 (1H, m), 1.25-1.45 (4H, m), 1.45-1.85 (8H, m), 1.95-2.10 (1H, m), 2.20-2.50 (10H, m), 2.50-2.65 (1H, m), 2.75-2.85 (1H, m), 3.05-3.40 (4H, m), 3.85-4.00 (5H, m), 6.50-6.75 (1H, m)

Reference Example 8-3

$^1$H-NMR (CDCl$_3$) δ ppm: 0.84 (3H, t, J=7.4 Hz), 0.85-0.95 (6H, m), 1.10-1.25 (1H, m), 1.25-1.50 (4H, m), 1.50-1.65 (2H, m), 1.65-1.85 (4H, m), 1.85-2.10 (2H, m), 2.25-2.65 (11H, m), 2.75-2.85 (1H, m), 2.90-3.05 (1H, m), 3.05-3.20 (1H, m), 3.20-3.30 (1H, m), 3.30-3.40 (1H, m), 3.85-4.05 (5H, m), 6.54 (1H, br)

Reference Example 8-4

$^1$H-NMR (CDCl$_3$) δ ppm: 0.83 (3H, t, J=7.3 Hz), 1.05 (6H, t, J=7.2 Hz), 1.10-1.25 (1H, m), 1.25-1.50 (4H, m), 1.50-1.85 (6H, m), 1.95-2.10 (1H, m), 2.30-2.45 (2H, m), 2.45-2.65 (7H, m), 2.75-2.85 (1H, m), 2.90 (3H, s), 3.10-3.25 (1H, m), 3.30-3.45 (1H, m), 3.85-4.05 (5H, m), 6.10-6.30 (1H, m)

Reference Example 8-5

$^1$H-NMR (CDCl$_3$) δ ppm: 0.85 (3H, t, J=7.4 Hz), 1.10-1.25 (1H, m), 1.25-1.50 (4H, m), 1.50-1.85 (6H, m), 2.00-2.10 (1H, m), 2.20-2.45 (2H, m), 2.55-2.70 (1H, m), 2.75-2.85 (1H, m), 2.90 (6H, s), 3.90-4.05 (5H, m), 5.41 (1H, d, J=7.9 Hz)

Reference Example 8-6

$^1$H-NMR (CDCl$_3$) δ ppm: 0.77 (3H, t, J=7.4 Hz), 1.05-1.45 (5H, m), 1.46 (3H, d, J=6.8 Hz), 1.50-1.85 (5H, m), 1.95-2.05 (1H, m), 2.20-2.35 (3H, m), 2.35-2.50 (1H, m), 2.55-2.65 (1H, m), 3.90-4.00 (5H, m), 4.51 (1H, d, J=6.5 Hz), 4.70-4.80 (1H, m), 5.20 (1H, d, J=8.2 Hz), 7.20-7.40 (5H, m)

Reference Example 8-8

¹H-NMR (CDCl₃) δ ppm: 0.83 (3H, t, J=7.3 Hz), 0.89 (3H, t, J=7.3 Hz), 1.10-1.25 (1H, m), 1.25-1.45 (4H, m), 1.45-1.85 (8H, m), 2.00-2.10 (1H, m), 2.20-2.50 (10H, m), 2.50-2.65 (1H, m), 2.75-2.85 (1H, m), 3.05-3.40 (4H, m), 3.85-4.00 (5H, m), 6.50-6.70 (1H, m)

Reference Example 8-9

MS (ESI, m/z): 366 (M+H)+

Reference Example 8-10

¹H-NMR (CDCl₃) δ ppm: 0.84 (3H, t, J=7.4 Hz), 1.10-1.25 (1H, m), 1.25-1.50 (4H, m), 1.50-1.90' (6H, m), 2.00-2.10 (1H, m), 2.25-2.35 (1H, m), 2.35-2.45 (1H, m), 2.55-2.70 (1H, m), 2.75-2.90 (6H, m), 3.35-3.50 (1H, m), 3.50-3.60 (1H, m), 3.85-4.05 (5H, m), 5.41 (1H, d, J=80 Hz), 7.20-7.30 (1H, m), 7.50-7.60 (1H, m), 8.45-8.50 (2H, m)

Reference Example 8-11

¹H-NMR (CDCl₃) δ ppm: 0.84 (3H, t, J=7.4 Hz), 1.10-1.25 (1H, m), 1.25-1.50 (4H, m), 1.50-1.90 (6H, m), 2.00-2.10 (1H, m), 2.25-2.35 (1H, m), 2.35-2.45 (1H, m), 2.55-2.70 (1H, m), 2.70-2.90 (6H, m), 3.40-3.60 (2H, m), 3.90-4.05 (5H, m), 5.40 (1H, d, J=8.1 Hz), 7.10-7.20 (2H, m), 8.45-8.55 (2H, m)

Reference Example 8-12

MS (ESI, m/z): 414 (M+H)+

Reference Example 8-13

¹H-NMR (CDCl₃) δ ppm: 0.82 (3H, t, J=7.4 Hz), 1.10-1.45 (5H, m), 1.50-1.85 (6H, m), 1.95-2.10 (1H, m), 2.20-2.45 (2H, m), 2.50-2.65 (1H, m), 2.70-2.80 (1H, m), 2.87 (3H, s), 2.97 (3H, s), 3.30-3.60 (4H, m), 3.85-4.05 (5H, m), 5.45 (1H, d, J=8.3 Hz), 6.65-6.80 (3H, m), 7.20-7.30 (2H, m)

Reference Example 8-14

MS (ESI, m/z): 453 (M+H)+

Reference Example 8-15

MS (ESI, m/z): 441 (M+H)+

Reference Example 8-16

¹H-NMR (CDCl₃) δ ppm: 0.83 (3H, t, J=7.3 Hz), 1.05-1.85 (18H, m), 1.95-2.10 (1H, m), 2.25-2.65 (9H, m), 2.75-2.85 (1H, m), 3.15-3.45 (8H, m), 3.85-4.05 (5H, m), 6.20-6.35 (1H, m)

Reference Example 8-17

MS (ESI, m/z): 411 (M+H)+

Reference Example 8-18

MS (ESI, m/z): 425 (M+H)+

Reference Example 8-19

MS (ESI, m/z): 411 (M+H)+

Reference Example 8-20

MS (ESI, m/z): 473 (M+H)+

Reference Example 8-21

¹H-NMR (CDCl₃) δ ppm: 0.84 (3H, t, J=7.4 Hz), 1.10-1.25 (4H, m), 1.25-1.50 (4H, m), 1.50-1.65 (2H, m), 1.65-1.85 (4H, m), 1.85-1.95 (2H, m), 2.00-2.10 (1H, m), 2.25-2.45 (2H, m), 2.55-2.90 (8H, m), 3.15-3.40 (4H, m), 3.65-3.85 (4H, m), 3.85-4.05 (5H, m), 5.78 (1H, d, J=8.1 Hz)

Reference Example 8-22

MS (ESI, m/z): 473 (M+H)+

Reference Example 9-1

3-[(3S,4aR,8aR)-6-Oxo-1-propyldecahydroquinolin-3-yl]-1-[2-(dimethylamino)ethyl]-1-ethylurea To 3-[(3'S,4'aR,8'aR)-1'-propyloctahydro-1'H-spiro[1,3-dioxolane-2,6'-quinolin]-3'-yl]-1-[2-(dimethylamino)ethyl]-1-ethylurea (reference example 8-1) (157 mg) was added 2 mol/L hydrochloric acid (3.95 mL) and the mixture was stirred at room temperature for 14 hours. The reaction mixture was made alkaline with potassium carbonate. To the resulting mixture was added ethyl acetate, and extracted with ethyl acetate. After the separated organic layer was dried over anhydrous sodium sulfate, it was concentrated under reduced pressure to give the title compound (130 mg).

MS (ESI, m/z): 353 (M+H)+

Reference Example 9-7

3-[(3S*,4aR*,8aR*)-6-Oxo-1-propyldecahydroquinolin-3-yl]-1,1-diethylurea

To 3-[(3'S,4'aR,8'aR)-1'-propyloctahydro-1'H-spiro[1,3-dioxolane-2,6'-quinolin]-3'-yl]-1,1-diethylurea (reference example 7-1) (221 mg) was added 2 mol/L hydrochloric acid (5.0 mL) and the mixture was stirred at room temperature for 1.5 hours. The reaction mixture was made alkaline with potassium carbonate. The resulting mixture was extracted with methylene chloride/2-propanol mixed solvent (methylene chloride:2-propanol=3:1). After the organic layer was dried over anhydrous sodium sulfate, it was concentrated under reduced pressure to give the title compound (202 mg).

MS (ESI, m/z): 310 (M+H)+

Reference examples 9-2 to 9-6 and reference examples 9-8 to 9-49 were prepared in a manner similar to those as described in reference example 9-1 or reference example 9-7 using the corresponding ketals instead of 3-[(3'S, 4'aR, 8'aR)-1'-propyloctahydro-1'H-spiro[1,3-dioxolane-2,6'-quinolin]-3'-yl]-1-[2-(dimethylamino)ethyl]-1-ethylurea. These were illustrated in Table 7.

TABLE 7

| Reference example | Structure |
|---|---|
| 9-1 | Chiral (structure) |
| 9-2 | Chiral (structure) |
| 9-3 | Chiral (structure) |
| 9-4 | Chiral (structure) |
| 9-5 | Chiral (structure) |
| 9-6 | Chiral (structure) |
| 9-7 | (structure) |
| 9-8 | (structure) |
| 9-9 | (structure) |

TABLE 7-continued

| Reference example | Structure |
|---|---|
| 9-10 | (structure) |
| 9-11 | (structure) |
| 9-12 | (structure) |
| 9-13 | (structure) |
| 9-14 | (structure) |
| 9-15 | (structure) |
| 9-16 | (structure) |
| 9-17 | (structure) |
| 9-18 | (structure) |
| 9-19 | (structure) |

TABLE 7-continued

| Reference example | Structure |
|---|---|
| 9-20 | (structure) |
| 9-21 | (structure) |
| 9-22 | (structure) |
| 9-23 | (structure) |
| 9-24 | (structure) |
| 9-25 | (structure) |
| 9-26 | (structure) |
| 9-27 | (structure) |
| 9-28 | (structure) |
| 9-29 | (structure) |

TABLE 7-continued

| Reference example | Structure |
|---|---|
| 9-30 | 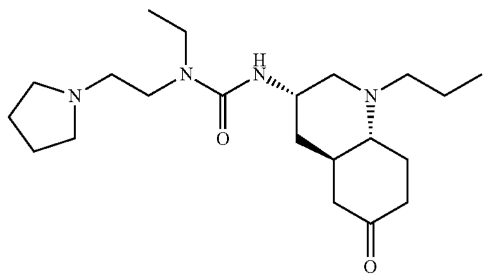 [SMILES: CCCN1C[C@@H](NC(=O)N(CC)CCN2CCCC2)C[C@@H]2CC(=O)CC[C@H]21] |
| 9-31 | 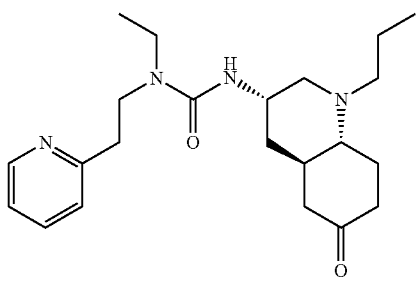 [SMILES: CCCN1C[C@@H](NC(=O)N(CC)CCc2ccccn2)C[C@@H]2CC(=O)CC[C@H]21] |
| 9-32 | 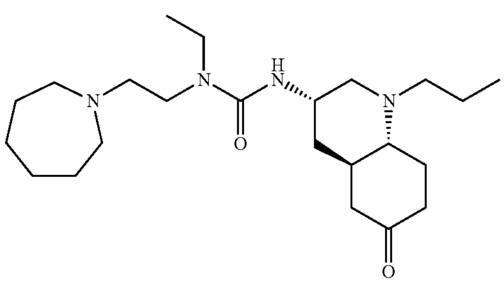 [SMILES: CCCN1C[C@@H](NC(=O)N(CC)CCN2CCCCCC2)C[C@@H]2CC(=O)CC[C@H]21] |
| 9-33 | 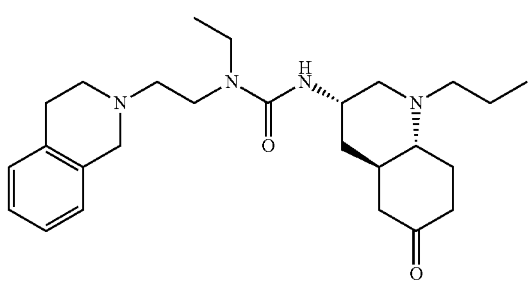 [SMILES: CCCN1C[C@@H](NC(=O)N(CC)CCN2CCc3ccccc3C2)C[C@@H]2CC(=O)CC[C@H]21] |
| 9-34 | 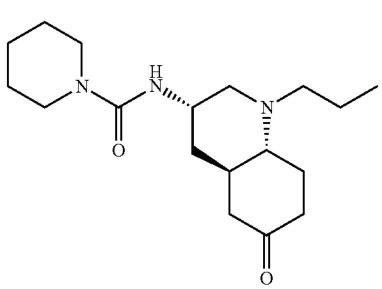 [SMILES: CCCN1C[C@@H](NC(=O)N2CCCCC2)C[C@@H]2CC(=O)CC[C@H]21] |
| 9-35 | |
| 9-36 | |
| 9-37 | |
| 9-38 | |
| 9-39 | |

TABLE 7-continued

| Reference example | Structure |
|---|---|
| 9-40 | 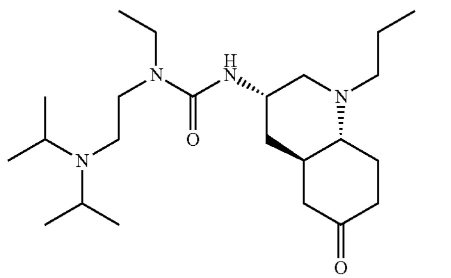 [SMILES: CCCN1C[C@@H](NC(=O)N(CC)CCN(C(C)C)C(C)C)C[C@@H]2CC(=O)CC[C@H]21] |
| 9-41 | 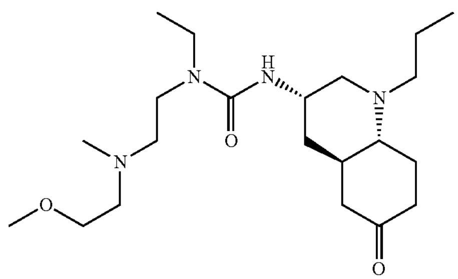 [SMILES: CCCN1C[C@@H](NC(=O)N(CC)CCN(C)CCOC)C[C@@H]2CC(=O)CC[C@H]21] |
| 9-42 | 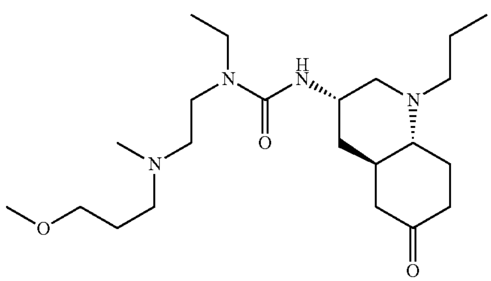 [SMILES: CCCN1C[C@@H](NC(=O)N(CC)CCN(C)CCCOC)C[C@@H]2CC(=O)CC[C@H]21] |
| 9-43 | 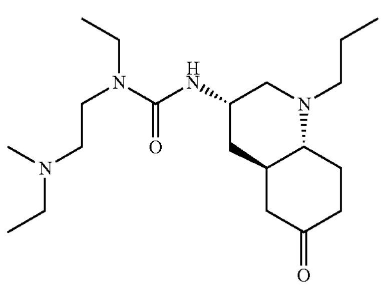 [SMILES: CCCN1C[C@@H](NC(=O)N(CC)CCN(C)CC)C[C@@H]2CC(=O)CC[C@H]21] |
| 9-44 | 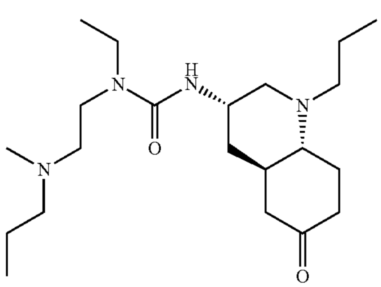 [SMILES: CCCN(C)CCN(CC)C(=O)N[C@H]1C[C@@H]2CC(=O)CC[C@H]2N(CCC)C1] |
| 9-45 | |
| 9-46 | |
| 9-47 | |
| 9-48 | |
| 9-49 | |

The structures of the reference example 9-1 to 9-6 in Table 7 indicate absolute configuration, and the structures of the reference example 9-7 to 9-49 in Table 7 indicate relative configuration.

The physical data of reference examples 9-2 to 9-6 and reference examples 9-8 to 9-49 were shown below.

Reference Example 9-2

¹H-NMR (CDCl₃) δ ppm: 0.86 (3H, t, J=7.4 Hz), 0.89 (3H, t, J=7.4 Hz), 1.25-1.35 (1H, m), 1.35-1.65 (5H, m), 1.70-1.90 (2H, m), 2.05-2.30 (9H, m), 2.30-2.55 (7H, m), 2.55-2.70 (1H, m), 2.80-2.90 (1H, m), 3.05-3.40 (4H, m), 3.95-4.10 (1H, m), 6.45-6.70 (1H, m)

Reference Example 9-3

¹H-NMR (CDCl₃) δ ppm: 0.86 (3H, t, J=7.3 Hz), 0.89 (6H, d, J=6.7 Hz), 1.25-1.60 (4H, m), 1.65-1.95 (3H, m), 2.05-2.30 (9H, m), 2.30-2.55 (7H, m), 2.55-2.70 (1H, m), 2.80-2.90 (1H, m), 2.90-3.15 (2H, m), 3.15-3.40 (2H, m), 3.95-4.10 (1H, m), 6.50 (1H, br)

Reference Example 9-4

¹H-NMR (CDCl₃) δ ppm: 0.85 (3H, t, J=7.3 Hz), 1.03 (6H, t, J=7.2 Hz), 1.25-1.60 (4H, m), 1.65-1.90 (3H, m), 2.05-2.30 (3H, m), 2.30-2.70 (11H, m), 2.80-2.95 (4H, m), 3.15-3.40 (2H, m), 4.00-4.10 (1H, m), 6.16 (1H, brs)

Reference Example 9-5

MS (ESI, m/z): 282 (M+H)+

Reference Example 9-6

¹H-NMR (CDCl₃) δ ppm: 0.79 (3H, t, J=7.4 Hz), 1.15-1.55 (7H, m), 1.60-1.85 (2H, m), 2.00-2.25 (3H, m), 2.25-2.50 (6H, m), 2.55-2.70 (1H, m), 3.90-4.05 (1H, m), 4.54 (1H, d, J=6.2 Hz), 4.60-4.75 (1H, m), 5.09 (1H, d, J=8.0 Hz), 7.20-7.40 (5H, m)

Reference Example 9-8

MS (ESI, m/z): 358 (M+H)+

Reference Example 9-9

MS (ESI, m/z): 282 (M+H)+

Reference Example 9-10

MS (ESI, m/z): 324 (M+H)+

Reference Example 9-11

MS (ESI, m/z): 372 (M+H)+

Reference Example 9-12

MS (ESI, m/z): 326 (M+H)+

Reference Example 9-13

MS (ESI, m/z): 268 (M+H)+

Reference Example 9-14

MS (ESI, m/z): 373 (M+H)+

Reference Example 9-15

MS (ESI, m/z): 340 (M+H)+

Reference Example 9-16

¹H-NMR (CDCl₃) δ ppm: 0.60-0.85 (4H, m), 0.87 (3H, t, J=7.3 Hz), 1.25-1.35 (1H, m), 1.35-1.60 (3H, m), 1.70-1.95 (2H, m), 2.10-2.30 (3H, m), 2.30-2.55 (6H, m), 2.65-2.75 (1H, m), 2.80-2.95 (4H, m), 4.00-4.10 (1H, m), 6.18 (1H, d, J=8.2 Hz)

Reference Example 9-17

MS (ESI, m/z): 367 (M+H)+

Reference Example 9-18

MS (ESI, m/z): 376 (M+H)+

Reference Example 9-19

MS (ESI, m/z): 353 (M+H)+

Reference Example 9-20

MS (ESI, m/z): 415 (M+H)+

Reference Example 9-21

MS (ESI, m/z): 381 (M+H)+

Reference Example 9-22

¹H-NMR (CDCl₃) δ ppm: 0.86 (3H, t, J=7.4 Hz), 0.89 (3H, t, J=7.4 Hz), 1.25-1.65 (6H, m), 1.70-1.90 (2H, m), 2.05-2.30 (9H, m), 2.30-2.55 (7H, m), 2.55-2.75 (1H, m), 2.80-2.90 (1H, m), 3.05-3.40 (4H, m), 3.95-4.10 (1H, m), 6.45-6.65 (1H, m)

Reference Example 9-23

MS (ESI, m/z): 429 (M+H)+

Reference Example 9-24

¹H-NMR (CDCl₃) δ ppm: 0.87 (3H, t, J=7.3 Hz), 1.13 (3H, t, J=7.1 Hz), 1.20-1.35 (1H, m), 1.35-1.65 (7H, m), 1.70-1.85 (1H, m), 1.85-1.95 (1H, m), 2.05-2.30 (11H, m), 2.30-2.50 (5H, m), 2.60-2.75 (1H, m), 2.80-2.90 (1H, m), 3.10-3.35 (4H, m), 4.00-4.10 (1H, m), 5.29 (1H, d, J=8.4 Hz)

Reference Example 9-25

MS (ESI, m/z): 393 (M+H)+

Reference Example 9-26

MS (ESI, m/z): 409 (M+H)+

Reference Example 9-27

MS (ESI, m/z): 381 (M+H)+

Reference Example 9-28

MS (ESI, m/z): 408 (M+H)+

Reference Example 9-29

¹H-NMR (CDCl₃) δ ppm: 0.87 (3H, t, J=7.2 Hz), 1.00 (6H, t, J=7.2 Hz), 1.13 (3H, t, J=7.6 Hz), 1.20-1.35 (1H, m), 1.35-1.60 (3H, m), 1.60-1.95 (5H, m), 2.05-2.30 (3H, m), 2.30-2.60 (10H, m), 2.60-2.75 (1H, m), 2.80-2.95 (1H, m), 3.10-3.35 (4H, m), 4.00-4.10 (1H, m), 5.37 (1H, d, J=8.0 Hz)

Reference Example 9-30

¹H-NMR (CDCl₃) δ ppm: 0.86 (3H, t, J=7.2 Hz), 1.13 (3H, t, J=7.2 Hz), 1.20-1.60 (5H, m), 1.70-1.95 (6H, m), 2.05-2.30 (3H, m), 2.30-2.70 (11H, m), 2.80-2.90 (1H, m), 3.10-3.50 (4H, m), 4.00-4.10 (1H, m), 5.70-5.80 (1H, m)

Reference Example 9-31

MS (ESI, m/z): 387 (M+H)+

Reference Example 9-32

¹H-NMR (CDCl₃) δ ppm: 0.86 (3H, t, J=7.6 Hz), 1.12 (3H, t, J=7.2 Hz), 1.20-1.35 (1H, m), 1.35-1.95 (14H, m), 2.05-2.30 (3H, m), 2.30-2.55 (5H, m), 2.56-2.75 (6H, m), 2.80-2.90 (1H, m), 3.10-3.50 (4H, m), 4.00-4.10 (1H, m), 5.839 (1H, d, J=7.6 Hz)

Reference Example 9-33

¹H-NMR (CDCl₃) δ ppm: 0.84 (3H, t, J=7.2 Hz), 1.15 (3H, t, J=7.2 Hz), 1.20-1.50 (4H, m), 1.65-1.90 (2H, m), 2.00-2.24 (3H, m), 2.24-2.41 (4H, m), 2.43-2.61 (2H, m), 2.63-2.73 (2H, m), 2.75-2.94 (5H, m), 3.20-3.55 (4H, m), 3.65-3.80 (2H, m), 4.00-4.10 (1H, m), 5.80-5.95 (1H, m), 6.95-7.05 (1H, m), 7.05-7.20 (3H, m)

Reference Example 9-34

MS (ESI, m/z): 322 (M+H)+

Reference Example 9-35

MS (ESI, m/z): 373 (M+H)+

Reference Example 9-36

MS (ESI, m/z): 373 (M+H)+

Reference Example 9-37

MS (ESI, m/z): 370 (M+H)+

Reference Example 9-38

MS (ESI, m/z): 395 (M+H)+

Reference Example 9-39

MS (ESI, m/z): 401 (M+H)+

Reference Example 9-40

MS (ESI, m/z): 409 (M+H)+

Reference Example 9-41

MS (ESI, m/z): 397 (M+H)+

Reference Example 9-42

MS (ESI, m/z): 411 (M+H)+

Reference Example 9-43

MS (ESI, m/z): 367 (M+H)+

Reference Example 9-44

MS (ESI, m/z): 381 (M+H)+

Reference Example 9-45

¹H-NMR (CDCl₃) δ ppm: 0.86 (3H, t, J=7.4 Hz), 1.13 (3H, t, J=7.1 Hz), 1.25-1.60 (4H, m), 1.60-1.90 (4H, m), 2.05-2.55 (16H, m), 2.60-2.70 (1H, m), 2.80-2.95 (1H, m), 3.10-3.35 (4H, m), 4.00-4.10 (1H, m), 5.71 (1H, d, J=7.6 Hz)

Reference Example 9-46

¹H-NMR (CDCl₃) δ ppm: 0.87 (3H, t, J=7.4 Hz), 1.14 (3H, t, J=7.2 Hz), 1.25-1.60 (4H, m), 1.70-2.05 (6H, m), 2.05-2.30 (3H, m), 2.30-2.75 (12H, m), 2.80-2.90 (1H, m), 3.15-3.45 (4H, m), 4.00-4.10 (1H, m), 5.54 (1H, d, J=7.8 Hz)

Reference Example 9-47

¹H-NMR (CDCl₃) δ ppm: 0.87 (3H, t, J=7.4 Hz), 1.14 (3H, t, J=7.2 Hz), 1.25-1.35 (1H, m), 1.35-1.60 (3H, m), 1.70-1.95 (4H, m), 2.05-2.30 (3H, m), 2.30-2.55 (5H, m), 2.60-2.70 (3H, m), 2.70-2.90 (5H, m), 3.15-3.40 (4H, m), 3.65-3.85 (4H, m), 4.00-4.10 (1H, m), 5.76 (1H, d, J=7.6 Hz)

Reference Example 9-48

MS (ESI, m/z): 401 (M+H)+

Reference Example 9-49

MS (ESI, m/z): 429 (M+H)+

Reference Example 10-1

3-[(3S,4aR,8aR)-7-[(Dimethylamino)methylidene]-6-oxo-1-propyldecahydroquinolin-3-yl]-1-[2-(dimethylamino)ethyl]-1-ethylurea To a mixture of 3-[(3S,4aR,8aR)-6-oxo-1-propyldecahydroquinolin-3-yl]-1-[2-(dimethylamino)ethyl]-1-ethylurea (reference example 9-1) (130 mg) and toluene (1.2 mL) was added t-butoxybis(dimethylamino)methane (0.092 mL) while stirring at room temperature, and the mixture was refluxed for 40 minuets. After cooling to room temperature, the reaction mixture was concentrated under reduced pressure. The residue was purified by 1,2-dihydroxypropyl silica gel column chromatography (eluent: 0%-30% methanol/ethyl acetate, gradient elution) to give the title compound (110 mg).
MS (ESI, m/z): 408 (M+H)+

Reference Example 10-7

3-[(3S*,4aR*,8aR*)-7-[(Dimethylamino)methylidene]-6-oxo-1-propyldecahydroquinolin-3-yl]-1,1-diethylurea To a mixture of 3-[(3S*,4aR*,8aR*)-6-oxo-1-propyldecahydroquinolin-3-yl]-1,1-diethylurea (reference example 9-7) (193 mg) and toluene (3.0 mL) was added t-butoxybis(dimethylamino)methane (0.155 mL) while stirring at room temperature, and the mixture was refluxed for 1 hour. To the reaction mixture was added t-butoxybis(dimethylamino)methane (0.077 mL) again, and refluxed at same temperature for 1 hour. After cooling to room temperature, the reaction mixture was concentrated under reduced pressure. The residue was purified by silica gel column chromatography (eluent: 0%-5% methanol/ethyl acetate, gradient elution) to give the title compound (88 mg).

¹H-NMR (CDCl₃) δ ppm: 0.89 (3H, t, J=7.4 Hz), 1.11-1.18 (7H, m), 1.34-1.57 (2H, m), 1.72-1.87 (1H, m), 1.90-2.17 (3H, m), 2.24-2.48 (4H, m), 2.59-2.74 (1H, m), 2.79-2.91 (1H, m), 3.12 (6H, s), 3.18-3.35 (5H, m), 3.98-4.12 (1H, m), 5.38 (1H, d, J=8.0 Hz), 7.51 (1H, s)

Reference examples 10-2 to 10-6 and reference examples 10-8 to 10-49 were prepared in a manner similar to those as described in reference example 10-1 or reference example 10-7 using the corresponding 6-oxodecahydroquinoline instead of 3-[(3'S,4'aR,8'aR)-6-oxo-1'-propyloctahydroquinolin-3-yl]-1-[2-(dimethylamino)ethyl]-1-ethylurea. These were illustrated in Table 8.

TABLE 8

| Reference example | Structure |
|---|---|
| 10-1 | Chiral |
| 10-2 | Chiral |
| 10-3 | Chiral |

TABLE 8-continued

| Reference example | Structure |
|---|---|
| 10-4 | Chiral |
| 10-5 | Chiral |
| 10-6 | Chiral |
| 10-7 | 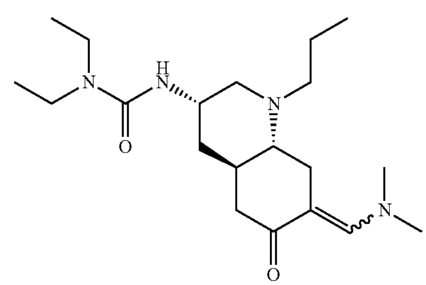 [SMILES: CCCN1C[C@@H](NC(=O)N(CC)CC)C[C@@H]2CC(=O)C(=CN(C)C)C[C@H]21] |
| 10-8 | 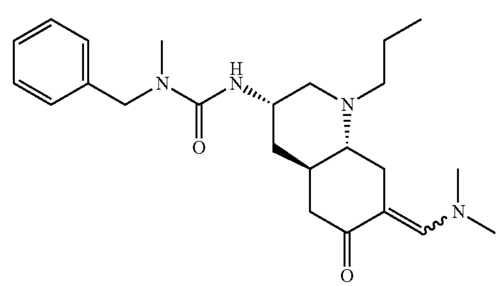 [SMILES: CCCN1C[C@@H](NC(=O)N(C)Cc2ccccc2)C[C@@H]2CC(=O)C(=CN(C)C)C[C@H]21] |

TABLE 8-continued
| Reference example | Structure |
|---|---|
| 10-9 | 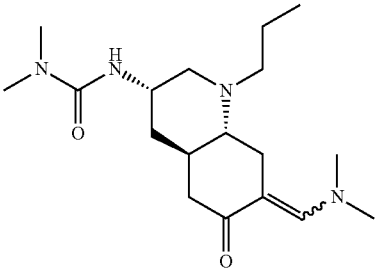 |
| 10-10 | 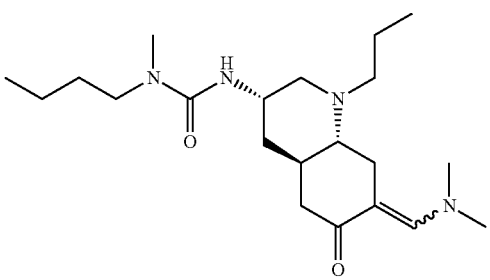 [SMILES: CCCCN(C)C(=O)N[C@H]1C[C@@H]2CC(=O)C(=CN(C)C)C[C@H]2N(CCC)C1] |
| 10-11 | 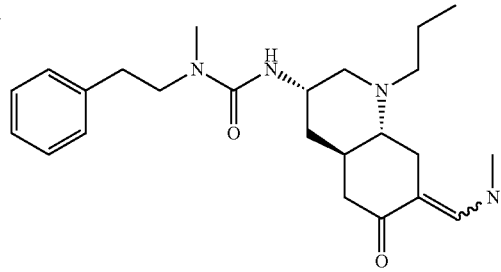 |
| 10-12 | 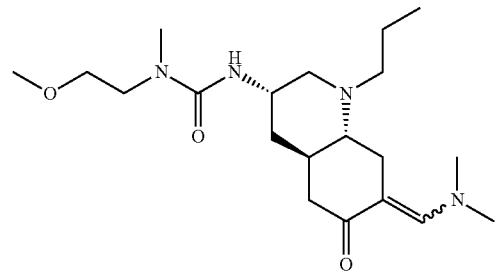 |
| 10-13 | 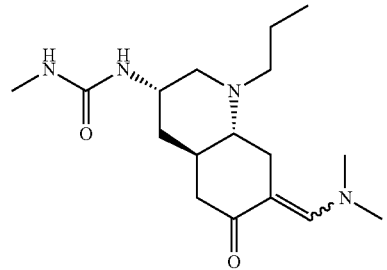 |
| 10-14 | 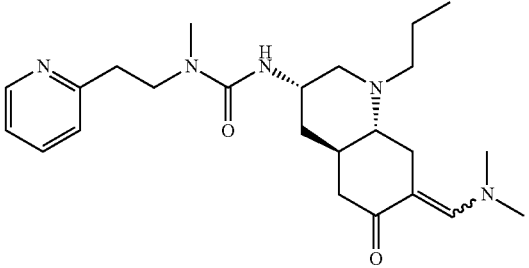 [SMILES: CCCN1C[C@@H](NC(=O)N(C)CCc2ccccn2)C[C@@H]2CC(=O)C(=CN(C)C)C[C@H]21] |
| 10-15 | 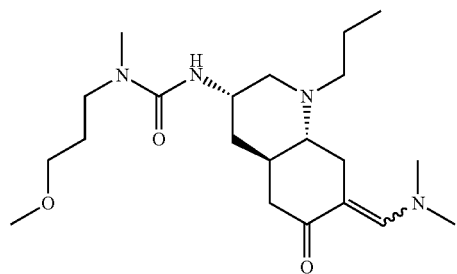 |
| 10-16 | 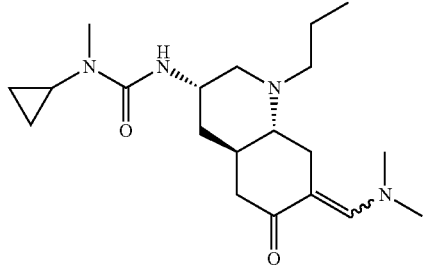 [SMILES: CCCN1C[C@@H](NC(=O)N(C)C2CC2)C[C@@H]2CC(=O)C(=CN(C)C)C[C@H]21] |
| 10-17 | 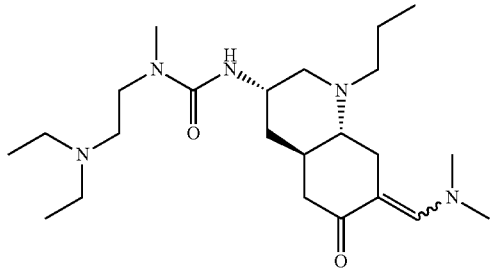 [SMILES: CCCN1C[C@@H](NC(=O)N(C)CCN(CC)CC)C[C@@H]2CC(=O)C(=CN(C)C)C[C@H]21] |
| 10-18 | 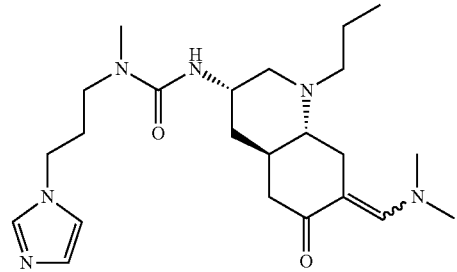 [SMILES: CCCN1C[C@@H](NC(=O)N(C)CCCn2ccnc2)C[C@@H]2CC(=O)C(=CN(C)C)C[C@H]21] |

TABLE 8-continued

| Reference example | Structure |
|---|---|
| 10-19 | (structure) |
| 10-20 | (structure) |
| 10-21 | (structure) |
| 10-22 | (structure) |
| 10-23 | (structure) |
| 10-24 | (structure) |
| 10-25 | (structure) |
| 10-26 | (structure) |
| 10-27 | (structure) |
| 10-28 | (structure) |

TABLE 8-continued
| Reference example | Structure |
|---|---|
| 10-29 | 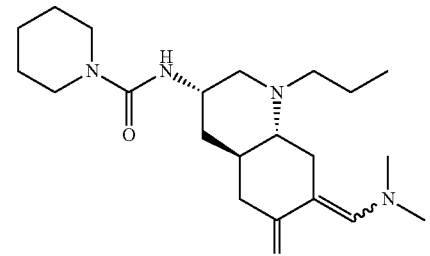 |
| 10-30 | 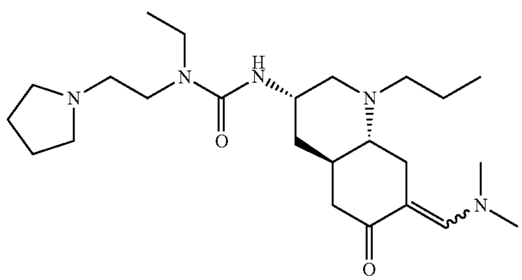 [SMILES: CCCN1C[C@@H](NC(=O)N(CC)CCN2CCCC2)C[C@@H]2CC(=O)C(=CN(C)C)C[C@H]21] |
| 10-31 | 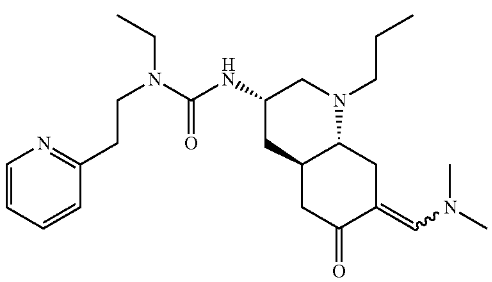 [SMILES: CCCN1C[C@@H](NC(=O)N(CC)CCc2ccccn2)C[C@@H]2CC(=O)C(=CN(C)C)C[C@H]21] |
| 10-32 | 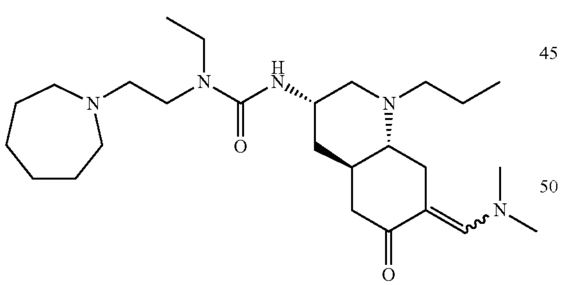 |
| 10-33 | 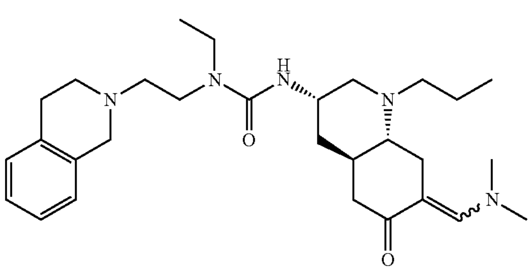 [SMILES: CCCN1C[C@@H](NC(=O)N(CC)CCN2CCc3ccccc3C2)C[C@@H]2CC(=O)C(=CN(C)C)C[C@H]21] |
| 10-34 | 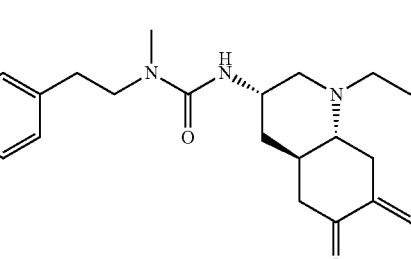 |
| 10-35 | |
| 10-36 | |
| 10-37 | |
| 10-38 | |

TABLE 8-continued

| Reference example | Structure |
|---|---|
| 10-39 | (structure) |
| 10-40 | (structure) |
| 10-41 | (structure) |
| 10-42 | (structure) |
| 10-43 | (structure) |
| 10-44 | (structure) |
| 10-45 | (structure) |
| 10-46 | (structure) |
| 10-47 | (structure) |
| 10-48 | (structure) |

TABLE 8-continued

| Reference example | Structure |
|---|---|
| 10-49 | (structure shown) |

The structures of the reference example 10-1 to 10-6 in Table 8 indicate absolute configuration, and the structures of the reference example 10-7 to 10-49 in Table 8 indicate relative configuration.

The physical data of reference examples 10-2 to 10-6 and reference examples 10-8 to 10-49 were shown below.

Reference Example 10-2

$^1$H-NMR (CDCl$_3$) δ ppm: 0.80-0.95 (6H, m), 1.10-1.25 (1H, m), 1.35-1.65 (4H, m), 1.70-2.15 (6H, m), 2.20-2.50 (11H, m), 2.55-2.70 (1H, m), 2.80-2.90 (1H, m), 3.05-3.30 (9H, m), 3.30-3.45 (1H, m), 3.95-4.05 (1H, m), 6.15-6.40 (1H, m), 7.50 (1H, s)

Reference Example 10-3

$^1$H-NMR (CDCl$_3$) δ ppm: 0.80-0.95 (9H, m), 1.10-1.25 (1H, m), 1.35-1.55 (2H, m), 1.65-2.15 (5H, m), 2.20-2.50 (12H, m), 2.55-2.70 (1H, m), 2.80-2.90 (1H, m), 2.90-3.30 (10H, m), 3.30-3.45 (1H, m), 3.95-4.05 (1H, m), 6.10-6.30 (1H, m), 7.50 (1H, s)

Reference Example 10-4

$^1$H-NMR (CDCl$_3$) δ ppm: 0.87 (3H, t, J=7.4 Hz), 1.04 (6H, t, J=7.3 Hz), 1.10-1.25 (1H, m), 1.35-1.55 (2H, m), 1.70-2.05 (3H, m), 2.05-2.15 (1H, m), 2.25-2.50 (4H, m), 2.50-2.70 (7H, m), 2.80-2.90 (1H, m), 2.90 (3H, s), 3.11 (6H, s), 3.15-3.40 (3H, m), 4.00-4.10 (1H, m), 5.90-6.05 (1H, m), 7.50 (1H, s)

Reference Example 10-5

MS (ESI, m/z): 337 (M+H)+

Reference Example 10-6

$^1$H-NMR (CDCl$_3$) δ ppm: 0.80 (3H, t, J=7.3 Hz), 1.05-1.45 (3H, m), 1.46 (3H, d, J=6.9 Hz), 1.65-1.80 (1H, m), 1.80-1.90 (1H, m), 1.90-2.10 (2H, m), 2.20-2.55 (5H, m), 2.60-2.70 (1H, m), 3.05-3.20 (7H, m), 3.90-4.00 (1H, m), 4.52 (1H, d, J=6.2 Hz), 4.65-4.80 (1H, m), 5.16 (1H, d, J=8.1 Hz), 7.20-7.40 (5H, m), 7.50 (1H, s)

Reference Example 10-8

$^1$H-NMR (CDCl$_3$) δ ppm: 0.83 (3H, t, J=7.3 Hz), 1.05-1.18 (1H, m), 1.28-1.56 (3H, m), 1.87-2.05 (3H, m), 2.07-2.17 (1H, m), 2.21-2.32 (2H, m), 2.35-2.42 (1H, m), 2.51-2.65 (1H, m), 2.74-2.83 (1H, m), 2.95 (3H, s), 3.04-3.09 (1H, m), 3.11 (6H, s), 3.98-4.08 (1H, m), 4.36-4.59 (2H, m), 5.42 (1H, d, J=8.3 Hz), 7.20-7.36 (5H, m), 7.48 (1H, s)

Reference Example 10-9

$^1$H-NMR (CDCl$_3$) δ ppm: 0.89 (3H, t, J=7.3 Hz), 1.11-1.22 (1H, m), 1.37-1.53 (2H, m), 1.72-2.14 (4H, m), 2.28-2.48 (4H, m), 2.60-2.74 (1H, m), 2.80-2.89 (1H, m), 2.90 (6H, s), 3.12 (6H, s), 3.16-3.25 (1H, m), 4.00-4.08 (1H, m), 5.41 (1H, d, J=8.3 Hz), 7.51 (1H, s)

Reference Example 10-10

$^1$H-NMR (CDCl$_3$) δ ppm: 0.89 (3H, t, J=7.3 Hz), 0.93 (3H, t, J=7.4 Hz), 1.10-1.22 (1H, m), 1.26-1.37 (2H, m), 1.38-1.57 (4H, m), 1.73-1.87 (1H, m), 1.89-2.13 (3H, m), 2.28-2.47 (4H, m), 2.61-2.72 (1H, m), 2.80-2.90 (1H, m), 2.87 (3H, s), 3.12 (6H, s), 3.12-3.31 (3H, m), 3.98-4.07 (1H, m), 5.39 (1H, d, J=8.0 Hz), 7.51 (1H, s)

Reference Example 10-11

$^1$H-NMR (CDCl$_3$) δ ppm: 0.88 (3H, t, J=7.4 Hz), 1.08-1.20 (1H, m), 1.36-1.55 (2H, m), 1.57-1.78 (1H, m), 1.84-1.93 (1H, m), 1.94-2.14 (2H, m), 2.27-2.48 (4H, m), 2.60-2.72 (1H, m), 2.75-2.89 (3H, m), 2.84 (3H, s), 3.12 (6H, s), 3.15-3.24 (1H, m), 3.39-3.55 (2H, m), 3.97-4.07 (1H, m), 5.36 (1H, d, J=8.0 Hz), 7.14-7.33 (5H, m), 7.51 (1H, s)

Reference Example 10-12

$^1$H-NMR (CDCl$_3$) δ ppm: 0.88 (3H, t, J=7.3 Hz), 1.10-1.23 (1H, m), 1.35-1.55 (2H, m), 1.74-2.15 (4H, m), 2.27-2.46 (4H, m), 2.60-2.73 (1H, m), 2.80-2.88 (1H, m), 2.93 (3H, s), 3.12 (6H, s), 3.16-3.25 (1H, m), 3.28-3.39 (1H, m), 3.35 (3H, s), 3.43-3.55 (3H, m), 3.95-4.04 (1H, m), 5.82 (1H, d, J=8.1 Hz), 7.51 (1H, s)

Reference Example 10-13

MS (ESI, m/z): 323 (M+H)+

Reference Example 10-14

MS (ESI, m/z): 428 (M+H)+

Reference Example 10-15

MS (ESI, m/z): 395 (M+H)+

Reference Example 10-16

MS (ESI, m/z): 363 (M+H)+

Reference Example 10-17

$^1$H-NMR (CDCl$_3$) δ ppm: 0.87 (3H, t, J=7.4 Hz), 1.03 (6H, t, J=7.2 Hz), 1.11-1.22 (1H, m), 1.35-1.54 (2H, m), 1.74-2.16 (4H, m), 2.26-2.68 (7H, m), 2.55 (4H, q, J=7.2 Hz), 2.81-2.93 (1H, m), 2.90 (3H, s), 3.11 (6H, s), 3.14-3.39 (3H, m), 3.97-4.07 (1H, m), 5.96 (1H, d, J=7.2 Hz), 7.50 (1H, s)

Reference Example 10-18

MS (ESI, m/z): 431 (M+H)+

Reference Example 10-19

$^1$H-NMR (CDCl$_3$) δ ppm: 0.83 (3H, t, J=7.3 Hz), 1.10-1.25 (4H, m), 1.35-1.55 (2H, m), 1.70-2.05 (3H, m), 2.05-2.15 (1H, m), 2.26 (6H, s), 2.30-2.50 (6H, m), 2.55-2.70 (1H, m), 2.80-2.90 (1H, m), 3.11 (6H, s), 3.15-3.40 (5H, m), 3.95-4.10 (1H, m), 6.25-6.40 (1H, m), 7.50 (1H, s)

Reference Example 10-20

MS (ESI, m/z): 470 (M+H)+

Reference Example 10-21

MS (ESI, m/z): 436 (M+H)+

Reference Example 10-22

MS (ESI, m/z): 422 (M+H)+

Reference Example 10-23

MS (ESI, m/z): 484 (M+H)+

Reference Example 10-24

$^1$H-NMR (CDCl$_3$) δ ppm: 0.89 (3H, t, J=7.3 Hz), 1.05-1.25 (4H, m), 1.35-1.65 (6H, m), 1.65-1.90 (1H, m), 1.90-2.15 (3H, m), 2.20 (6H, s), 2.20-2.45 (6H, m), 2.60-2.75 (1H, m), 2.80-2.90 (1H, m), 3.10-3.35 (11H, m), 4.00-4.10 (1H, m), 5.38 (1H, d, J=7.9 Hz), 7.51 (1H, s)

Reference Example 10-25

MS (ESI, m/z): 448 (M+H)+

Reference Example 10-26

$^1$H-NMR (CDCl$_3$) δ ppm: 0.80-0.95 (9H, m), 1.10-1.25 (4H, m), 1.35-1.55 (6H, m), 1.70-1.95 (2H, m), 1.95-2.05 (1H, m), 2.05-2.15 (1H, m), 2.25-2.50 (8H, m), 2.50-2.70 (3H, m), 2.80-2.90 (1H, m), 3.11 (6H, s), 3.15-3.40 (5H, m), 4.00-4.10 (1H, m), 5.91 (1H, d, J=7.8 Hz), 7.51 (1H, s)

Reference Example 10-27

$^1$H-NMR (CDCl$_3$) δ ppm: 0.87 (3H, t, J=7.3 Hz), 1.04 (6H, t, J=7.1 Hz), 1.10-1.25 (4H, m), 1.35-1.55 (2H, m), 1.70-2.15 (4H, m), 2.25-2.70 (11H, m), 2.80-2.90 (1H, m), 3.11 (6H, s), 3.15-3.40 (5H, m), 4.00-4.10 (1H, m), 6.05 (1H, d, J=7.5 Hz), 7.50 (1H, s)

Reference Example 10-28

MS (ESI, m/z): 463 (M+H)+

Reference Example 10-29

MS (ESI, m/z): 450 (M+H)+

Reference Example 10-30

MS (ESI, m/z): 434 (M+H)+

Reference Example 10-31

MS (ESI, m/z): 442 (M+H)+

Reference Example 10-32

MS (ESI, m/z): 462 (M+H)+

Reference Example 10-33

MS (ESI, m/z): 496 (M+H)+

Reference Example 10-34

MS (ESI, m/z): 377 (M+H)+

Reference Example 10-35

MS (ESI, m/z): 428 (M+H)+

Reference Example 10-36

MS (ESI, m/z): 428 (M+H)+

Reference Example 10-37

MS (ESI, m/z): 425 (M+H)+

Reference Example 10-38

MS (ESI, m/z): 450 (M+H)+

Reference Example 10-39

MS (ESI, m/z): 456 (M+H)+

Reference Example 10-40

MS (ESI, m/z): 464 (M+H)+

Reference Example 10-41

MS (ESI, m/z): 452 (M+H)+

Reference Example 10-42

MS (ESI, m/z): 466 (M+H)+

Reference Example 10-43

$^1$H-NMR (CDCl$_3$) δ ppm: 0.87 (3H, t, J=7.4 Hz), 1.05 (3H, t, J=7.2 Hz), 1.10-1.25 (4H, m), 1.35-1.55 (2H, m), 1.70-2.15 (4H, m), 2.27 (3H, s), 2.30-2.55 (8H, m), 2.55-2.70 (1H, m), 2.80-2.90 (1H, m), 3.11 (6H, s), 3.15-3.40 (5H, m), 3.95-4.10 (1H, m), 6.19 (1H, d, J=7.4 Hz), 7.50 (1H, s)

Reference Example 10-44

MS (ESI, m/z): 436 (M+H)+

Reference Example 10-45

MS (ESI, m/z): 422 (M+H)+

Reference Example 10-46

MS (ESI, m/z): 484 (M+H)+

Reference Example 10-47

MS (ESI, m/z): 464 (M+H)+

Reference Example 10-48

MS (ESI, m/z): 456 (M+H)+

Reference Example 10-49

MS (ESI, m/z): 484 (M+H)+

Example 1-1

3-[(5aR,8S,9aR)-2-Amino-6-propyl-5,5a,6,7,8,9,9a,10-octahydropyrido[2,3-g]quinazolin-8-yl]-1-[2-(dimethylamino)ethyl]-1-ethylurea (Compound 1-1)

To a mixture of 3-[(3S,4aR,8aR)-7-[(dimethylamino)methyiden]-6-oxo-1-propyldecahydroquinolin-3-yl]-1-[2-(dimethylamino)ethyl]-1-ethylurea (reference example 10-1) (110 mg) and ethanol (2.7 mL) was added guanidine carbonate (59 mg) while stirring at room temperature, and the mixture was refluxed for 16 hours. After cooling to room temperature, to the reaction mixture was added water, and extracted with ethyl acetate. After the separated organic layer was dried over anhydrous sodium sulfate, it was concentrated under reduced pressure. The residue was purified by aminopropyl silica gel column chromatography (eluent: 0%-15% methanol/ethyl acetate, gradient elution) to give the title compound (65 mg).

$^1$H-NMR (DMSO-d$_6$) δ ppm: 0.85 (3H, t, J=6.8 Hz), 1.00 (3H, t, J=6.8 Hz), 1.15-1.50 (3H, m), 1.70-1.90 (2H, m), 2.00-2.20 (7H, m), 2.20-2.45 (6H, m), 2.45-2.90 (3H, m), 2.95-3.40 (5H, m), 3.75-3.85 (1H, m), 6.25 (2H, s), 6.50-6.70 (1H, m), 8.00 (1H, s) [α]$_D^{25}$=−75.273° (c=0.44, MeOH)

Example 1-6

3-[(5aR,8S,9aR)-2-Amino-6-propyl-5,5a,6,7,8,9,9a,10-octahydropyrido[2,3-g]quinazolin-8-yl]-1-[(1S)-1-phenylethyl]urea (Compound 1-6)

To a mixture of 3-[(3S,4aR,8aR)-7-[(dimethylamino)methyiden]-6-oxo-1-propyldecahydroquinolin-3-yl]-1-[(1S)-1-phenylethyl]urea (reference example 10-6) (82 mg) and ethanol (2 mL) was added guanidine carbonate (44 mg) while stirring at room temperature, and the mixture was refluxed for 11 hours. After cooling to room temperature, the reaction mixture was diluted with ethanol (2 mL) and water (4 mL), and the solid was collected by filtration to give the title compound (53 mg).

$^1$H-NMR (CDCl$_3$) δ ppm: 0.82 (3H, t, J=7.3 Hz), 1.15-1.40 (3H, m), 1.46 (3H, d, J=6.8 Hz), 1.65-1.85 (1H, m), 1.90-2.05 (1H, m), 2.10-2.25 (1H, m), 2.25-2.55 (5H, m), 2.55-2.70 (2H, m), 2.90-3.00 (1H, m), 3.95-4.05 (1H, m), 4.57 (1H, d, J=6.3 Hz), 4.60-4.75 (1H, m), 4.83 (2H, s), 5.19 (1H, d, J=8.2 Hz), 7.20-7.40 (5H, m), 8.04 (1H, s) [α]$_D^{25}$=−97.875° (c=0.48, CHCl$_3$)

After dissolving a mixture of 3-[(5aR,8S,9aR)-2-amino-6-propyl-5,5a,6,7,8,9,9a,10-octahydropyrido[2,3-g]quinazolin-8-yl]-1-[(1S)-1-phenylethyl]urea (compound 1-6) (11 mg) and methanol (1.4 mL) by heating at 50° C., it was allowed to remain at room temperature for 16 hours to give a single crystal. The absolute configuration of a compound 1-6 was determined by X-ray crystallographic analysis of the obtained single crystal.

By determining the absolute configuration of 3-[(5aR,8S,9aR)-2-amino-6-propyl-5,5a,6,7,8,9,9a,10-octahydropyrido[2,3-g]quinazolin-8-yl]-1-[(1S)-1-phenylethyl]urea (compound 1-6), (3'S,4'aR,8'aR)-1'-propyloctahydro-1'H-spiro[1,3-dioxolane-2,6'-quinoline]-3'-carboxylic acid (reference example 5-1) as its starting material, was demonstrated the same configuration.

Example 1-7

3-[(5aR*,8S*,9aR*)-2-Amino-6-propyl-5,5a,6,7,8,9,9a,10-octahydropyrido[2,3-g]quinazolin-8-yl]-1,1-diethylurea (Compound 1-7)

To a mixture of 3-[(3S*,4aR*,8aR*)-7-[(dimethylamino)methyiden]-6-oxo-1-propyldecahydroquinolin-3-yl]-1,1-diethylurea (reference example 10-7) (42 mg) and ethanol (3.0 mL) was added guanidine carbonate (25 mg), and the mixture was refluxed for 4.5 hours. After cooling to room temperature, a saturated aqueous solution of sodium bicarbonate was added to the reaction mixture, and extracted with ethyl acetate. After the separated organic layer was dried over anhydrous sodium sulfate, it was concentrated under reduced pressure. The residue was purified by aminopropyl silica gel column chromatography (eluent: 0%-30% methanol/ethyl acetate, gradient elution) to give the title compound (28 mg).

$^1$H-NMR (CDCl$_3$) δ ppm: 0.91 (3H, t, J=7.3 Hz), 1.14 (6H, t, J=7.2 Hz), 1.23-1.34 (1H, m), 1.38-1.64 (2H, m), 1.74-1.91 (1H, m), 2.07-2.16 (1H, m), 2.18-2.28 (1H, m), 2.29-2.51 (4H, m), 2.62-2.80 (2H, m), 2.84-2.94 (1H, m), 3.00-3.10 (1H, m), 3.14-3.37 (4H, m), 3.97-4.15 (1H, m), 4.81 (2H, s), 5.40 (1H, d, J=7.9 Hz), 8.04 (1H, s)

Examples 1-2 to 1-5 and examples 1-8 to 1-48 were prepared in a manner similar to those as described in example 1-1 or example 1-7 using the corresponding 7-[(dimethylamino)methyliden]-6-oxodecahydroquinoline instead of 3-[(3S,4aR,8aR)-7-[(dimethylamino)methyliden]-6-oxo-1-propyldecahydroquinolin-3-yl]-1-[2-(dimethylamino)ethyl]-1-ethylurea. These were illustrated in Table 9.

TABLE 9

| Compound No. | Structure | |
|---|---|---|
| 1-1 | (chemical structure) | Chiral |

TABLE 9-continued
| Compound No. | Structure |
|---|---|
| 1-2 | 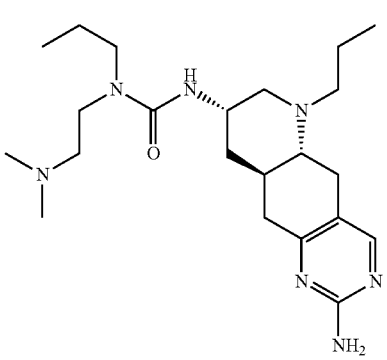 Chiral |
| 1-3 | 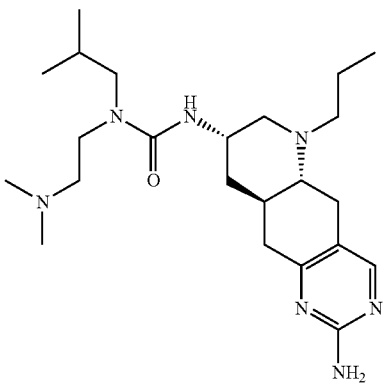 Chiral |
| 1-4 | 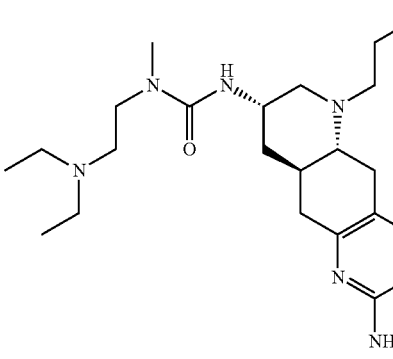 Chiral |
| 1-5 | 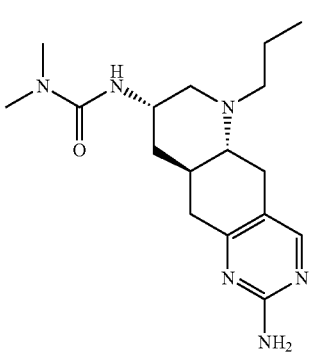 Chiral |
| 1-6 | 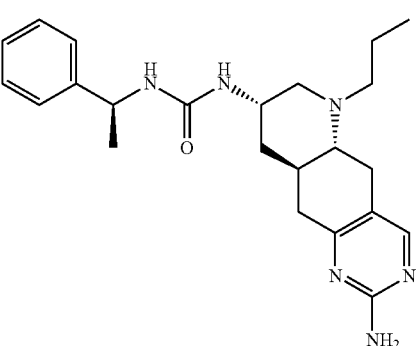 Chiral |
| 1-7 | 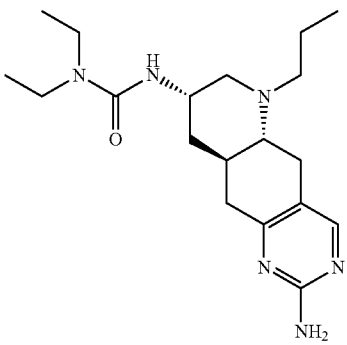 [SMILES: CCCN1C[C@@H](NC(=O)N(CC)CC)C[C@@H]2Cc3nc(N)ncc3C[C@H]21] |
| 1-8 | 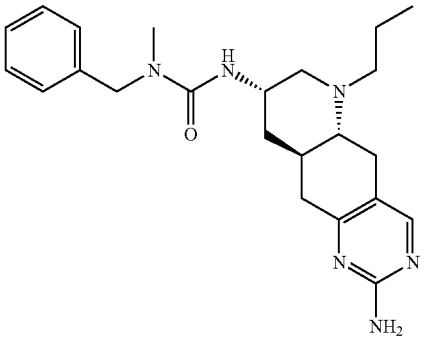 [SMILES: CCCN1C[C@@H](NC(=O)N(C)Cc2ccccc2)C[C@@H]2Cc3nc(N)ncc3C[C@H]21] |
| 1-9 | 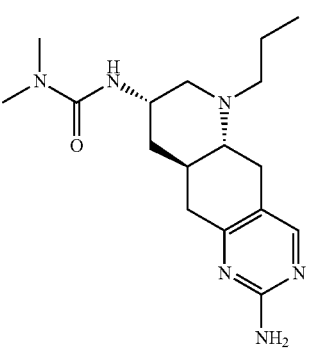 [SMILES: CCCN1C[C@@H](NC(=O)N(C)C)C[C@@H]2Cc3nc(N)ncc3C[C@H]21] |

TABLE 9-continued

| Compound No. | Structure |
| --- | --- |
| 1-10 | 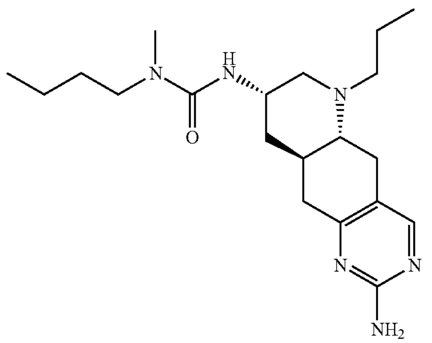 [SMILES: CCCCN(C)C(=O)N[C@H]1C[C@@H]2Cc3nc(N)ncc3C[C@H]2N(CCC)C1] |
| 1-11 | 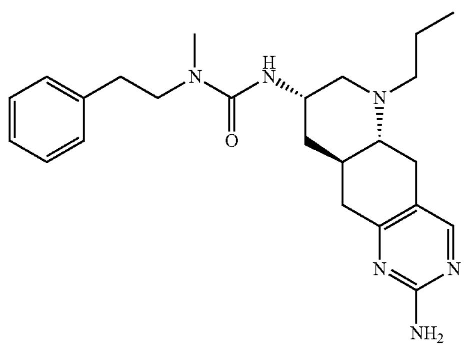 [SMILES: CCCN1C[C@@H](NC(=O)N(C)CCc2ccccc2)C[C@@H]2Cc3nc(N)ncc3C[C@H]21] |
| 1-12 | 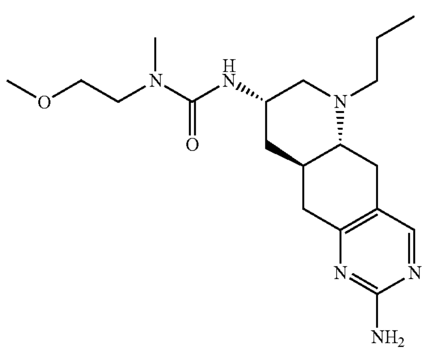 [SMILES: CCCN1C[C@@H](NC(=O)N(C)CCOC)C[C@@H]2Cc3nc(N)ncc3C[C@H]21] |
| 1-13 | 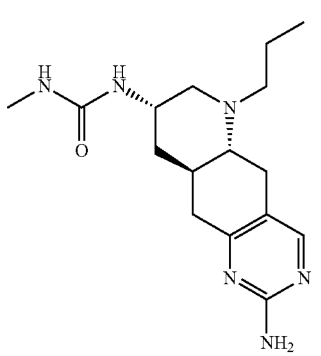 [SMILES: CCCN1C[C@@H](NC(=O)NC)C[C@@H]2Cc3nc(N)ncc3C[C@H]21] |
| 1-14 | 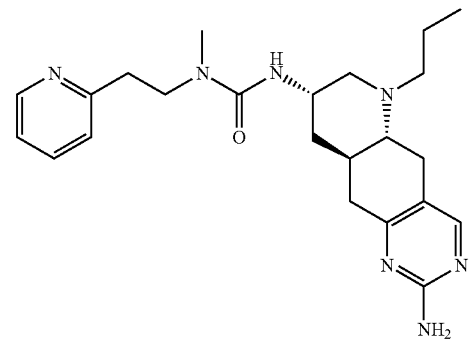 [SMILES: CCCN1C[C@@H](NC(=O)N(C)CCc2ccccn2)C[C@@H]2Cc3nc(N)ncc3C[C@H]21] |
| 1-15 | 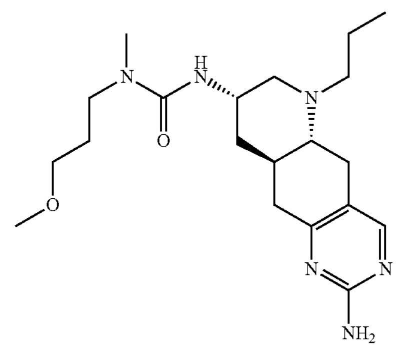 [SMILES: CCCN1C[C@@H](NC(=O)N(C)CCCOC)C[C@@H]2Cc3nc(N)ncc3C[C@H]21] |
| 1-16 | 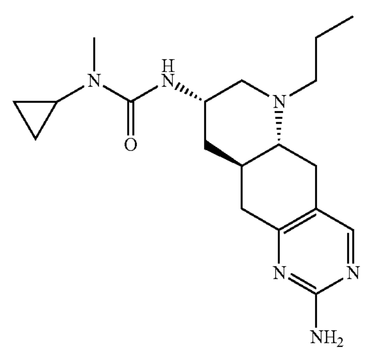 [SMILES: CCCN1C[C@@H](NC(=O)N(C)C2CC2)C[C@@H]2Cc3nc(N)ncc3C[C@H]21] |
| 1-17 | 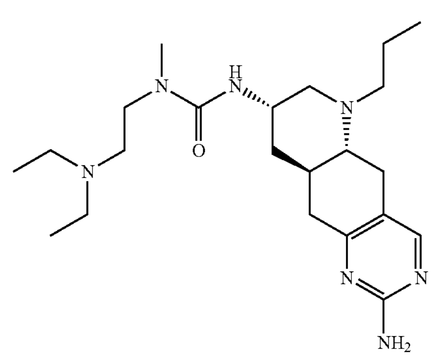 [SMILES: CCCN1C[C@@H](NC(=O)N(C)CCN(CC)CC)C[C@@H]2Cc3nc(N)ncc3C[C@H]21] |

TABLE 9-continued

| Compound No. | Structure |
|---|---|
| 1-18 | 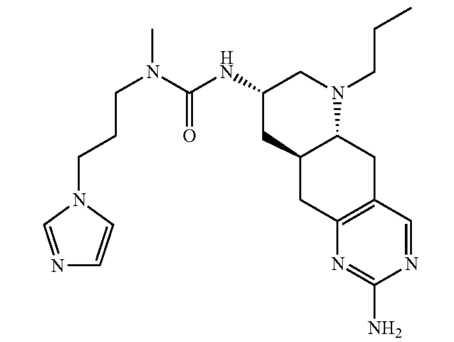 [SMILES: CCCN1C[C@@H](NC(=O)N(C)CCCn2ccnc2)C[C@@H]2Cc3nc(N)ncc3C[C@H]21] |
| 1-19 | 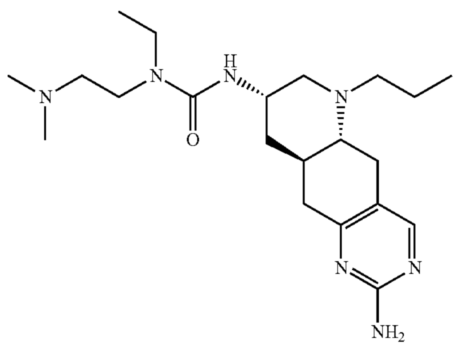 [SMILES: CCCN1C[C@@H](NC(=O)N(CC)CCN(C)C)C[C@@H]2Cc3nc(N)ncc3C[C@H]21] |
| 1-20 | 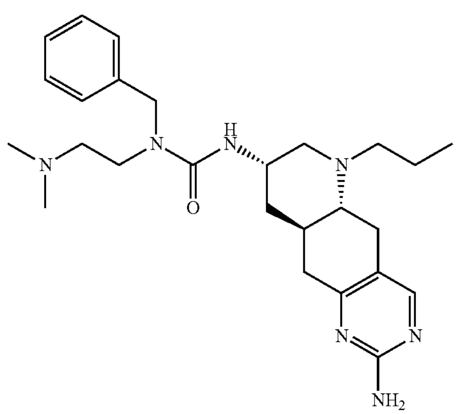 [SMILES: CCCN1C[C@@H](NC(=O)N(CCN(C)C)Cc2ccccc2)C[C@@H]2Cc3nc(N)ncc3C[C@H]21] |
| 1-21 | 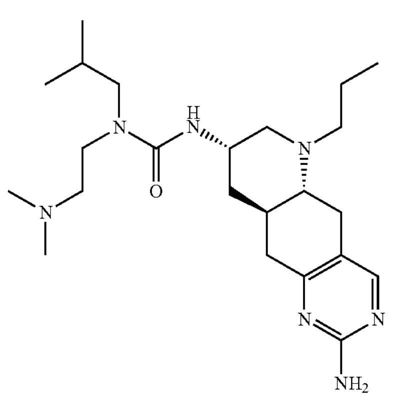 [SMILES: CCCN1C[C@@H](NC(=O)N(CCN(C)C)CC(C)C)C[C@@H]2Cc3nc(N)ncc3C[C@H]21] |
| 1-22 | |
| 1-23 | |
| 1-24 | |
| 1-25 | |

TABLE 9-continued
| Compound No. | Structure |
|---|---|
| 1-26 | 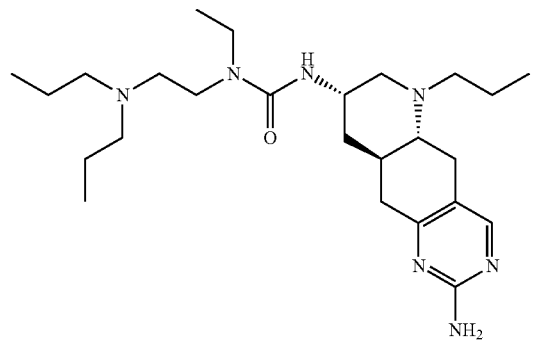 [SMILES: CCCN(CCC)CCN(CC)C(=O)N[C@H]1C[C@@H]2Cc3nc(N)ncc3C[C@H]2N(CCC)C1] |
| 1-27 | 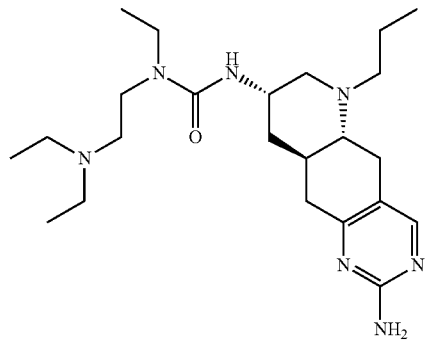 [SMILES: CCCN1C[C@@H](NC(=O)N(CC)CCN(CC)CC)C[C@@H]2Cc3nc(N)ncc3C[C@H]21] |
| 1-28 | 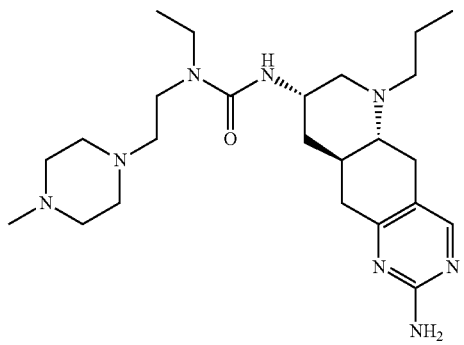 [SMILES: CCCN1C[C@@H](NC(=O)N(CC)CCN2CCN(C)CC2)C[C@@H]2Cc3nc(N)ncc3C[C@H]21] |
| 1-29 | 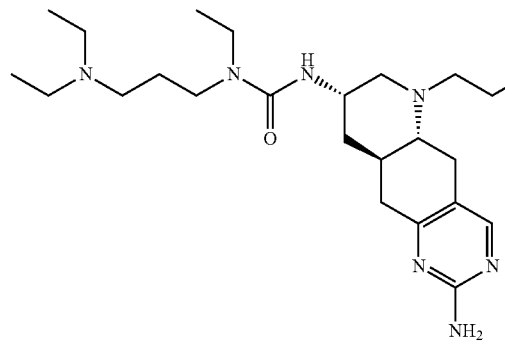 |
| 1-30 | 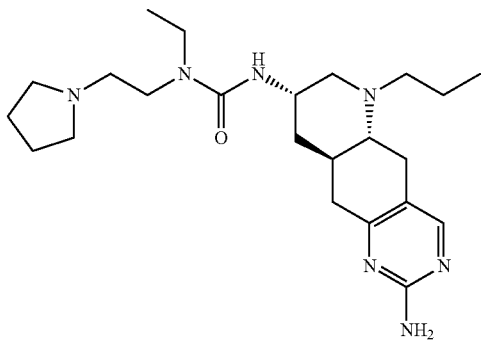 [SMILES: CCCN1C[C@@H](NC(=O)N(CC)CCN2CCCC2)C[C@@H]2Cc3nc(N)ncc3C[C@H]21] |
| 1-31 | 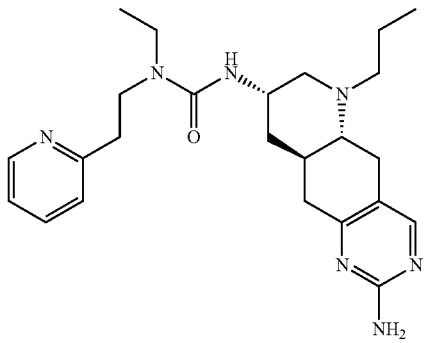 [SMILES: CCCN1C[C@@H](NC(=O)N(CC)CCc2ccccn2)C[C@@H]2Cc3nc(N)ncc3C[C@H]21] |
| 1-32 | 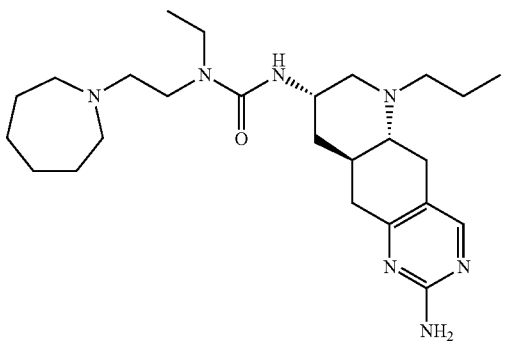 [SMILES: CCCN1C[C@@H](NC(=O)N(CC)CCN2CCCCCC2)C[C@@H]2Cc3nc(N)ncc3C[C@H]21] |
| 1-33 | 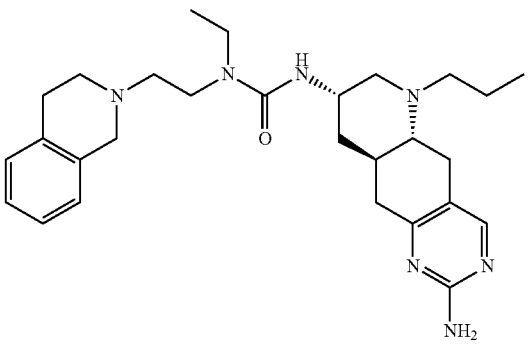 [SMILES: CCCN1C[C@@H](NC(=O)N(CC)CCN2CCc3ccccc3C2)C[C@@H]2Cc3nc(N)ncc3C[C@H]21] |

TABLE 9-continued

| Compound No. | Structure |
|---|---|
| 1-34 | 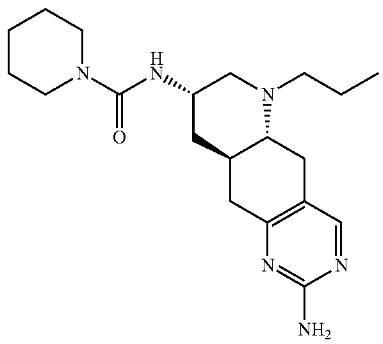 [SMILES: CCCN1C[C@@H](NC(=O)N2CCCCC2)C[C@@H]2Cc3nc(N)ncc3C[C@H]21] |
| 1-35 | 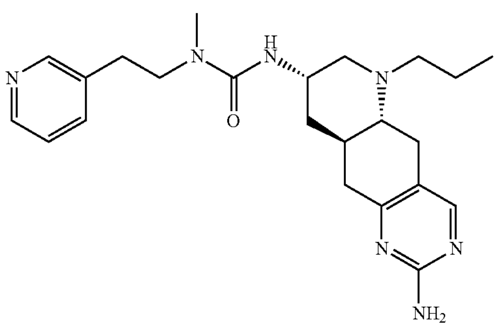 [SMILES: CCCN1C[C@@H](NC(=O)N(C)CCc2cccnc2)C[C@@H]2Cc3nc(N)ncc3C[C@H]21] |
| 1-36 | 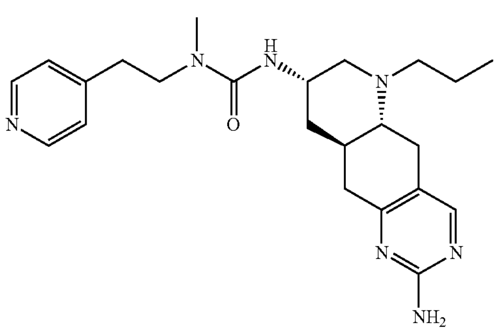 [SMILES: CCCN1C[C@@H](NC(=O)N(C)CCc2ccncc2)C[C@@H]2Cc3nc(N)ncc3C[C@H]21] |
| 1-37 | 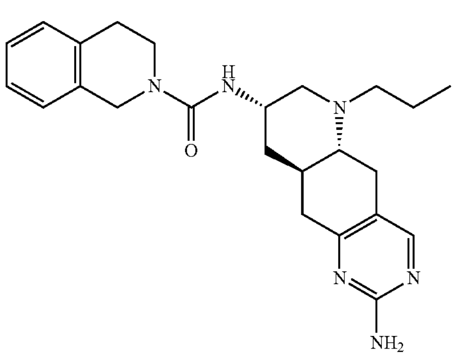 [SMILES: CCCN1C[C@@H](NC(=O)N2CCc3ccccc3C2)C[C@@H]2Cc3nc(N)ncc3C[C@H]21] |
| 1-38 | |
| 1-39 | |
| 1-40 | |
| 1-41 | |

TABLE 9-continued

| Compound No. | Structure |
|---|---|
| 1-42 | 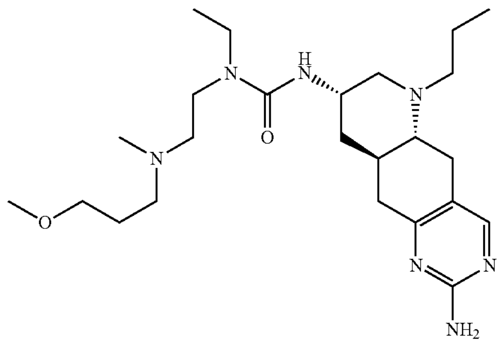 [SMILES: CCCN1C[C@@H](NC(=O)N(CC)CCN(C)CCCOC)C[C@@H]2Cc3nc(N)ncc3C[C@H]21] |
| 1-43 | 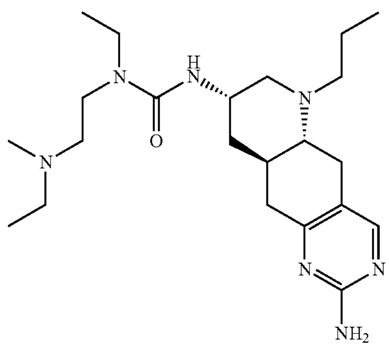 [SMILES: CCCN1C[C@@H](NC(=O)N(CC)CCN(C)CC)C[C@@H]2Cc3nc(N)ncc3C[C@H]21] |
| 1-44 | 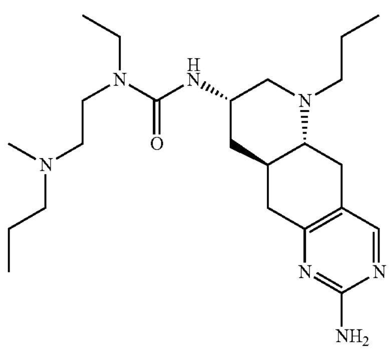 [SMILES: CCCN(C)CCN(CC)C(=O)N[C@H]1C[C@@H]2Cc3nc(N)ncc3C[C@H]2N(CCC)C1] |
| 1-45 | 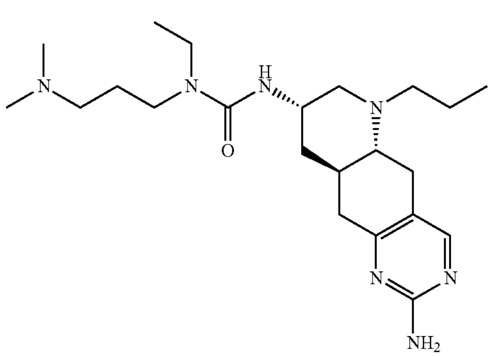 [SMILES: CCCN1C[C@@H](NC(=O)N(CC)CCCN(C)C)C[C@@H]2Cc3nc(N)ncc3C[C@H]21] |
| 1-46 | 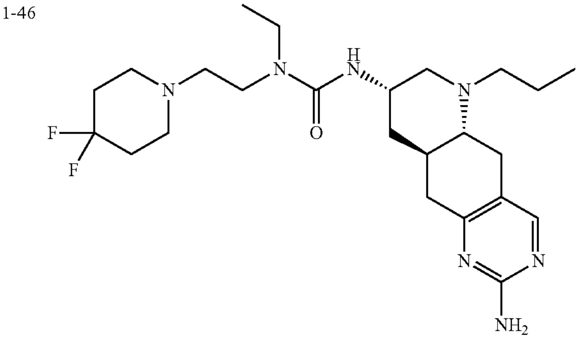 |
| 1-47 | 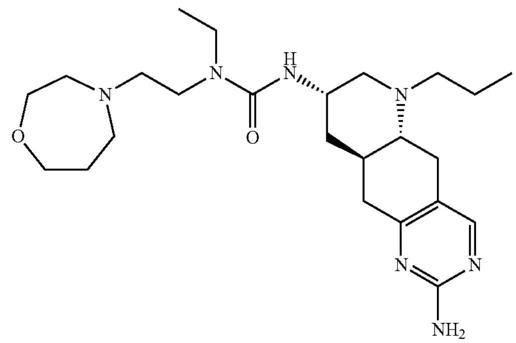 [SMILES: CCCN1C[C@@H](NC(=O)N(CC)CCN2CCCOCC2)C[C@@H]2Cc3nc(N)ncc3C[C@H]21] |
| 1-48 | 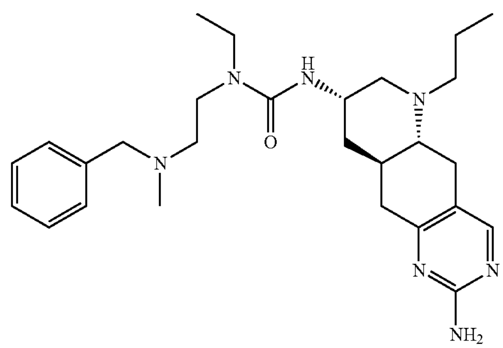 [SMILES: CCCN1C[C@@H](NC(=O)N(CC)CCN(C)Cc2ccccc2)C[C@@H]2Cc3nc(N)ncc3C[C@H]21] |

The structures of the compound 1-1 to 1-6 in Table 9 indicate absolute configuration, and the structures of the compound 1-7 to 1-48 in Table 9 indicate relative configuration.

The physical data of compounds 1-2 to 1-5 and compounds 1-8 to 1-48 were shown below.

Compound 1-2

$^1$H-NMR (CDCl$_3$) δ ppm: 0.89 (3H, t, J=7.4 Hz), 0.90 (3H, t, J=7.4 Hz), 1.20-1.35 (1H, m), 1.35-1.65 (4H, m), 1.75-1.90 (1H, m), 2.00-2.15 (1H, m), 2.15-2.30 (7H, m), 2.30-2.55 (6H, m), 2.60-2.75 (2H, m), 2.85-2.95 (1H, m), 2.95-3.30 (4H, m), 3.30-3.40 (1H, m), 4.00-4.10 (1H, m), 4.82 (2H, s), 6.35-6.55 (1H, m), 8.04 (1H, s) $[α]_D^{26}$=−79.422° (c=0.55, MeOH)

Compound 1-3

$^1$H-NMR (CDCl$_3$) δ ppm: 0.85-0.95 (9H, m), 1.20-1.35 (1H, m), 1.35-1.60 (2H, m), 1.75-2.00 (2H, m), 2.00-2.15 (1H, m), 2.15-2.30 (7H, m), 2.30-2.55 (6H, m), 2.60-2.75 (2H, m), 2.85-3.15 (4H, m), 3.15-3.30 (1H, m), 3.30-3.45 (1H, m), 4.00-4.10 (1H, m), 4.81 (2H, s), 6.25-6.45 (1H, m), 8.05 (1H, s) $[α]_D^{25}$=−73.762° (c=0.42, MeOH)

Compound 1-4

¹H-NMR (CDCl₃) δ ppm: 0.89 (3H, t, J=7.4 Hz), 1.02 (6H, t, J=7.2 Hz), 1.20-1.35 (1H, m), 1.35-1.55 (2H, m), 1.75-1.95 (1H, m), 2.00-2.10 (1H, m), 2.15-2.30 (1H, m), 2.30-2.60 (10H, m), 2.60-2.75 (2H, m), 2.80-2.95 (4H, m), 2.95-3.10 (1H, m), 3.15-3.40 (2H, m), 4.00-4.15 (1H, m), 4.81 (2H, s), 6.00-6.15 (1H, m), 8.05 (1H, s) $[\alpha]_D^{25}$=−73.600° (c=0.68, MeOH)

Compound 1-5

¹H-NMR (CDCl₃) δ ppm: 0.91 (3H, t, J=7.3 Hz), 1.20-1.35 (1H, m), 1.35-1.55 (2H, m), 1.75-1.95 (1H, m), 2.00-2.15 (1H, m), 2.15-2.30 (1H, m), 2.30-2.50 (4H, m), 2.60-2.80 (2H, m), 2.80-2.95 (7H, m), 3.00-3.10 (1H, m), 4.00-4.15 (1H, m), 4.81 (2H, brs), 5.43 (1H, d, J=7.9 Hz), 8.04 (1H, s) $[\alpha]_D^{25}$=−78.488° (c=0.46, MeOH)

Compound 1-8

¹H-NMR (CDCl₃) δ ppm: 0.86 (3H, t, J=7.4 Hz), 1.17-1.28 (1H, m), 1.30-1.51 (3H, m), 1.98-2.08 (1H, m), 2.08-2.22 (2H, m), 2.23-2.45 (3H, m), 2.51-2.68 (2H, m), 2.77-2.86 (1H, m), 2.88-2.96 (1H, m), 2.97 (3H, s), 4.02-4.11 (1H, m), 4.34-4.59 (2H, m), 4.81 (2H, s), 5.41 (1H, d, J=8.0 Hz), 7.11-7.18 (1H, m), 7.20-7.31 (4H, m), 8.01 (1H, s)

Compound 1-9

¹H-NMR (CDCl₃) δ ppm: 0.91 (3H, t, J=7.3 Hz), 1.23-1.34 (1H, m), 1.39-1.54 (2H, m), 1.79-1.91 (1H, m), 2.03-2.14 (1H, m), 2.17-2.28 (1H, m), 2.33-2.51 (4H, m), 2.61-2.79 (2H, m), 2.84-2.93 (1H, m), 2.90 (6H, s), 2.99-3.08 (1H, m), 4.03-4.11 (1H, m), 4.81 (2H, s), 5.43 (1H, d, J=7.8 Hz), 8.04 (1H, s)

Compound 1-10

¹H-NMR (CDCl₃) δ ppm: 0.91 (3H, t, J=7.3 Hz), 0.92 (3H, t, J=7.4 Hz), 1.21-1.38 (3H, m), 1.38-1.58 (4H, m), 1.77-1.90 (1H, m), 2.04-2.14 (1H, m), 2.17-2.27 (1H, m), 2.31-2.50 (4H, m), 2.60-2.79 (2H, m), 2.83-2.92 (1H, m), 2.87 (3H, s), 3.00-3.08 (1H, m), 3.11-3.31 (2H, m), 4.04-4.11 (1H, m), 4.81 (2H, s), 5.41 (1H, d, J=7.8 Hz), 8.04 (1H, s)

Compound 1-11

¹H-NMR (CDCl₃) δ ppm: 0.91 (3H, t, J=7.4 Hz), 1.20-1.32 (1H, m), 1.38-1.55 (2H, m), 1.63-1.78 (1H, m), 1.98-2.10 (1H, m), 2.15-2.27 (1H, m), 2.32-2.50 (4H, m), 2.60-2.76 (2H, m), 2.78-2.91 (3H, m), 2.84 (3H, s), 2.98-3.07 (1H, m), 3.37-3.55 (2H, m), 4.01-4.08 (1H, m), 4.82 (2H, s), 5.36 (1H, d, J=7.8 Hz), 7.11-7.32 (5H, m), 8.05 (1H, s)

Compound 1-12

¹H-NMR (CDCl₃) δ ppm: 0.91 (3H, t, J=7.4 Hz), 1.22-1.34 (1H, m), 1.38-1.54 (2H, m), 1.78-1.93 (1H, m), 2.02-2.12 (1H, m), 2.16-2.26 (1H, m), 2.32-2.49 (4H, m), 2.61-2.77 (2H, m), 2.84-2.92 (1H, m), 2.92 (3H, s), 2.99-3.08 (1H, m), 3.25-3.37 (1H, m), 3.32 (3H, s), 3.43-3.55 (3H, m), 4.00-4.07 (1H, m), 4.81 (2H, s), 5.90 (1H, d, J=8.3 Hz), 8.05 (1H, s)

Compound 1-13

¹H-NMR (DMSO-d₆) δ ppm: 0.85 (3H, t, J=7.4 Hz), 1.15-1.30 (1H, m), 1.30-1.50 (2H, m), 1.65-1.80 (2H, m), 2.05-2.20 (1H, m), 2.20-2.45 (4H, m), 2.55-2.80 (2H, m), 2.95-3.05 (1H, m), 3.75-3.90 (1H, m), 5.90 (1H, d, J=8.8 Hz), 5.95-6.10 (1H, m), 6.28 (2H, s), 7.99 (1H, s)

Compound 1-14

MS (ESI, m/z): 424 (M+H)+

Compound 1-15

¹H-NMR (CDCl₃) δ ppm: 0.90 (3H, t, J=7.4 Hz), 1.24-1.34 (1H, m), 1.39-1.55 (2H, m), 1.74-1.92 (3H, m), 2.03-2.12 (1H, m), 2.18-2.27 (1H, m), 2.33-2.51 (4H, m), 2.62-2.76 (2H, m), 2.85-2.92 (1H, m), 2.88 (3H, m), 2.99-3.08 (1H, m), 3.21-3.43 (4H, m), 3.30 (3H, s), 4.03-4.11 (1H, m), 4.80 (2H, s), 5.53 (1H, d, J=7.3 Hz), 8.04 (1H, s)

Compound 1-16

MS (ESI, m/z): 359 (M+H)+

Compound 1-17

¹H-NMR (CDCl₃) δ ppm: 0.89 (3H, t, J=7.4 Hz), 1.02 (6H, t, J=7.2 Hz), 1.24-1.35 (1H, m), 1.38-1.55 (2H, m), 1.76-1.92 (1H, m), 2.01-2.10 (1H, m), 2.17-2.28 (1H, m), 2.33-2.59 (10H, m), 2.61-2.73 (2H, m), 2.84-2.93 (1H, m), 2.90 (3H, s), 2.98-3.06 (1H, m), 3.18-3.38 (2H, m), 4.02-4.12 (1H, m), 4.81 (2H, s), 6.00-6.14 (1H, m), 8.04 (1H, s)

Compound 1-18

¹H-NMR (CDCl₃) δ ppm: 0.91 (3H, t, J=7.3 Hz), 1.22-1.37 (1H, m), 1.38-1.55 (2H, m), 1.75-1.90 (1H, m), 1.95-2.12 (3H, m), 2.19-2.28 (1H, m), 2.34-2.54 (4H, m), 2.60-2.77 (2H, m), 2.82 (3H, s), 2.84-2.93 (1H, m), 2.98-3.09 (1H, m), 3.20-3.32 (1H, m), 3.38-3.49 (1H, m), 3.93-4.02 (2H, m), 4.03-4.12 (1H, m), 4.81 (2H, s), 5.44 (1H, d, J=8.0 Hz), 6.93-6.98 (1H, m), 7.02-7.07 (1H, m), 7.49 (1H, s), 8.05 (1H, s)

Compound 1-19

¹H-NMR (CDCl₃) δ ppm: 0.90 (3H, t, J=7.3 Hz), 1.12 (3H, t, J=7.1 Hz), 1.20-1.35 (1H, m), 1.35-1.55 (2H, m), 1.75-1.95 (1H, m), 2.00-2.15 (1H, m), 2.15-2.30 (7H, m), 2.30-2.55 (6H, m), 2.60-2.75 (2H, m), 2.85-2.95 (1H, m), 2.95-3.10 (1H, m), 3.15-3.40 (4H, m), 4.00-4.10 (1H, m), 4.83 (2H, s), 6.40-6.60 (1H, m), 8.04 (1H, s)

Compound 1-20

¹H-NMR (CDCl₃) δ ppm: 0.86 (3H, t, J=7.3 Hz), 1.15-1.55 (4H, m), 1.70-3.10 (18H, m), 3.20-3.40 (1H, m), 3.45-3.60 (1H, m), 3.95-4.15 (1H, m), 4.41 (1H, d, J=16.4 Hz), 4.54 (1H, d, J=16.4 Hz), 4.86 (2H, s), 6.32 (1H, br), 7.05-7.20 (1H, m), 7.20-7.35 (4H, m), 8.01 (1H, s)

Compound 1-21

¹H-NMR (CDCl₃) δ ppm: 0.85-0.95 (9H, m), 1.20-1.35 (1H, m), 1.35-1.60 (2H, m), 1.75-1.95 (2H, m), 2.00-2.15 (1H, m), 2.15-2.30 (7H, m), 2.30-2.55 (6H, m), 2.60-2.75 (2H, m), 2.85-3.15 (4H, m), 3.15-3.30 (1H, m), 3.30-3.45 (1H, m), 4.00-4.10 (1H, m), 4.81 (2H, s), 6.25-6.45 (1H, m), 8.04 (1H, s)

Compound 1-22

¹H-NMR (CDCl₃) δ ppm: 0.89 (3H, t, J=7.4 Hz), 0.90 (3H, t, J=7.4 Hz), 1.20-1.35 (1H, m), 1.35-1.65 (4H, m), 1.75-1.90 (1H, m), 2.00-2.15 (1H, m), 2.15-2.30 (7H, m), 2.30-2.55 (6H, m), 2.60-2.75 (2H, m), 2.85-2.95 (1H, m), 2.95-3.30 (4H, m), 3.30-3.40 (1H, m), 4.00-4.10 (1H, m), 4.81 (2H, s), 6.35-6.50 (1H, m), 8.04 (1H, s)

Compound 1-23

MS (ESI, m/z): 480 (M+H)+

Compound 1-24

¹H-NMR (CDCl₃) δ ppm: 0.91 (3H, t, J=7.4 Hz), 1.13 (3H, t, J=7.1), 1.25-1.35 (1H, m), 1.35-1.60 (6H, m), 1.75-1.90 (1H, m), 2.05-2.15 (1H, m), 2.15-2.30 (9H, m), 2.30-2.50 (4H, m), 2.60-2.70 (2H, m), 2.70-2.80 (1H, m), 2.85-2.95 (1H, m), 3.00-3.10 (1H, m), 3.10-3.35 (4H, m), 4.00-4.10 (1H, m), 4.82 (2H, s), 5.40 (1H, d, J=8.0 Hz), 8.04 (1H, s)

Compound 1-25

¹H-NMR (CDCl₃) δ ppm: 0.91 (3H, t, J=7.4 Hz), 1.13 (3H, t, J=7.2 Hz), 1.20-1.35 (1H, m), 1.35-1.60 (8H, m), 1.75-1.95 (1H, m), 2.05-2.15 (1H, m), 2.15-2.30 (1H, m), 2.30-2.55 (10H, m), 2.60-2.2.80 (2H, m), 2.85-2.95 (1H, m), 3.00-3.10 (1H, m), 3.15-3.45 (4H, m), 4.00-4.15 (1H, m), 4.81 (2H, s), 5.61 (1H, d, J=7.9 Hz), 8.05 (1H, s)

Compound 1-26

¹H-NMR (CDCl₃) δ ppm: 0.84 (6H, t, J=7.4 Hz), 0.90 (3H, t, J=7.4 Hz), 1.13 (3H, t, J=7.1 Hz), 1.20-1.35 (1H, m), 1.35-1.55 (6H, m), 1.70-1.95 (1H, m), 2.00-2.15 (1H, m), 2.15-2.30 (1H, m), 2.30-2.60 (10H, m), 2.60-2.75 (2H, m), 2.85-2.95 (1H, m), 2.95-3.10 (1H, m), 3.15-3.40 (4H, m), 4.00-4.15 (1H, m), 4.80 (2H, s), 5.85-6.00 (1H, m), 8.04 (1H, s)

Compound 1-27

¹H-NMR (CDCl₃) δ ppm: 0.89 (3H, t, J=7.3 Hz), 1.02 (6H, t, J=7.2 Hz), 1.13 (3H, t, J=7.1 Hz), 1.25-1.35 (1H, m), 1.35-1.55 (2H, m), 1.75-1.95 (1H, m), 2.00-2.15 (1H, m), 2.15-2.30 (1H, m), 2.30-2.60 (10H, m), 2.60-2.75 (2H, m), 2.85-2.95 (1H, m), 2.95-3.10 (1H, m), 3.15-3.40 (4H, m), 4.00-4.15 (1H, m), 4.80 (2H, s), 6.05-6.30 (1H, m), 8.04 (1H, s)

Compound 1-28

¹H-NMR (CDCl₃) δ ppm: 0.91 (3H, t, J=7.3 Hz), 1.14 (3H, t, J=7.1 Hz), 1.25-1.35 (1H, m), 1.40-1.60 (2H, m), 1.75-1.95 (1H, m), 2.05-2.15 (1H, m), 2.15-2.80 (20H, m), 2.85-2.95 (1H, m), 3.00-3.10 (1H, m), 3.15-3.50 (4H, m), 4.00-4.15 (1H, m), 4.80 (2H, s), 5.45-5.65 (1H, m), 8.04 (1H, s)

Compound 1-29

¹H-NMR (DMSO-d₆) δ ppm: 0.80-0.95 (9H, m), 1.01 (3H, t, J=7.2 Hz), 1.10-1.90 (7H, m), 2.00-2.50 (12H, m), 2.60-2.90 (2H, m), 2.95-3.35 (5H, m), 3.75-3.90 (1H, m), 5.44 (1H, d, J=7.6 Hz), 6.25 (2H, s), 7.99 (1H, s)

Compound 1-30

¹H-NMR (DMSO-d₆) δ ppm: 0.85 (3H, t, J=7.3 Hz), 1.01 (3H, t, J=7.1 Hz), 1.10-1.90 (12H, m), 2.00-2.60 (9H, m), 2.60-2.90 (2H, m), 2.95-3.10 (1H, m), 3.10-3.30 (4H, m), 3.75-3.90 (1H, m), 5.91 (1H, d, J=8.0 Hz), 6.26 (2H, s), 7.99 (1H, s)

Compound 1-31

¹H-NMR (CDCl₃) δ ppm: 0.89 (3H, t, J=7.5 Hz), 1.10 (3H, t, J=7.2 Hz), 1.25-1.35 (1H, m), 1.35-1.55 (2H, m), 1.75-1.90 (1H, m), 2.00-2.15 (1H, m), 2.15-2.30 (1H, m), 2.30-2.50 (4H, m), 2.60-2.80 (2H, m), 2.85-2.95 (1H, m), 2.95-3.10 (3H, m), 3.10-3.35 (2H, m), 3.50-3.70 (2H, m), 4.00-4.15 (1H, m), 4.81 (2H, s), 5.56 (1H, d, J=8.0 Hz), 7.05-7.15 (1H, m), 7.15-7.20 (1H, m), 7.50-7.60 (1H, m), 8.04 (1H, s), 8.45-8.55 (1H, m)

Compound 1-32

¹H-NMR (DMSO-d₆) δ ppm: 0.85 (3H, t, J=7.2 Hz), 1.02 (3H, t, J=7.2 Hz), 1.10-1.90 (13H, m), 2.00-2.40 (6H, m), 2.40-2.90 (8H, m), 2.90-3.40 (5H, m), 3.75-3.90 (1H, m), 5.80 (1H, d, J=7.6 Hz), 6.26 (2H, s), 7.99 (1H, s)

Compound 1-33

¹H-NMR (DMSO-d₆) δ ppm: 0.83 (3H, t, J=7.2 Hz), 1.04 (3H, t, J=6.8 Hz), 1.10-1.50 (3H, m), 1.55-1.85 (3H, m), 2.00-2.45 (7H, m), 2.50-3.00 (10H, m), 3.10-3.40 (2H, m), 3.50-3.70 (2H, m), 3.75-3.90 (1H, m), 5.905 (1H, d, J=7.6 Hz), 6.23 (2H, s), 6.90-7.05 (4H, m), 7.92 (1H, s)

Compound 1-34

¹H-NMR (CDCl₃) δ ppm: 0.91 (3H, t, J=7.3 Hz), 1.20-1.35 (1H, m), 1.35-1.65 (5H, m), 1.70-2.00 (4H, m), 2.00-2.15 (1H, m), 2.15-2.30 (1H, m), 2.30-2.55 (4H, m), 2.60-2.80 (2H, m), 2.80-2.95 (1H, m), 2.95-3.10 (1H, m), 3.20-3.40 (4H, m), 4.05-4.15 (1H, m), 4.88 (2H, m), 5.50 (1H, d, J=7.8 Hz), 8.04 (1H, s)

Compound 1-35

¹H-NMR (CDCl₃) δ ppm: 0.91 (3H, t, J=7,3 Hz), 1.20-1.35 (1H, m), 1.35-1.60 (2H, m), 1.65-1.85 (1H, m), 2.00-2.10 (1H, m), 2.15-2.30 (1H, m), 2.30-2.55 (4H, m), 2.60-2.80 (2H, m), 2.80-2.95 (6H, m), 2.95-3.10 (1H, m), 3.40-3.60 (2H, m), 4.00-4.10 (1H, m), 4.81 (2H, s), 5.39 (1H, d, J=7.8 Hz), 7.15-7.25 (1H, m), 7.50-7.60 (1H, m), 8.05 (1H, s), 8.40-8.45 (1H, m), 8.45-8.50 (1H, m)

Compound 1-36

¹H-NMR (CDCl₃) δ ppm: 0.91 (3H, t, J=7.4 Hz), 1.20-1.35 (1H, m), 1.35-1.65 (2H, m), 1.70-1.90 (1H, m), 2.00-2.15 (1H, m), 2.15-2.30 (1H, m), 2.30-2.55 (4H, m), 2.60-2.80 (2H, m), 2.80-2.95 (6H, m), 3.00-3.10 (1H, m), 3.40-3.65 (2H, m), 4.00-4.10 (1H, m), 4.81 (2H, s), 5.40 (1H, d, J=7.9 Hz), 7.10-7.20 (2H, m), 8.05 (1H, s), 8.45-8.55 (2H, m)

Compound 1-37

¹H-NMR (DMSO-d₆) δ ppm: 0.85 (3H, t, J=7.2 Hz), 1.20-1.50 (3H, m), 1.70-2.00 (2H, m), 2.05-2.60 (6H, m), 2.60-2.95 (4H, m), 2.95-3.05 (1H, m), 3.40-3.60 (2H, m), 3.80-4.00 (1H, m), 4.40-4.55 (2H, m), 5.77 (1H, d, J=7.2 Hz), 6.23 (2H, s), 7.15 (4H, s), 7.99 (1H, s)

Compound 1-38

¹H-NM (CDCl₃) δ ppm: 0.91 (3H, t, J=7.3 Hz), 1.20-1.55 (3H, m), 1.75-1.95 (3H, m), 2.00-2.15 (1H, m), 2.15-2.30 (1H, m), 2.30-2.55 (4H, m), 2.60-2.80 (8H, m), 2.85-2.95 (4H, m), 2.95-3.10 (1H, m), 3.20-3.50 (2H, m), 3.65-3.80 (4H, m), 4.00-4.15 (1H, m), 4.81 (2H, s), 5.66 (1H, d, J=8.0 Hz), 8.04 (1H, s)

Compound 1-39

¹H-NMR (CDCl₃) δ ppm: 0.88 (3H, t, J=7.3 Hz), 1.15-1.30 (1H, m), 1.30-1.65 (3H, m), 1.90-2.05 (1H, m), 2.05-2.50 (5H, m), 2.50-2.70 (2H, m), 2.75-3.00 (8H, m), 3.30-3.60 (4H, m), 4.00-4.10 (1H, m), 4.82 (2H, s), 5.57 (1H, d, J=8.0 Hz), 6.55-6.65 (1H, m), 6.65-6.75 (2H, m), 7.05-7.20 (2H, m), 8.00 (1H, s)

Compound 1-40

¹H-NMR (CDCl₃) δ ppm: 0.89 (3H, t, J=7.3 Hz), 0.95-1.05 (12H, m), 1.13 (3H, t, J=7.2 Hz), 1.20-1.35 (1H, m), 1.35-1.55 (2H, m), 1.75-1.95 (1H, m), 2.00-2.15 (1H, m), 2.15-2.30 (1H, m), 2.30-2.75 (8H, m), 2.85-3.40 (8H, m), 4.05-4.15 (1H, m), 4.81 (2H, s), 5.70 (1H, d, J=7.8 Hz), 8.04 (1H, s)

Compound 1-41

¹H-NMR (CDCl₃) δ ppm: 0.90 (3H, t, J=7.4 Hz), 1.13 (3H, t, J=7.2 Hz), 1.20-1.35 (1H, m), 1.35-1.60 (2H, m), 1.75-1.95 (1H, m), 2.00-2.15 (1H, m), 2.15-2.75 (14H, m), 2.85-2.95 (1H, m), 2.95-3.10 (1H, m), 3.15-3.40 (7H, m), 3.40-3.50 (2H, m), 4.00-4.15 (1H, m), 4.86 (2H, s), 6.02 (1H, d, J=7.6 Hz), 8.04 (1H, s)

Compound 1-42

¹H-NMR (CDCl₃) δ ppm: 0.90 (3H, t, J=7.4 Hz), 1.13 (3H, t, J=7.0 Hz), 1.20-1.35 (1H, m), 1.35-1.60 (2H, m), 1.65-1.75 (2H, m), 1.75-1.95 (1H, m), 2.00-2.15 (1H, m), 2.15-2.30 (1H, m), 2.30-2.55 (4H, m), 2.30-2.55 (8H, m), 2.60-2.75 (2H, m), 2.85-2.95 (1H, m), 2.95-3.10 (1H, m), 3.15-3.40 (9H, m), 4.00-4.15 (1H, m), 4.85 (2H, s), 6.13 (1H, d, J=7.2 Hz), 8.04 (1H, s)

Compound 1-43

¹H-NMR (CDCl₃) δ ppm: 0.89 (3H, t, J=7.4 Hz), 1.02 (3H, t, J=7.2 Hz), 1.13 (3H, t, J=7.2 Hz), 1.20-1.35 (1H, m), 1.35-1.55 (2H, m), 1.75-1.95 (1H, m), 2.00-2.10 (1H, m), 2.15-2.30 (4H, m), 2.30-2.55 (8H, m), 2.60-2.75 (2H, m), 2.85-2.95 (1H, m), 2.95-3.10 (1H, m), 3.15-3.40 (4H, m), 4.00-4.10 (1H, m), 4.83 (2H, s), 6.25-6.40 (1H, m), 8.05 (1H, s)

Compound 1-44

MS (ESI, m/z): 432 (M+H)+

Compound 1-45

¹H-NMR (CDCl₃) δ ppm: 0.90 (3H, t, J=7.3 Hz), 1.13 (3H, t, J=7.1 Hz), 1.20-1.35 (1H, m), 1.35-1.60 (2H, m), 1.60-1.75 (2H, m), 1.75-1.95 (1H, m), 2.00-2.55 (14H, m), 2.60-2.80 (2H, m), 2.85-2.95 (1H, m), 2.95-3.10 (1H, m), 3.10-3.40 (4H, m), 4.00-4.15 (1H, m), 4.92 (2H, s), 5.73 (1H, d, J=7.4 Hz), 8.04 (1H, s)

Compound 1-46

¹H-NMR (CDCl₃) δ ppm: 0.91 (3H, t, J=7.3 Hz), 1.15 (3H, t, J=3H, t, J=7.2 Hz), 1.25-1.35 (1H, m), 1.35-1.60 (2H, m), 1.75-1.90 (1H, m), 1.90-2.05 (4H, m), 2.05-2.15 (1H, m), 2.15-2.30 (1H, m), 2.30-2.45 (3H, m), 2.45-2.80 (9H, m), 2.85-2.95 (1H, m), 3.00-3.10 (1H, m), 3.15-3.45 (4H, m), 4.00-4.15 (1H, m), 4.81 (2H, s), 5.59 (1H, d, J=7.9 Hz), 8.04 (1H, s)

Compound 1-47

$^1$H-NMR (CDCl$_3$) δ ppm: 0.91 (3H, t, J=7.3 Hz), 1.14 (3H, t, J=7.2 Hz), 1.20-1.35 (1H, m), 1.35-1.60 (2H, m), 1.70-1.95 (3H, m), 2.05-2.15 (1H, m), 2.15-2.30 (1H, m), 2.30-2.45 (3H, m), 2.45-2.55 (1H, m), 2.60-2.85 (8H, m), 2.85-2.95 (1H, m), 3.00-3.10 (1H, m), 3.15-3.45 (4H, m), 3.65-3.75 (2H, m), 3.76 (2H, t, J=6.1 Hz), 4.00-4.15 (1H, m), 4.84 (2H, s), 5.71 (1H, d, J=7.9 Hz), 8.04 (1H, s)

Compound 1-48

$^1$H-NMR (CDCl$_3$) δ ppm: 0.88 (3H, t, J=7.4 Hz), 1.07 (3H, t, J=7.0 Hz), 1.20-1.35 (1H, m), 1.35-1.55 (2H, m), 1.70-1.90 (1H, m), 2.00-2.15 (1H, m), 2.15-2.30 (4H, m), 2.30-2.55 (6H, m), 2.55-2.70 (2H, m), 2.80-2.95 (1H, m), 2.95-3.05 (1H, m), 3.10-3.40 (4H, m), 3.45-3.60 (2H, m), 4.00-4.15 (1H, m), 4.84 (2H, s), 5.97 (1H, d, J=7.8 Hz), 7.15-7.35 (5H, m), 8.01 (1H, s)

Example 2-1

3-[(5aR*,8S*,9aR*)-2-Amino-6-propyl-5,5a,6,7,8,9,9a,10-octahydropyrido[2,3-g]quinazolin-8-yl]-1-ethyl-1-[2-(methylamino)ethyl]urea (Compound 2-1)

To a mixture of 3-[(5'R*,8S*,9aR*)-2-amino-6-propyl-5,5a,6,7,8,9,9a,10-octahydropyrido[2,3-g]quinazolin-8-yl]-1-{2-[benzyl(methyl)amino]ethyl}-1-ethylurea (example 1-48) (73 mg), ethanol (3.0 mL) and methanol (2.0 mL) was added 10% palladium-carbon (50 mg), and the mixture was stirred at room temperature for 7.5 hours under a hydrogen atmosphere. The mixture diluted with ethyl acetate was passed through a layer of Celite (registered mark), the filtrate was concentrated under reduced pressure. The residue was purified by aminopropyl silica gel column chromatography (eluent: 0%-20% methanol/ethyl acetate, gradient elution) to give the title compound (43 mg). The structure was illustrated in Table 10.

$^1$H-NMR (CDCl$_3$) δ ppm: 0.91 (3H, t, J=7.5 Hz), 1.13 (3H, t, J=7.2 Hz), 1.20-1.35 (1H, m), 1.35-1.95 (3H, m), 2.00-2.15 (1H, m), 2.15-2.30 (1H, m), 2.30-2.50 (7H, m), 2.60-2.80 (4H, m), 2.85-2.95 (1H, m), 2.95-3.10 (1H, m), 3.15-3.45 (4H, m), 4.00-4.15 (1H, m), 4.83 (2H, s), 6.07 (1H, d, J=7.6 Hz), 8.04 (1H, s)

Example 3-1

3-[(5aR*,8S*,9aR*)-2-Amino-6-(prop-2-en-1-yl)-5,5a,6,7,8,9,9a,10-octahydropyrido[2,3-g]quinazolin-8-yl]-1-[2-(dimethylamino)ethyl]-1-ethylurea (Compound 3-1)

To a mixture of 3-[(3S*,4aR*,8aR*)-1-benzyl-7-[(dimethylamino)methyiden]-6-oxodecahydroquinolin-3-yl]-1-[2-(dimethylamino)ethyl]-1-ethylurea (reference example 10-48) (443 mg) and ethanol (9.7 mL) was added guanidine carbonate (211 mg) while stirring at room temperature, and the mixture was heated at 90° C. and refluxed for 12 hours. After cooling to room temperature, to the reaction mixture was added water, and extracted with ethyl acetate. After the separated organic layer was dried over anhydrous sodium sulfate, it was concentrated under reduced pressure. The residue was purified by aminopropyl silica gel column chromatography (eluent: 0%-10% methanol/ethyl acetate, gradient elution) to give 3-[(5aR*,8S*,9aR*)-2-amino-6-benzyl-5,5a,6,7,8,9,9a,10-octahydropyrido[2,3-g]quinazolin-8-yl]-1-[2-(dimethylamino)ethyl]-1-ethylurea (248 mg).

$^1$H-NMR (CDCl$_3$) δ ppm: 1.11 (3H, t, J=7.1 Hz), 1.25-1.40 (1H, m), 1.85-2.05 (1H, m), 2.05-2.15 (1H, m), 2.20-2.35 (8H, m), 2.35-2.50 (3H, m), 2.50-2.65 (1H, m), 2.65-2.75 (1H, m), 2.75-2.85 (1H, m), 3.05-3.40 (6H, m), 3.90-4.00 (1H, m), 4.15-4.25 (1H, m), 4.87 (2H, s), 5.85-6.10 (1H, m), 7.20-7.40 (5H, m), 8.06 (1H, s)

To a mixture of 3-[(5aR*,8S*,9aR*)-2-amino-6-benzyl-5,5a,6,7,8,9,9a,10-octahydropyrido[2,3-g]quinazolin-8-yl]-1-[2-(dimethylamino)ethyl]-1-ethylurea (217 mg) and ethanol (5.0 mL) was added 10% palladium-carbon (100 mg), and the mixture was stirred at room temperature for 6.5 hours under a hydrogen atmosphere. The mixture diluted with ethyl acetate was passed through a layer of Celite (registered mark), the filtrate was concentrated under reduced pressure. To a mixture of the residue and ethanol (5.0 mL) was added 10% palladium-carbon (100 mg), the mixture was stirred at room temperature for 14.5 hours under a hydrogen atmosphere. The mixture diluted with ethyl acetate was passed through a layer of Celite (registered mark), the filtrate was concentrated under reduced pressure. The residue was purified by aminopropyl silica gel column chromatography (eluent: 0%-20% methanol/ethyl acetate, gradient elution) to give 3-[(5aR*,8S*,9aR*)-2-amino-5,5a,6,7,8,9,9a,10-octahydropyrido[2,3-g]quinazolin-8-yl]-1-[2-(dimethylamino)ethyl]-1-ethylurea (111 mg).

$^1$H-NMR (CDCl$_3$) δ ppm: 1.12 (3H, t, J=7.2 Hz), 1.30-1.45 (1H, m), 2.00-2.15 (1H, m), 2.25 (6H, s), 2.30-2.50 (4H, m), 2.55-2.80 (3H, m), 2.90-3.00 (1H, m), 3.00-3.10 (1H, m), 3.15-3.45 (4H, m), 3.95-4.05 (1H, m), 4.85 (2H, s), 6.90-7.15 (1H, m), 8.01 (1H, s)

To a mixture of 3-[(5aR*,8S*,9aR*)-2-amino-5,5a,6,7,8,9,9a,10-octahydropyrido[2,3-g]quinazolin-8-yl]-1-[2-(dimethylamino)ethyl]-1-ethylurea (86 mg) and toluene (2.5 mL) was added tetrakistriphenylphosphine palladium (0) (14 mg), followed by allyl acetate (0.051 mL), and the mixture was stirred at room temperature for 3 hours. To the reaction mixture was added water, the mixture was extracted with methylene chloride/2-propanol mixed solvent (methylene chloride:2-propanol=3:1). After the separated organic layer was dried over anhydrous sodium sulfate, it was concentrated under reduced pressure. The residue was purified by aminopropyl silica gel column chromatography (eluent: 0%-10% methanol/ethyl acetate, gradient elution) to give the title compound (55 mg). The structure was illustrated in Table 10.

$^1$H-NMR (CDCl$_3$) δ ppm: 1.12 (3H, t, J=7.2 Hz), 1.20-1.35 (1H, m), 1.80-1.95 (1H, m), 2.00-2.15 (1H, m), 2.20-2.30 (7H, m), 2.30-2.60 (5H, m), 2.60-2.75 (1H, m), 2.85-2.95 (1H, m), 3.00-3.50 (7H, m), 4.00-4.15 (1H, m), 4.85 (2H, s), 5.15-5.30 (2H, m), 5.75-5.95 (1H, m), 6.55-6.75 (1H, m), 8.03 (1H, s)

TABLE 10

| Compound No. | Structure |
| --- | --- |
| 2-1 | (structure) |

TABLE 10-continued

| Compound No. | Structure |
|---|---|
| 3-1 | (structure shown) |

The structures of the compound 2-1 and 3-1 in Table 10 indicate relative configuration.

Test Example 1

Identification Test of Stimulating Activities on Human Dopamine $D_2$ Receptor

1) Construction of Human Dopamine $d_2$ Receptor Expression Plasmid

The PCR was performed using forward primer depicted as sequence ID No. 1, reverse primer depicted as sequence ID No. 2 and Herculase (Stratagene) as template of human brain cDNA (Japan Becton, Dickinson and Company). The PCR product was inserted into a plasmid (pcDNA3.1/V5-His-Topo (registered mark), Invitrogen). The PCR product-inserted plasmid was transformed in *E. coli* (One Shot TOP10 Chemically Competent, Invitrogen). That *E. coli* was incubated in LB agar medium contained 50 µg/mL ampicillin for a day. A selected colony was incubated in LB medium contained 50 µg/mL ampicillin and PCR product-inserted plasmid was purified with QIAprep Spin Miniprep Kit (QIAGEN). The base sequence of protein expression site in the plasmid (sequence ID No. 3) accorded to the base sequence of human dopamine $D_2$ receptor (NM_000795) registered on the public database (NCBI), except 1 base. But, the sequence of amino acids translated by base sequence of that plasmid accorded to it of human dopamine $D_2$ receptor (NM_000795) registered on NCBI completely. Therefore, the proteins induced from this plasmid were identified with human dopamine $D_2$ receptor. The pcDNA3.1/V5-His-Topo (registered mark) that the base sequence depicted as sequence ID No. 3 was inserted, was identified as human dopamine $D_2$ receptor expression plasmid.

2) Preparation of Human Dopamine $d_2$ Receptor Expression Cells (1) Cell Culture HEK 293 cells (Dainippon Sumitomo Pharma Co., Ltd.) were cultured in 5% $CO_2$ incubator at 37° C. in D-MEM (Dulbecco's Modified Eagle Medium) liquid medium (low glucose, pyruvic acid and L-glutamine were contained, Invitrogen) in which penicillin-streptomycin solution (Invitrogen, final concentration: 100 U/mL as penicillin, 100 µg/mL as streptomycin) and fetal bovine serum (final concentration: 10%).

(2) The Passage of Cells

Mostly confluent HEK293 cells were washed with PBS (Phosphate Buffered Saline, Invitrogen), followed by exfoliation with 0.05% trypsin-EDTA (Invitrogen) and they were suspended with above-mentioned liquid medium. After centrifuging, the supernatant was removed and the cells were diluted with medium and cell number was counted. After that, the cells were scattered at appropriate cell concentration.

(3) Establishment of HEK293 Cells Expressed Human Dopamine $D_2$ Receptor Stably Human dopamine $D_2$ receptor expression plasmid was digested with ScaI and changed to linear plasmid. The linear plasmid was transfected in HEK293 cells using lipofection method (Lipofectamine (registered mark) 2000 (Invitrogen)). After procurement of neomycin resistant cell using 1 mg/mL Geneticin (registered mark)(Invitrogen), cell line was selected according to the method of 3) seeing below.

3) Identification and Selection of HEK293 Cells Expressed Human Dopamine $D_2$ Receptor Stably (1) The Passage of Cells Mostly confluent HEK293 cells expressed human dopamine $D_2$ receptor stably were washed with PBS, followed by exfoliation with 0.05% trypsin-EDTA and D-MEM liquid medium (low glucose, pyruvic acid and L-glutamine were contained) containing Geneticin (registered mark) (final concentration: 0.1 mg/mL) as antibiotics and fetal bovine serum (final concentration: 10%) was added. After centrifuging, the supernatant was removed and the cells were diluted with above-mentioned liquid medium. After counting cell number, the cells were scattered at appropriate concentration.

(2) Preparation of Cells

Mostly confluent HEK293 cells expressed human dopamine $D_2$ receptor stably were washed with PBS, followed by exfoliation with 0.05% trypsin-EDTA and the cells were suspended in D-MEM liquid medium (phenol red-free, low glucose and pyruvic acid were contained, Invitrogen) containing fetal bovine serum (final concentration: 10%) and GlutaMax (registered mark) I (Invitrogen, final concentration: 2 mM). The suspension was scattered at $5 \times 10^4$ cells/100 µL/well on poly-D-lysine-coated 96-well microplate (BD BioCoat (registered mark), Japan Becton, Dickinson and Company). The scattered cells were cultured in 5% $CO_2$ incubator at 37° C. To change signal of human dopamine $D_2$ receptor cAMP reaction interacting $G_{i/o}$ protein to carcium reaction, pLEC1-Gqo5-HA (Molecular Devices) was transfected in that cells according to the procedure seeing below.

(3) Transfection of pLEC1-Gqo5-HA pLEC1-Gqo5-HA and Lipofectamine (registered mark) 2000 were diluted to 0.008 g/L and 0.016 g/L each other with OPTI-MEM (registered mark) I Reduced-Serum Medium (Invitrogen) and incubated at room temperature. After incubation, the pLEC1-Gqo5-HA-diluted solution and Lipofectamine (registered mark) 2000-diluted solution were mixed at an equal volume and incubated at room temperature to form a complex. The complex was dispensed at 50 µL/well on the cells prepared above. The cells were incubated in 5% $CO_2$ incubator at 37° C. for 2 days and used in measurement of intracellular calcium concentration.

(4) Identification with Measurement of Intracellular Calcium Concentration

The measurement of intracellular calcium concentration induced by each test compound was performed using the forced expression cells mentioned above. Each dimethyl sulfoxide (DMSO) solution contained test compounds at 30 mM was diluted to appropriate concentration with assay buffer (Hank's Balanced Salt Solution (HBSS, Invitrogen), 20 mM HEPES (Invitrogen), 1.3 mM calcium chloride, 0.5 mM magnesium chloride and 0.4 mM magnesium sulfate were contained, pH7.4).

The forced expression cells were washed with assay buffer, and 100 μL/well of fluorescent calcium indicator (Fluo-4 NW Calcium Assay Kit (Molecular Probes™)) was added and incubated in 5% $CO_2$ incubator at 37° C. After incubation, 50 μL/well of each test compound was added, and the concentration of intracellular calcium was measured as fluorescent signal with FlexStation (registered mark) II (Molecular Devices). The cell line expressed human dopamine $D_2$ receptor stably having good response was named as hD2R#7 cells.

4) Preparation of Membrane Homogenates from $hD_2R$#7 Cells (1) The Passage of $hD_2R$#7 Cells Mostly confluent $hD_2R$#7 cells were washed with PBS, followed by exfoliation with 0.05% trypsin-EDTA and D-MEM liquid medium (low glucose, pyruvic acid and L-glutamine were contained) containing Geneticin (registered mark) (final concentration: 0.1 mg/mL) as antibiotics and fetal bovine serum (final concentration: 10%) were added. After centrifuging, the supernatant was removed and the cells were diluted with above-mentioned liquid medium. After counting cell number, the cells were scattered at appropriate concentration.

(2) Preparation of Membrane Homogenates from $hD_2R$#7 Cells

The cells, which were grown to confluence in 150 mm dishes (IWAKI), were harvested with isotonic buffer (50 mM Tris (Sigma), 2 mM ethylenediamine-tetraacetic acid (Invitrogen), and 125 mM sodium chloride (Wako Pure Chemicals), pH 7.4) and centrifuged at 1880×g and 4° C. for 10 minutes, and the cell pellets were then suspended in isotonic buffer. After being subjected to one cycle of freezing and thawing, the cells were centrifuged at 1880×g and 4° C. for 10 minutes, and the cell pellets were suspended in isotonic buffer. The cells were centrifuged at 1880×g and 4° C. for 10 minutes, and the cell pellets were suspended in isotonic buffer and homogenate buffer (10 mM sodium bicarbonate (Nacalai) and 5 mM ethylenediamine-tetraacetic acid, pH 7.5). The volume ratio of isotonic-to-homogenate buffer was 2. The cells were sonicated and centrifuged at 1880×g and 4° C. for 10 minutes, and the supernatants were ultracentrifuged at 80000×g and 4° C. for 30 minutes. The final cell pellets were suspended in homogenate buffer containing protease inhibitor cocktail (Nacalai) and stored at −80° C. until use. The protein concentration was determined using BCA Protein Assay Kit (Pierce) in accordance with the manufacturer's instructions.

5) Determination of Stimulating Activities of Human Dopamine $D_2$ Receptor

The stimulating activities of human dopamine D2 receptor was determined by measuring the binding potential of [$^{35}$S]-guanosine 5'-[gamma-thio]triphosphate ([$^{35}$S]GTPγS, PerkinElmer) according to the method described by Newman-Tancredi A. et al. (Naunyn-Schmiedeberg's Arch Pharmacol, 1999, vol. 359, pp. 447-453) with a minor modification. Test compounds and dopamine hydrochloride (Fluka) as positive control were dissolved in dimethyl sulfoxide (CARLBIOCHEM), resulting in 30 mM. The both compounds were diluted with assay buffer (50 mM Tris, 100 mM sodium chloride, 5 mM magnesium chloride (Nacalai), 1 mM ethylenediamine-tetraacetic acid, 1 mM dithiothreitol (Wako Pure Chemicals), 10 μM guanosine diphosphate (Wako Pure Chemicals) and 0.5% bovine serum albumin (Sigma), pH 7.4) to a final concentration of 100 pM (only test compounds), 1 nM, 10 nM, 100 nM, 1 μM, 10 μM and 100 μM (only dopamine hydrochloride). The above membrane homogenates and [$^{35}$S]GTPγS were diluted with assay buffer to a final concentration of 0.06 mg/mL and 0.6 nM, respectively. The serial diluted compounds (50 μL), the diluted membrane homogenates (50 μL) and the diluted [$^{35}$S]GTPγS (50 μL) were mixed on multi-screen 96-well plate (Millipore) and shaken lightly at room temperature for 60 minutes. The reaction was terminated by vacuum filtration with three times washes of ice-cold wash buffer (50 mM Tris, 100 mM sodium chloride, 5 mM magnesium chloride, and 1 mM ethylenediamine-tetraacetic acid, pH 7.4). After drying the bottoms of the plate at 60° C., MicroScinti-40 (PerkinElmer) (30 μL) was added in the plate. The tops of the plate were sealed by TopSeal-A (PerkinElmer), and the radioactivity was determined in a TopCount NXT (registered mark)(PerkinElmer) after shaking lightly for 5-10 minutes. The data was analyzed by nonlinear regression and sigmoidal dose-response curve fitting using GraphPad PRISM 4.0 (GraphPad Software), and values of $EC_{50}$ (concentration of the compound producing half the maximal effect of the compound) were calculated. The data was presented as mean value (n=2). As comparative examples, ropinirole as non-ergot dopamine $D_2$ receptor agonist and [(5aR*,8S*,9aR*)-2-amino-6-propyl-5,5a,6,7,8,9,9a,10-octahydropyrido[2,3-g]quinazolin-8-yl]methanol (comparative example 1) described in patent literature 7, were examined in a similar fashion. These results were shown in Table 11.

TABLE 11

| Compound No. | $EC_{50}$ (μmol/L) |
|---|---|
| 1-1 | 0.064 |
| 1-2 | 0.252 |
| 1-4 | 0.111 |
| 1-5 | 0.009 |
| 1-11 | 0.019 |
| 1-12 | 0.043 |
| 1-13 | 0.161 |
| 1-16 | 0.093 |
| 1-23 | 0.223 |
| 1-25 | 0.126 |
| 1-33 | 0.093 |
| 1-34 | 0.063 |
| 1-36 | 0.034 |
| 1-37 | 0.010 |
| 1-39 | 0.039 |
| 1-41 | 0.116 |
| Ropinirole | 0.892 |
| Comparative example 1 | 2.904 |

These results clearly showed that the compounds of the present invention exhibited potent stimulating activities of human dopamine $D_2$ receptor in proportion to comparative example 1.

Test Example 2

Identification Test of Stimulating Activities on Human Serotonin $5-HT_{2B}$ Receptor 1) Construction of Human Serotonin $5-HT_{2B}$ Receptor Expression Plasmid The PCR was performed using forward primer depicted as sequence ID No. 4, reverse primer depicted as sequence ID No. 5 and KOD-Plus-Ver.2 (TOYOBO) as template of human brain hippocampus cDNA (Clontech). The PCR product was inserted into a plasmid (pcDNA3.1/V5-His- Topo (registered mark)). The PCR product-inserted plasmid was transformed in E. coli (One Shot TOP10 Chemically Competent). That E. coli was incubated in LB agar medium contained 50 μg/mL ampicillin for a day. A selected colony was incubated in LB medium contained 50 μg/mL ampicillin and PCR product-inserted plasmid was purified with QIAprep Spin Miniprep Kit (QIAGEN). The base sequence of protein expression site in the plasmid (sequence ID No. 6) accorded to the base sequence of human serotonin 5-$HT_{2B}$ receptor (NM_000867) registered on the public database (NCBI) completely. Therefore, the proteins induced from this vector were identified with human serotonin 5-$HT_{2B}$ receptor. The pcDNA3.1/V5-His-Topo (registered mark) that the base sequence depicted as sequence ID No. 6 was inserted, was identified as human serotonin 5-$HT_{2B}$ receptor expression plasmid.

2) Preparation of Human Serotonin 5-$HT_{2B}$ Receptor Expression Cells (1) Cell Culture HEK 293 cells were cultured in 5% $CO_2$ incubator at 37° C. in D-MEM liquid medium (low glucose, pyruvic acid and L-glutamine were contained) in which penicillin-streptomycin solution (final concentration: 100 U/mL as penicillin, 100 μg/mL as streptomycin) as antibiotics and fetal bovine serum (final concentration: 10%) were contained.

(2) The Passage of Cells

Mostly confluent HEK293 cells were washed with PBS, followed by exfoliation with 0.05% trypsin-EDTA and above-mentioned liquid medium was added. After centrifuging, the supernatant was removed and the cells were diluted with medium. After counting cell number of the diluted cells, the cells were scattered at appropriate cell concentration.

(3) Preparation of Cells

Mostly confluent HEK293 cells were washed with PBS, followed by exfoliation with 0.05% trypsin-EDTA and the cells were suspended in D-MEM liquid medium (phenol red-free, low glucose, pyruvic acid were contained) containing fetal bovine serum (final concentration: 10%) and GlutaMax (registered mark) I (final concentration: 2 mM). The suspension was scattered at $5\times10^4$ cells/100 μL/well on poly-D-lysine-coated 96-well microplate (BD BioCoat (registered mark)). The scattered cells were cultured in 5% $CO_2$ incubator at 37° C. Human serotonin 5-$HT_{2B}$ receptor expression plasmid was transfected in that cells according to the procedure seeing below.

(4) Transfection of Human Serotonin 5-$HT_{2B}$ Receptor Plasmid

Human serotonin 5-$HT_{2B}$ receptor expression plasmid and Lipofectamine (registered mark) 2000 (Invitrogen) were diluted to 0.008 g/L and 0.016 g/L each other with OPTI-MEM (registered mark) I Reduced-Serum Medium and incubated at room temperature. After incubation, the human serotonin 5-$HT_{2B}$ receptor expression plasmid-diluted liquid and Lipofectamine (registered mark) 2000-diluted liquid were mixed at an equal volume and incubated at room temperature to form a complex. The complex was dispensed at 50 μL/well on the cells prepared above. The cells were incubated in 5% $CO_2$ incubator at 37° C. for 2 days. After incubation, the cells were used as human serotonin 5-$HT_{2B}$ receptor forced expression cells for measurement of intracellular calcium concentration.

3) Determination of Stimulating Activities of Human Serotonin 5-$HT_{2B}$ Receptor The stimulating activities of human serotonin 5-$HT_{2B}$ receptor was determined by measuring of intracellular calcium concentration. The 30 mM dimethyl sulfoxide (DMSO) solution contained test compounds or serotonin hydrochloride (Sigma) as positive control, was diluted with assay buffer ((HBSS), 20 mM HEPES, 1.3 mM calcium chloride, 0.5 mM magnesium chloride and 0.4 mM magnesium sulfate were contained, pH7.4) to appropriate concentration.

The forced expression cells were washed with assay buffer, and 100 μL/well of fluorescent calcium indicator (Fluo-4 NW Calcium Assay Kit) was added and incubated in 5% $CO_2$ incubator at 37° C. After incubation, 50 μL/well of each test compound was added, and the concentration of intracellular calcium was measured as fluorescent signal with FlexStation (registered mark) II (Molecular Devices). The data was analyzed by nonlinear regression and sigmoidal dose-response curve fitting using GraphPad PRISM 4.0, and values of $EC_{50}$ (concentration of the compound producing half the maximal effect of the compound) were calculated. The data was presented as mean value (n=2). As comparative example, ropinirole as non-ergot dopamine $D_2$ receptor agonist, was examined in a similar fashion. These results were shown in Table 12.

TABLE 12

| Compound No. | $EC_{50}$ (μmol/L) |
|---|---|
| 1-1 | >10 |
| 1-2 | >10 |
| 1-4 | >10 |
| 1-11 | >10 |
| 1-12 | >10 |
| 1-13 | >10 |
| 1-16 | >10 |
| 1-23 | >10 |
| 1-25 | >10 |
| 1-33 | >10 |
| 1-34 | >10 |
| 1-36 | >10 |
| 1-37 | >10 |
| 1-39 | >10 |
| 1-41 | >10 |
| Ropinirole | 2.593 |

These results clearly showed that the compounds of the present invention exhibited extremely minor stimulating activities of human serotonin 5-$HT_{2B}$ receptor as compared with ropinirole.

Test Example 3

The Drug Efficiency Evaluation in Unilateral 6-Hydroxydopamine-Lesioned Hemi-Parkisonian Rats 1) Materials The following materials were used:

6-hydroxydopamine hydrochloride (6-OHDA, Sigma); desipramine hydrochloride (desipramine, Sigma); L-ascorbic acid (Sigma); pentobarbital sodium (somnopentyl injection, Kyoritsu Seiyaku); R-(−)-apomorphine hydrochloride hemihydrate (apomorphine, Sigma); ropinirole hydrochloride (ropinirole; Sequoia); 0.5% methyl cellulose solution (Wako Pure Chemicals); N,N-Dimethylacetamide (DMA, Wako Pure Chemicals); hydrochloric acid (Wako Pure Chemicals); distilled water (Otsuka Pharmaceutical Factory, Inc.); physiological saline (Otsuka Pharmaceutical Factory, Inc.).

6-OHDA was dissolved at 2 mg/mL in a physiolosical saline solution containing 0.2% L-ascorbic acid. Desipramine was dissolved at 10 mg/mL in a physiolosical saline solution in a hot-water bath. Apomorphine was dissolved at 0.1 mg/mL in a physiolosical saline solution. Ropinirole was dissolved in distilled water. Test compounds were dissolved in a solution containing 2% DMA, 100 or 200 mol % hydrochloric acid, and 98% of a 0.5% methyl cellulose solution.

2) Preparation of 6-OHDA-lesioned Model

Preparation of 6-OHDA-lesioned model was performed according to the method described by Koga K. et al. (Eur J Pharmacol, 2000, vol. 408, P. 249-255) with a minor modification. Male Sprague-Dawley rats (6-weeks-old, Charles River Laboratories Japan Inc.) were anaesthetized with intraperitoneal somnopentyl (45 mg/kg) injection and placed in a stereotaxic frame (Narishige). In order to prevent 6-OHDA-induced damage of noradrenergic neurons, desipramine (25 mg/kg) was intraperitoneally injected 30 minutes before the 6-OHDA injection. After the bregma identification via a middle calvarial incision, the skull was drilled using a dental drill at the site of 6-OHDA injection. The lesion was made by injecting 6-OHDA (8 μg in 4 μL at a speed of 1 μL/minute) unilaterally into the left medial forebrain bundle by using a injection cannula (30 gauge needle) connected to a microsyringe (Hamilton) (the lesion coordinates; A/P −2.5 mm, L/M −1.8 mm, and V/D −8.0 mm, from the bregma point and surface of the skull). The cannula was carefully removed from the animal after keeping placed on the lesion site for 5 minutes. The skull was filled its hole with dental cement, disinfected, and the scalp incision was surgically sutured. Animals recovered from anesthesia were housed as usual until the day of the experiment.

3) Determining of Contralateral Rotational Behavior

Three weeks after the lesion, rats were tested on the basis of their contralateral rotational behavior (single rotation was defined as a 360° turn) in response to 0.1 mg/kg apomorphine given subcutaneously. For behavioral observation, rats were placed in plastic cylinders of a diameter of 30 cm, and its contralateral rotational behaviors were videotaped and quantified by rat-rotation auto counting system R-RACS (Kissei Wellcom). On the experimental day, animals were fasted overnight, and test compounds were orally administrated at doses of 10 mg/kg. The drug potency was measured until up to 24 hours after administration as the number of contralateral rotation. Duration of the response was defined as a total time period except for a time period that the animal exhibited less than 10 counts of rotation per 5 minutes for more than 60 minutes period. Total number of rotations and the duration of the response in experimental period were presented as mean value. As comparative example, ropinirole as non-ergot dopamine $D_2$ receptor agonist, was examined in a similar fashion. These results were shown in Table 13.

TABLE 13

| Compound No. | Duration (minuets) | Total number of rotations |
|---|---|---|
| 1-1 | 541.3 | 5038.5 |
| 1-2 | 307.5 | 2580.0 |
| 1-3 | 387.5 | 3610.5 |
| 1-4 | 538.8 | 3975.0 |
| 1-23 | 870.0 | 9184.0 |
| 1-25 | 621.3 | 5025.0 |
| Ropinirole | 61.3 | 276.3 |

As a result of these experiments, it was recognized that the compounds of the present invention have remarkable long-lasting drug effects as compared with ropinirole.

INDUSTRIAL APPLICABILITY

Compounds of the present invention exhibit excellent dopamine $D_2$ receptor stimulating activities, and are accordingly useful for treating or preventing Parkinson's disease, restless legs syndrome or hyperprolactinemia.

SEQUENCE LISTING FREE TEXT

[SEQ ID No. 1]
Sequence ID No. 1 indicates the sequence of forward primer employed to amplify the DNA sequence shown in sequence ID No. 3.
[SEQ ID No. 2]
Sequence ID No. 2 indicates the sequence of reverse primer employed to amplify the DNA sequence shown in sequence ID No. 3.
[SEQ ID No. 3]
Sequence ID No. 3 indicates the DNA sequence, which was intended to express the recombinant human dopamine $D_2$ receptor, amplified by using primer pair shown in sequence ID No. 1 and 2.
[SEQ ID No. 4]
Sequence ID No. 4 indicates the sequence of forward primer employed to amplify the DNA sequence shown in sequence ID No. 6.
[SEQ ID No. 5]
Sequence ID No. 5 indicates the sequence of reverse primer employed to amplify the DNA sequence shown in sequence ID No. 6.
[SEQ ID No. 6]
Sequence ID No. 6 indicates the DNA sequence, which was intended to express the recombinant human serotonin 5-$HT_{2B}$ receptor, amplified by using primer pair shown in sequence ID No. 4 and 5.

The invention claimed is:
1. A compound represented by the formula (I):

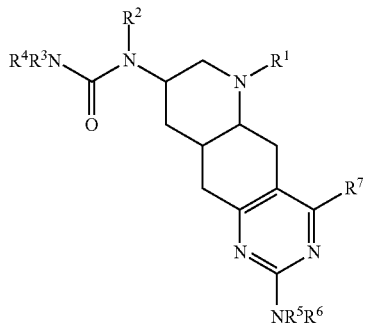

or a pharmaceutically acceptable salt thereof,
wherein
$R^1$ is any one of the following a), b) or c):
a) a $C_{1-6}$ alkyl group,
b) a halo-$C_{1-6}$ alkyl group, or
c) a $C_{2-6}$ alkenyl group;
$R^2$ is any one of a hydrogen atom or a $C_{1-6}$ alkyl group;
$R^3$ and $R^4$ are each independently any one of the following a), b), c), d), e), f) or g):
a) a hydrogen atom,
b) a $C_{1-6}$ alkyl group,
c) a cycloalkyl group,
d) an aralkyl group, wherein the ring of the aralkyl group is unsubstituted or substituted with 1 to 5 substituents selected from the group consisting of a halogen atom, a $C_{1-6}$ alkyl group, a halo-$C_{1-6}$ alkyl group, a $C_{1-6}$ alkoxy group, and a hydroxy-$C_{1-6}$ alkyl group,
e) a heteroaryl-$C_{1-6}$ alkyl group, wherein the ring of the heteroaryl-$C_{1-6}$ alkyl group is unsubstituted or substituted with 1 to 3 substituents independently selected from the group consisting of a $C_{1-6}$ alkyl group, a halo-$C_{1-6}$ alkyl group, and a $C_{1-6}$ alkoxy group,
f) a $C_{1-6}$ alkoxy-$C_{1-6}$ alkyl group, or
g) a $R^{10}R^{11}N$—$C_{1-6}$ alkyl group,
or $R^3$ and $R^4$, together with the nitrogen atom to which they are bonded, form any one of the following a) or b):
a) a cyclic amino group unsubstituted or substituted with 1 or 2 $C_{1-6}$ alkyl groups or phenyl groups, or
b) a benzo-fused cyclic amino group;
$R^5$ and $R^6$ are each independently any one of a hydrogen atom or a $C_{1-7}$ acyl group;
$R^7$ is any one of the following a), b), c), d) or e):
a) a hydrogen atom,
b) a halogen atom,
c) a $C_{1-6}$ alkyl group,
d) an amino group, or
e) a hydroxy group; and
$R^{10}$ and $R^{11}$ are each independently any one of the following a), b), c), d), e) or f):
a) a hydrogen atom,
b) a $C_{1-6}$ alkyl group,
c) a cycloalkyl group,
d) a $C_{1-6}$ alkoxy-$C_{1-6}$ alkyl group,
e) a phenyl group, or
f) an aralkyl group,
or $R^{10}$ and $R^{11}$, together with the nitrogen atom to which they are bonded, form any one of the following a) or b):

a) a cyclic amino group unsubstituted or substituted with 1 or 2 halogen atoms, $C_{1-6}$ alkyl groups or phenyl groups, or
b) a benzo-fused cyclic amino group.

2. The compound according to claim 1, or a pharmaceutically acceptable salt thereof, wherein $R^5$, $R^6$ and $R^7$ are each independently a hydrogen atom.

3. The compound according to claim 2, or a pharmaceutically acceptable salt thereof, wherein $R^1$ is a $C_{1-6}$ alkyl group.

4. The compound according to claim 3, or a pharmaceutically acceptable salt thereof, wherein $R^2$ is a hydrogen atom.

5. The compound according to claim 4, or a pharmaceutically acceptable salt thereof, wherein $R^3$ is any one of the following a), b) or c):
a) a hydrogen atom,
b) a $C_{1-6}$ alkyl group, or
c) an aralkyl group, wherein the ring of the aralkyl group is unsubstituted or substituted with 1 to 5 substituents selected from the group consisting of a halogen atom, a $C_{1-6}$ alkyl group, a halo-$C_{1-6}$ alkyl group, a $C_{1-6}$ alkoxy group and a hydroxy-$C_{1-6}$ alkyl group; and $R^4$ is any one of the following a), b), c), d), e) or f):
a) a $C_{1-6}$ alkyl group,
b) a cycloalkyl group,
c) an aralkyl group, wherein the ring of the aralkyl group is unsubstituted or substituted with 1 to 5 substituents selected from the group consisting of a halogen atom, a $C_{1-6}$ alkyl group, a halo-$C_{1-6}$ alkyl group, a $C_{1-6}$ alkoxy group and a hydroxy-$C_{1-6}$ alkyl group,
d) a heteroaryl-$C_{1-6}$ alkyl group, wherein the ring of the heteroaryl-$C_{1-6}$ alkyl group is unsubstituted or substituted with 1 to 3 substituents independently selected from the group consisting of a $C_{1-6}$ alkyl group, a halo-$C_{1-6}$ alkyl group, and a $C_{1-6}$ alkoxy group,
e) a $C_{1-6}$ alkoxy-$C_{1-6}$ alkyl group, or
f) a $R^{10}R^{11}N$—$C_{1-6}$ alkyl group,
or $R^3$ and $R^4$, together with the nitrogen atom to which they are bonded, form any one of the following a) or b):
a) a cyclic amino group unsubstituted or substituted with 1 or 2 $C_{1-6}$ alkyl groups or phenyl groups, or
b) a benzo-fused cyclic amino group.

6. The compound according to claim 5, or a pharmaceutically acceptable salt thereof, wherein $R^3$ is any one of the following a) or b):
a) a $C_{1-6}$ alkyl group, or
b) an aralkyl group, wherein the ring of the aralkyl group is unsubstituted or substituted with 1 to 5 substituents selected from the group consisting of a halogen atom, a $C_{1-6}$ alkyl group, a halo-$C_{1-6}$ alkyl group, a $C_{1-6}$ alkoxy group and a hydroxy-$C_{1-6}$ alkyl group; and $R^4$ is a $R^{10}R^{11}N$—$C_{1-6}$ alkyl group,
or $R^3$ and $R^4$, together with the nitrogen atom to which they are bonded, form a cyclic amino group, wherein the cyclic amino group is unsubstituted or substituted with 1 or 2 $C_{1-6}$ alkyl groups or phenyl groups.

7. The compound according to claim 1, or a pharmaceutically acceptable salt thereof, wherein
the compound is represented by the formula (II):

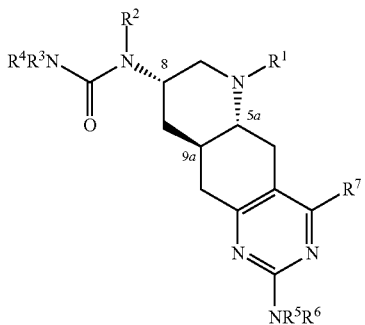

wherein the configuration at the 5a, 8 and 9a positions is represented by a relative configuration.

8. The compound according to claim 1, or a pharmaceutically acceptable salt thereof, wherein
the compound is represented by the formula (II):

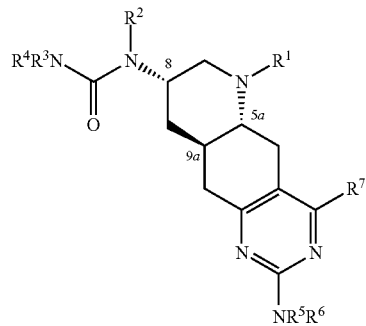

wherein the configuration at the 5a, 8 and 9a positions is represented by an absolute configuration.

9. A pharmaceutical composition comprising a compound according to claim 1, or a pharmaceutically acceptable salt thereof, and at least one pharmaceutically acceptable additive.

10. A pharmaceutical agent comprising a combination of a compound according to claim 1, or a pharmaceutically acceptable salt thereof, and at least one anti-Parkinson drug selected from the group consisting of amantadine hydrochloride, zonisamide, droxidopa, melevodopa, L-3,4-dihydroxyphenylalanine, threo-3-(3,4-dihydroxyphenyl)serine, a dopamine $D_2$ receptor agonist, a catechol-O-methyltransferase inhibitor, a monoamine oxidase B inhibitor, an anticholinergic agent, an adenosine $A_{2A}$ receptor antagonist, an N-methyl-D-aspartate receptor antagonist and an aromatic L-amino acid decarboxylase inhibitor.

11. A compound selected from the group consisting of:
3-[(5aR,8S,9aR)-2-amino-6-propyl-5,5a,6,7,8,9,9a,10-octahydropyrido[2,3-g]quinazolin-8-yl]-1-[2-(dimethylamino)ethyl]-1-ethylurea;
3-[(5aR,8S,9aR)-2-amino-6-propyl-5,5a,6,7,8,9,9a,10-octahydropyrido[2,3-g]quinazolin-8-yl]-1-[2-(dimethylamino)ethyl]-1-propylurea;
3-[(5aR,8S,9aR)-2-amino-6-propyl-5,5a,6,7,8,9,9a,10-octahydropyrido[2,3-g]quinazolin-8-yl]-1-[2-(dimethylamino)ethyl]-1-(2-methylpropyl)urea;
3-[(5aR,8S,9aR)-2-amino-6-propyl-5,5a,6,7,8,9,9a,10-octahydropyrido[2,3-g]quinazolin-8-yl]-1-[2-(diethylamino)ethyl]-1-methylurea;
3-[(5aR*,8S*,9aR*)-2-amino-6-propyl-5,5a,6,7,8,9,9a,10-octahydropyrido[2,3-g]quinazolin-8-yl]-1-[2-(dimethylamino)ethyl]-1-(2-phenylethyl)urea; and
3-[(5aR*,8S*,9aR*)-2-amino-6-propyl-5,5a,6,7,8,9,9a,10-octahydropyrido[2,3-g]quinazolin-8-yl]-1-ethyl-1-[2-(piperidin-1-yl)ethylurea;
or a pharmaceutically acceptable salt thereof,
wherein the mark "*" means the relative configuration of the assymetric carbon atom.

SEQUENCE LISTING

<160> NUMBER OF SEQ ID NOS: 6

<210> SEQ ID NO 1
<211> LENGTH: 25
<212> TYPE: DNA
<213> ORGANISM: Artificial sequence
<220> FEATURE:
<223> OTHER INFORMATION: forward primer

<400> SEQUENCE: 1
caccatggat ccactgaatc tgtcc                25

```
<210> SEQ ID NO 2
<211> LENGTH: 22
<212> TYPE: DNA
<213> ORGANISM: Artificial sequence
<220> FEATURE:
<223> OTHER INFORMATION: reverse primer

<400> SEQUENCE: 2
tcagcagtgg aggatcttca gg                                              22

<210> SEQ ID NO 3
<211> LENGTH: 1332
<212> TYPE: DNA
<213> ORGANISM: Homo sapiens

<400> SEQUENCE: 3
atggatccac tgaatctgtc ctggtatgat gatgatctgg agaggcagaa ctggagccgg     60
cccttcaacg ggtcagacgg gaaggcggac agaccccact acaactacta tgccacactg    120
ctcaccctgc tcatcgctgt catcgtcttc ggcaacgtgc tggtgtgcat ggctgtgtcc    180
cgcgagaagg cgctgcagac caccaccaac tacctgatcg tcagcctcgc agtggccgac    240
ctcctcgtcg ccacactggt catgcccctgg gttgtctacc tggaggtggt aggtgagtgg    300
aaattcagca ggattcactg tgacatcttc gtcactctgg acgtcatgat gtgcacggcg    360
agcatcctga acttgtgtgc catcagcatc gacaggtaca cagctgtggc catgcccatg    420
ctgtacaata cgcgctacag ctccaagcgc cgggtcaccg tcatgatctc catcgtctgg    480
gtcctgtcct tcaccatctc ctgcccactc tccttcggac tcaataacgc agaccagaac    540
gagtgcatca ttgccaaccc ggccttcgtg gtctactcct ccatcgtctc cttctacgtg    600
cccttcattg tcaccctgct ggtctacatc aagatctaca ttgtcctccg cagacgccgc    660
aagcgagtca acaccaaacg cagcagccga gctttcaggg cccacctgag ggctccacta    720
aagggcaact gtactcaccc cgaggacatg aaactctgca ccgttatcat gaagtctaat    780
gggagttttc cagtgaacag gcggagagtg gaggctgccc ggcgagccca ggagctggag    840
atggagatgc tctccagcac cagcccaccc gagaggaccc ggtacagccc catcccaccc    900
agccaccacc agctgactct ccccgacccg tccaccacg gtctccacag cactcccgac    960
agccccgcca accagagaa gaatgggcat gccaaagacc accccaagat tgccaagatc   1020
tttgagatca gaccatgcc caatggcaaa acccggacct ccctcaagac catgagccgt   1080
aggaagctct cccagcagaa ggagaagaaa gccactcaga tgctcgccat tgttctcggc   1140
gtgttcatca tctgctggct gcccttcttc atcacacaca tcctgaacat acactgtgac   1200
tgcaacatcc cgcctgtcct gtacagcgcc ttcacgtggc tgggctatgt caacagcgcc   1260
gtgaacccca tcatctacac caccttcaac attgagttcc gcaaggcctt cctgaagatc   1320
ctccactgct ga                                                       1332

<210> SEQ ID NO 4
<211> LENGTH: 22
<212> TYPE: DNA
<213> ORGANISM: Artificial sequence
<220> FEATURE:
<223> OTHER INFORMATION: forward primer

<400> SEQUENCE: 4
caccatggct ctctcttaca ga                                              22

<210> SEQ ID NO 5
```

```
<211> LENGTH: 18
<212> TYPE: DNA
<213> ORGANISM: Artificial sequence
<220> FEATURE:
<223> OTHER INFORMATION: reverse primer

<400> SEQUENCE: 5
atgtttgatg acaactgc                                                    18

<210> SEQ ID NO 6
<211> LENGTH: 1446
<212> TYPE: DNA
<213> ORGANISM: Homo sapiens

<400> SEQUENCE: 6
atggctctct cttacagagt gtctgaactt caaagcacaa ttcctgagca cattttgcag      60
agcacctttg ttcacgttat ctcttctaac tggtctggat tacagacaga atcaatacca     120
gaggaaatga aacagattgt tgaggaacag ggaaataaac tgcactgggc agctcttctg     180
atactcatgg tgataatacc cacaattggt ggaaataccc ttgttattct ggctgtttca     240
ctggagaaga agctgcagta tgctactaat tactttctaa tgtccttggc ggtggctgat     300
ttgctggttg gattgtttgt gatgccaatt gccctcttga caataatgtt tgaggctatg     360
tggcccctcc cacttgttct atgtcctgcc tggttatttc ttgacgttct cttttcaacc     420
gcatccatca tgcatctctg tgccatttca gtggatcgtt acatagccat caaaaagcca     480
atccaggcca atcaatataa ctcacgggct acagcattca tcaagattac agtggtgtgg     540
ttaatttcaa taggcattgc cattccagtc cctattaaag ggatagagac tgatgtggac     600
aacccaaaca atatcacttg tgtgctgaca aaggaacgtt ttggcgattt catgctcttt     660
ggctcactgg ctgccttctt cacacctctt gcaattatga ttgtcaccta ctttctcact     720
atccatgctt tacagaagaa ggcttactta gtcaaaaaca agccacctca acgcctaaca     780
tggttgactg tgtctacagt tttccaaagg gatgaaacac cttgctcgtc accggaaaag     840
gtggcaatgc tggatggttc tcgaaaggac aaggctctgc ccaactcagg tgatgaaaca     900
cttatgcgaa gaacatccac aattgggaaa aagtcagtgc agaccatttc caacgaacag     960
agagcctcaa aggtcctagg gattgtgttt ttcctctttt tgcttatgtg gtgtcccttc    1020
tttattacaa atataacttt agttttatgt gattcctgta accaaactac tctccaaatg    1080
ctcctggaga tatttgtgtg gataggctat gttttcctcag gagtgaatcc tttggtctac    1140
accctcttca ataagacatt tcgggatgca tttggccgat atatcacctg caattaccgg    1200
gccacaaagt cagtaaaaac tctcagaaaa cgctccagta agatctactt ccggaatcca    1260
atggcagaga actctaagtt tttcaagaaa catggaattc gaaatgggat taaccctgcc    1320
atgtaccaga gtccaatgag gctccgaagt tcaaccattc agtcttcatc aatcattcta    1380
ctagatacgc ttctcctcac tgaaaatgaa ggtgacaaaa ctgaagagca agttagttat    1440
gtatag                                                              1446
```